United States Patent [19]
Baker et al.

[11] Patent Number: 5,212,058
[45] Date of Patent: May 18, 1993

[54] NUCLEIC ACID ENCODING UBIQUITIN-SPECIFIC PROTEASES

[75] Inventors: Rohan T. Baker, Garran, Australia; John W. Tobias, Cambridge; Alexander Varshavsky, Boston, both of Mass.

[73] Assignee: Massachusetts Institute of Technology, Cambridge, Mass.

[21] Appl. No.: 789,915

[22] Filed: Nov. 8, 1991

Related U.S. Application Data

[63] Continuation-in-part of Ser. No. 573,958, Aug. 28, 1990, abandoned, which is a continuation-in-part of Ser. No. 521,089, May 9, 1990, abandoned.

[51] Int. Cl.$^5$ .............. C12Q 1/68; C07H 21/04; C12N 15/57; C12N 15/66; C12N 15/70
[52] U.S. Cl. .............. 435/252.33; 536/23.2; 536/23.4; 435/320.1; 435/240.2; 435/252.3; 435/6
[58] Field of Search .............. 536/27; 435/320.1, 243, 435/252.3, 252.8, 6, 252.33

[56] References Cited

U.S. PATENT DOCUMENTS 5,132,213  7/1992  Bachmair et al. .............. 435/69.7

FOREIGN PATENT DOCUMENTS

W088/2406  4/1988  PCT Int'l Appl.
W059/12678  6/1989  PCT Int'l Appl.

OTHER PUBLICATIONS

Ohmen et al. N.A.R. 16(22): 10783–10802, 1988.
Ohmen et al. Mol. Cell Biol. 10(6):3027–3035, 1990.
K. Nagai and H. C. Thogersen, *Nature* 309:810–812 (1984).
Hershko et al., *Proc. Natl. Acad. Sci. USA* 81:7021–7025 (1984).
Tsunasawa et al., *J. Biol. Chem.* 260:5382–5391 (1985).
Boissel et al., *Proc. Natl. Acad. Sci. USA* 82:8448–8452 (1985).
Thornton et al., *J. Mol. Biol.* 167:443–460 (1983).
Ferber et al., *J. Biol. Chem.* 261:3128–3134 (1986).
Bachmair et al., *Science* 234:179–186 (1986).
Ferber et al., *Nature* 326:808–811 (1988).
Reiss et al., *J. Biol. Chem.* 263:2693–2698 (1988).
Townsend et al., *J. Exp. Med.* 168:1211–1224 (1988).
Bachmair and Varshavsky, *Cell* 56:1019–1032 (1989).
Chau et al., *Science* 243:1576–1583 (1989).
Gonda et al., *J. Biol. Chem.* 264: 16700–16712 (1989).
Miller et al., *Biotechnology* 1:698–704 (1989).
International Search Report.
Sassenfeld, *Trends in Biotechnol* 8:88–93 (1990).
Wilkinson et al., *Science* 246:670–673 (1989).
Tobias and Varshavsky, *J. Biol. Chem.* 266:12021–12028 (1991).

*Primary Examiner*—Margaret Moskowitz
*Assistant Examiner*—Paul Tran
*Attorney, Agent, or Firm*—Hamilton, Brook, Smith & Reynolds

[57] ABSTRACT

The disclosure relates to a generic class of ubiquitin-specific proteases which specifically cleave at the C-terminus of the ubiquitin moiety in a ubiquitin fusion protein irrespective of the size of the ubiquitin fusion protein. More specifically, the disclosure relates to ubiquitin-specific proteases of this class which have been isolated from a cell. The disclosure also relates to isolated DNA sequences encoding the proteases of this class.

11 Claims, 4 Drawing Sheets

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 3365 base pairs
( B ) TYPE: nucleic acid
( C ) STRANDEDNESS: double
( D ) TOPOLOGY: linear ( i x ) FEATURE:
( A ) NAME/KEY: CDS
( B ) LOCATION: 1..3363

( x i ) SEQUENCE DESCRIPTION: SEQ ID NO:1:

```
ATG  CAG  ATT  TTC  GTC  AAG  ACT  TTG  ACC  GGT  AAA  ACC  ATA  ACA  TTG  GAA      48
Met  Gln  Ile  Phe  Val  Lys  Thr  Leu  Thr  Gly  Lys  Thr  Ile  Thr  Leu  Glu
 1                 5                      10                     15

GTT  GAA  TCT  TCC  GAT  ACC  ATC  GAC  AAC  GTT  AAG  TCG  AAA  ATT  CAA  GAC      96
Val  Glu  Ser  Ser  Asp  Thr  Ile  Asp  Asn  Val  Lys  Ser  Lys  Ile  Gln  Asp
                  20                     25                     30

AAG  GAA  GGT  ATC  CCT  CCA  GAT  CAA  CAA  AGA  TTG  ATC  TTT  GCC  GGT  AAG     144
Lys  Glu  Gly  Ile  Pro  Pro  Asp  Gln  Gln  Arg  Leu  Ile  Phe  Ala  Gly  Lys
             35                     40                     45

CAG  CTA  GAA  GAC  GGT  AGA  ACG  CTG  TCT  GAT  TAC  AAC  ATT  CAG  AAG  GAG     192
Gln  Leu  Glu  Asp  Gly  Arg  Thr  Leu  Ser  Asp  Tyr  Asn  Ile  Gln  Lys  Glu
         50                     55                     60

TCC  ACC  TTA  CAT  CTT  GTG  CTA  AGG  CTA  AGA  GGT  GGT  ATG  CAC  GGA  TCC     240
Ser  Thr  Leu  His  Leu  Val  Leu  Arg  Leu  Arg  Gly  Gly  Met  His  Gly  Ser
```

-continued

| | | | | | | | | | | | | | | | | |
|---|---|---|---|---|---|---|---|---|---|---|---|---|---|---|---|---|
| 65 | | | | | 70 | | | | | 75 | | | | | 80 | |
| GGA | GCT | TGG | CTG | TTG | CCC | GTC | TCA | CTG | GTG | AAA | AGA | AAA | ACC | ACC | CTG | 288 |
| Gly | Ala | Trp | Leu | Leu | Pro | Val | Ser | Leu | Val | Lys | Arg | Lys | Thr | Thr | Leu | |
| | | | | 85 | | | | | 90 | | | | | 95 | | |
| GCG | CCC | AAT | ACG | CAA | ACC | GCC | TCT | CCC | CGC | GCG | TTG | GCC | GAT | TCA | TTA | 336 |
| Ala | Pro | Asn | Thr | Gln | Thr | Ala | Ser | Pro | Arg | Ala | Leu | Ala | Asp | Ser | Leu | |
| | | | | 100 | | | | | 105 | | | | | 110 | | |
| ATG | CAG | CTG | GCA | CGA | CAG | GTT | TCC | CGA | CTT | AAT | CGC | CTT | GCA | GCA | CAT | 384 |
| Met | Gln | Leu | Ala | Arg | Gln | Val | Ser | Arg | Leu | Asn | Arg | Leu | Ala | Ala | His | |
| | | | | 115 | | | | | 120 | | | | | 125 | | |
| CCC | CCT | TTC | GCC | AGC | TGG | CGT | AAT | AGC | GAA | GAG | GCC | CGC | ACC | GAT | CGC | 432 |
| Pro | Pro | Phe | Ala | Ser | Trp | Arg | Asn | Ser | Glu | Glu | Ala | Arg | Thr | Asp | Arg | |
| | | | | 130 | | | | | 135 | | | | | 140 | | |
| CCT | TCC | CAA | CAG | TTG | CGC | AGC | CTG | AAT | GGC | GAA | TGG | CGC | TTT | GCC | TGG | 480 |
| Pro | Ser | Gln | Gln | Leu | Arg | Ser | Leu | Asn | Gly | Glu | Trp | Arg | Phe | Ala | Trp | |
| 145 | | | | | 150 | | | | | 155 | | | | | 160 | |
| TTT | CCG | GCA | CCA | GAA | GCG | GTG | CCG | GAA | AGC | TGG | CTG | GAG | TGC | GAT | CTT | 528 |
| Phe | Pro | Ala | Pro | Glu | Ala | Val | Pro | Glu | Ser | Trp | Leu | Glu | Cys | Asp | Leu | |
| | | | | 165 | | | | | 170 | | | | | 175 | | |
| CCT | GAG | GCC | GAT | ACT | GTC | GTC | GTC | CCC | TCA | AAC | TGG | CAG | ATG | CAC | GGT | 576 |
| Pro | Glu | Ala | Asp | Thr | Val | Val | Val | Pro | Ser | Asn | Trp | Gln | Met | His | Gly | |
| | | | | 180 | | | | | 185 | | | | | 190 | | |
| TAC | GAT | GCG | CCC | ATC | TAC | ACC | AAC | GTA | ACC | TAT | CCC | ATT | ACG | GTC | AAT | 624 |
| Tyr | Asp | Ala | Pro | Ile | Tyr | Thr | Asn | Val | Thr | Tyr | Pro | Ile | Thr | Val | Asn | |
| | | | | 195 | | | | | 200 | | | | | 205 | | |
| CCG | CCG | TTT | GTT | CCC | ACG | GAG | AAT | CCG | ACG | GGT | TGT | TAC | TCG | CTC | ACA | 672 |
| Pro | Pro | Phe | Val | Pro | Thr | Glu | Asn | Pro | Thr | Gly | Cys | Tyr | Ser | Leu | Thr | |
| | | | | 210 | | | | | 215 | | | | | 220 | | |
| TTT | AAT | GTT | GAT | GAA | AGC | TGG | CTA | CAG | GAA | GGC | CAG | ACG | CGA | ATT | ATT | 720 |
| Phe | Asn | Val | Asp | Glu | Ser | Trp | Leu | Gln | Glu | Gly | Gln | Thr | Arg | Ile | Ile | |
| 225 | | | | | 230 | | | | | 235 | | | | | 240 | |
| TTT | GAT | GGC | GTT | AAC | TCG | GCG | TTT | CAT | CTG | TGG | TGC | AAC | GGG | CGC | TGG | 768 |
| Phe | Asp | Gly | Val | Asn | Ser | Ala | Phe | His | Leu | Trp | Cys | Asn | Gly | Arg | Trp | |
| | | | | 245 | | | | | 250 | | | | | 255 | | |
| GTC | GGT | TAC | GGC | CAG | GAC | AGT | CGT | TTG | CCG | TCT | GAA | TTT | GAC | CTG | AGC | 816 |
| Val | Gly | Tyr | Gly | Gln | Asp | Ser | Arg | Leu | Pro | Ser | Glu | Phe | Asp | Leu | Ser | |
| | | | | 260 | | | | | 265 | | | | | 270 | | |
| GCA | TTT | TTA | CGC | GCC | GGA | GAA | AAC | CGC | CTC | GCG | GTG | ATG | GTG | CTG | CGT | 864 |
| Ala | Phe | Leu | Arg | Ala | Gly | Glu | Asn | Arg | Leu | Ala | Val | Met | Val | Leu | Arg | |
| | | | | 275 | | | | | 280 | | | | | 285 | | |
| TGG | AGT | GAC | GGC | AGT | TAT | CTG | GAA | GAT | CAG | GAT | ATG | TGG | CGG | ATG | AGC | 912 |
| Trp | Ser | Asp | Gly | Ser | Tyr | Leu | Glu | Asp | Gln | Asp | Met | Trp | Arg | Met | Ser | |
| | | | | 290 | | | | | 295 | | | | | 300 | | |
| GGC | ATT | TTC | CGT | GAC | GTC | TCG | TTG | CTG | CAT | AAA | CCG | ACT | ACA | CAA | ATC | 960 |
| Gly | Ile | Phe | Arg | Asp | Val | Ser | Leu | Leu | His | Lys | Pro | Thr | Thr | Gln | Ile | |
| 305 | | | | | 310 | | | | | 315 | | | | | 320 | |
| AGC | GAT | TTC | CAT | GTT | GCC | ACT | CGC | TTT | AAT | GAT | GAT | TTC | AGC | CGC | GCT | 1008 |
| Ser | Asp | Phe | His | Val | Ala | Thr | Arg | Phe | Asn | Asp | Asp | Phe | Ser | Arg | Ala | |
| | | | | 325 | | | | | 330 | | | | | 335 | | |
| GTA | CTG | GAG | GCT | GAA | GTT | CAG | ATG | TGC | GGC | GAG | TTG | CGT | GAC | TAC | CTA | 1056 |
| Val | Leu | Glu | Ala | Glu | Val | Gln | Met | Cys | Gly | Glu | Leu | Arg | Asp | Tyr | Leu | |
| | | | | 340 | | | | | 345 | | | | | 350 | | |
| CGG | GTA | ACA | GTT | TCT | TTA | TGG | CAG | GGT | GAA | ACG | CAG | GTC | GCC | AGC | GGC | 1104 |
| Arg | Val | Thr | Val | Ser | Leu | Trp | Gln | Gly | Glu | Thr | Gln | Val | Ala | Ser | Gly | |
| | | | | 355 | | | | | 360 | | | | | 365 | | |
| ACC | GCG | CCT | TTC | GGC | GGT | GAA | ATT | ATC | GAT | GAG | CGT | GGT | GGT | TAT | GCC | 1152 |
| Thr | Ala | Pro | Phe | Gly | Gly | Glu | Ile | Ile | Asp | Glu | Arg | Gly | Gly | Tyr | Ala | |
| | | | | 370 | | | | | 375 | | | | | 380 | | |
| GAT | CGC | GTC | ACA | CTA | CGT | CTG | AAC | GTC | GAA | AAC | CCG | AAA | CTG | TGG | AGC | 1200 |
| Asp | Arg | Val | Thr | Leu | Arg | Leu | Asn | Val | Glu | Asn | Pro | Lys | Leu | Trp | Ser | |
| 385 | | | | | 390 | | | | | 395 | | | | | 400 | |

| | | | | | | | | | | | | | | | | |
|---|---|---|---|---|---|---|---|---|---|---|---|---|---|---|---|---|
| GCC | GAA | ATC | CCG | AAT | CTC | TAT | CGT | GCG | GTG | GTT | GAA | CTG | CAC | ACC | GCC | 1248 |
| Ala | Glu | Ile | Pro | Asn | Leu | Tyr | Arg | Ala | Val | Val | Glu | Leu | His | Thr | Ala | |
| | | | 405 | | | | | 410 | | | | | 415 | | | |
| GAC | GGC | ACG | CTG | ATT | GAA | GCA | GAA | GCC | TGC | GAT | GTC | GGT | TTC | CGC | GAG | 1296 |
| Asp | Gly | Thr | Leu | Ile | Glu | Ala | Glu | Ala | Cys | Asp | Val | Gly | Phe | Arg | Glu | |
| | | 420 | | | | | 425 | | | | | 430 | | | | |
| GTG | CGG | ATT | GAA | AAT | GGT | CTG | CTG | CTG | CTG | AAC | GGC | AAG | CCG | TTG | CTG | 1344 |
| Val | Arg | Ile | Glu | Asn | Gly | Leu | Leu | Leu | Leu | Asn | Gly | Lys | Pro | Leu | Leu | |
| | | 435 | | | | | 440 | | | | | 445 | | | | |
| ATT | CGA | GGC | GTT | AAC | CGT | CAC | GAG | CAT | CAT | CCT | CTG | CAT | GGT | CAG | GTC | 1392 |
| Ile | Arg | Gly | Val | Asn | Arg | His | Glu | His | His | Pro | Leu | His | Gly | Gln | Val | |
| | 450 | | | | | 455 | | | | | 460 | | | | | |
| ATG | GAT | GAG | CAG | ACG | ATG | GTG | CAG | GAT | ATC | CTG | CTG | ATG | AAG | CAG | AAC | 1440 |
| Met | Asp | Glu | Gln | Thr | Met | Val | Gln | Asp | Ile | Leu | Leu | Met | Lys | Gln | Asn | |
| 465 | | | | | 470 | | | | | 475 | | | | | 480 | |
| AAC | TTT | AAC | GCC | GTG | CGC | TGT | TCG | CAT | TAT | CCG | AAC | CAT | CCG | CTG | TGG | 1488 |
| Asn | Phe | Asn | Ala | Val | Arg | Cys | Ser | His | Tyr | Pro | Asn | His | Pro | Leu | Trp | |
| | | | | 485 | | | | | 490 | | | | | 495 | | |
| TAC | ACG | CTG | TGC | GAC | CGC | TAC | GGC | CTG | TAT | GTG | GTG | GAT | GAA | GCC | AAT | 1536 |
| Tyr | Thr | Leu | Cys | Asp | Arg | Tyr | Gly | Leu | Tyr | Val | Val | Asp | Glu | Ala | Asn | |
| | | | 500 | | | | | 505 | | | | | 510 | | | |
| ATT | GAA | ACC | CAC | GGC | ATG | GTG | CCA | ATG | AAT | CGT | CTG | ACC | GAT | GAT | CCG | 1584 |
| Ile | Glu | Thr | His | Gly | Met | Val | Pro | Met | Asn | Arg | Leu | Thr | Asp | Asp | Pro | |
| | | 515 | | | | | 520 | | | | | 525 | | | | |
| CGC | TGG | CTA | CCG | GCG | ATG | AGC | GAA | CGC | GTA | ACG | CGA | ATG | GTG | CAG | CGC | 1632 |
| Arg | Trp | Leu | Pro | Ala | Met | Ser | Glu | Arg | Val | Thr | Arg | Met | Val | Gln | Arg | |
| | | 530 | | | | | 535 | | | | | 540 | | | | |
| GAT | CGT | AAT | CAC | CCG | AGT | GTG | ATC | ATC | TGG | TCG | CTG | GGG | AAT | GAA | TCA | 1680 |
| Asp | Arg | Asn | His | Pro | Ser | Val | Ile | Ile | Trp | Ser | Leu | Gly | Asn | Glu | Ser | |
| 545 | | | | | 550 | | | | | 555 | | | | | 560 | |
| GGC | CAC | GGC | GCT | AAT | CAC | GAC | GCG | CTG | TAT | CGC | TGG | ATC | AAA | TCT | GTC | 1728 |
| Gly | His | Gly | Ala | Asn | His | Asp | Ala | Leu | Tyr | Arg | Trp | Ile | Lys | Ser | Val | |
| | | | | 565 | | | | | 570 | | | | | 575 | | |
| GAT | CCT | TCC | CGC | CCG | GTG | CAG | TAT | GAA | GGC | GGC | GGA | GCC | GAC | ACC | ACG | 1776 |
| Asp | Pro | Ser | Arg | Pro | Val | Gln | Tyr | Glu | Gly | Gly | Gly | Ala | Asp | Thr | Thr | |
| | | | 580 | | | | | 585 | | | | | 590 | | | |
| GCC | ACC | GAT | ATT | ATT | TGC | CCG | ATG | TAC | GCG | CGC | GTG | GAT | GAA | GAC | CAG | 1824 |
| Ala | Thr | Asp | Ile | Ile | Cys | Pro | Met | Tyr | Ala | Arg | Val | Asp | Glu | Asp | Gln | |
| | | 595 | | | | | 600 | | | | | 605 | | | | |
| CCC | TTC | CCG | GCT | GTG | CCG | AAA | TGG | TCC | ATC | AAA | AAA | TGG | CTT | TCG | CTA | 1872 |
| Pro | Phe | Pro | Ala | Val | Pro | Lys | Trp | Ser | Ile | Lys | Lys | Trp | Leu | Ser | Leu | |
| | 610 | | | | | 615 | | | | | 620 | | | | | |
| CCT | GGA | GAG | ACG | CGC | CCG | CTG | ATC | CTT | TGC | GAA | TAC | GCC | CAC | GCG | ATG | 1920 |
| Pro | Gly | Glu | Thr | Arg | Pro | Leu | Ile | Leu | Cys | Glu | Tyr | Ala | His | Ala | Met | |
| 625 | | | | | 630 | | | | | 635 | | | | | 640 | |
| GGT | AAC | AGT | CTT | GGC | GGT | TTC | GCT | AAA | TAC | TGG | CAG | GCG | TTT | CGT | CAG | 1968 |
| Gly | Asn | Ser | Leu | Gly | Gly | Phe | Ala | Lys | Tyr | Trp | Gln | Ala | Phe | Arg | Gln | |
| | | | | 645 | | | | | 650 | | | | | 655 | | |
| TAT | CCC | CGT | TTA | CAG | GGC | GGC | TTC | GTC | TGG | GAC | TGG | GTG | GAT | CAG | TCG | 2016 |
| Tyr | Pro | Arg | Leu | Gln | Gly | Gly | Phe | Val | Trp | Asp | Trp | Val | Asp | Gln | Ser | |
| | | | 660 | | | | | 665 | | | | | 670 | | | |
| CTG | ATT | AAA | TAT | GAT | GAA | AAC | GGC | AAC | CCG | TGG | TCG | GCT | TAC | GGC | GGT | 2064 |
| Leu | Ile | Lys | Tyr | Asp | Glu | Asn | Gly | Asn | Pro | Trp | Ser | Ala | Tyr | Gly | Gly | |
| | | 675 | | | | | 680 | | | | | 685 | | | | |
| GAT | TTT | GGC | GAT | ACG | CCG | AAC | GAT | CGC | CAG | TTC | TGT | ATG | AAC | GGT | CTG | 2112 |
| Asp | Phe | Gly | Asp | Thr | Pro | Asn | Asp | Arg | Gln | Phe | Cys | Met | Asn | Gly | Leu | |
| | 690 | | | | | 695 | | | | | 700 | | | | | |
| GTC | TTT | GCC | GAC | CGC | ACG | CCG | CAT | CCA | GCG | CTG | ACG | GAA | GCA | AAA | CAC | 2160 |
| Val | Phe | Ala | Asp | Arg | Thr | Pro | His | Pro | Ala | Leu | Thr | Glu | Ala | Lys | His | |
| 705 | | | | | 710 | | | | | 715 | | | | | 720 | |
| CAG | CAG | CAG | TTT | TTC | CAG | TTC | CGT | TTA | TCC | GGG | CAA | ACC | ATC | GAA | GTG | 2208 |
| Gln | Gln | Gln | Phe | Phe | Gln | Phe | Arg | Leu | Ser | Gly | Gln | Thr | Ile | Glu | Val | |

-continued

| | | | |
|---|---|---|---|
| | 725 | 730 | 735 |
| ACC AGC GAA TAC CTG TTC CGT CAT AGC GAT AAC GAG CTC CTG CAC TGG | | | 2256 |
| Thr Ser Glu Tyr Leu Phe Arg His Ser Asp Asn Glu Leu Leu His Trp | | | |
| 740 745 750 | | | |
| ATG GTG GCG CTG GAT GGT AAG CCG CTG GCA AGC GGT GAA GTG CCT CTG | | | 2304 |
| Met Val Ala Leu Asp Gly Lys Pro Leu Ala Ser Gly Glu Val Pro Leu | | | |
| 755 760 765 | | | |
| GAT GTC GCT CCA CAA GGT AAA CAG TTG ATT GAA CTG CCT GAA CTA CCG | | | 2352 |
| Asp Val Ala Pro Gln Gly Lys Gln Leu Ile Glu Leu Pro Glu Leu Pro | | | |
| 770 775 780 | | | |
| CAG CCG GAG AGC GCC GGG CAA CTC TGG CTC ACA GTA CGC GTA GTG CAA | | | 2400 |
| Gln Pro Glu Ser Ala Gly Gln Leu Trp Leu Thr Val Arg Val Val Gln | | | |
| 785 790 795 800 | | | |
| CCG AAC GCG ACC GCA TGG TCA GAA GCC GGG CAC ATC AGC GCC TGG CAG | | | 2448 |
| Pro Asn Ala Thr Ala Trp Ser Glu Ala Gly His Ile Ser Ala Trp Gln | | | |
| 805 810 815 | | | |
| CAG TGG CGT CTG GCG GAA AAC CTC AGT GTG ACG CTC CCC GCC GCG TCC | | | 2496 |
| Gln Trp Arg Leu Ala Glu Asn Leu Ser Val Thr Leu Pro Ala Ala Ser | | | |
| 820 825 830 | | | |
| CAC GCC ATC CCG CAT CTG ACC ACC AGC GAA ATG GAT TTT TGC ATC GAG | | | 2544 |
| His Ala Ile Pro His Leu Thr Thr Ser Glu Met Asp Phe Cys Ile Glu | | | |
| 835 840 845 | | | |
| CTG GGT AAT AAG CGT TGG CAA TTT AAC CGC CAG TCA GGC TTT CTT TCA | | | 2592 |
| Leu Gly Asn Lys Arg Trp Gln Phe Asn Arg Gln Ser Gly Phe Leu Ser | | | |
| 850 855 860 | | | |
| CAG ATG TGG ATT GGC GAT AAA AAA CAA CTG CTG ACG CCG CTG CGC GAT | | | 2640 |
| Gln Met Trp Ile Gly Asp Lys Lys Gln Leu Leu Thr Pro Leu Arg Asp | | | |
| 865 870 875 880 | | | |
| CAG TTC ACC CGT GCA CCG CTG GAT AAC GAC ATT GGC GTA AGT GAA GCG | | | 2688 |
| Gln Phe Thr Arg Ala Pro Leu Asp Asn Asp Ile Gly Val Ser Glu Ala | | | |
| 885 890 895 | | | |
| ACC CGC ATT GAC CCT AAC GCC TGG GTC GAA CGC TGG AAG GCG GCG GGC | | | 2736 |
| Thr Arg Ile Asp Pro Asn Ala Trp Val Glu Arg Trp Lys Ala Ala Gly | | | |
| 900 905 910 | | | |
| CAT TAC CAG GCC GAA GCA GCG TTG TTG CAG TGC ACG GCA GAT ACA CTT | | | 2784 |
| His Tyr Gln Ala Glu Ala Ala Leu Leu Gln Cys Thr Ala Asp Thr Leu | | | |
| 915 920 925 | | | |
| GCT GAT GCG GTG CTG ATT ACG ACC GCT CAC GCG TGG CAG CAT CAG GGG | | | 2832 |
| Ala Asp Ala Val Leu Ile Thr Thr Ala His Ala Trp Gln His Gln Gly | | | |
| 930 935 940 | | | |
| AAA ACC TTA TTT ATC AGC CGG AAA ACC TAC CGG ATT GAT GGT AGT GGT | | | 2880 |
| Lys Thr Leu Phe Ile Ser Arg Lys Thr Tyr Arg Ile Asp Gly Ser Gly | | | |
| 945 950 955 960 | | | |
| CAA ATG GCG ATT ACC GTT GAT GTT GAA GTG GCG AGC GAT ACA CCG CAT | | | 2928 |
| Gln Met Ala Ile Thr Val Asp Val Glu Val Ala Ser Asp Thr Pro His | | | |
| 965 970 975 | | | |
| CCG GCG CGG ATT GGC CTG AAC TGC CAG CTG GCG CAG GTA GCA GAG CGG | | | 2976 |
| Pro Ala Arg Ile Gly Leu Asn Cys Gln Leu Ala Gln Val Ala Glu Arg | | | |
| 980 985 990 | | | |
| GTA AAC TGG CTC GGA TTA GGG CCG CAA GAA AAC TAT CCC GAC CGC CTT | | | 3024 |
| Val Asn Trp Leu Gly Leu Gly Pro Gln Glu Asn Tyr Pro Asp Arg Leu | | | |
| 995 1000 1005 | | | |
| ACT GCC GCC TGT TTT GAC CGC TGG GAT CTG CCA TTG TCA GAC ATG TAT | | | 3072 |
| Thr Ala Ala Cys Phe Asp Arg Trp Asp Leu Pro Leu Ser Asp Met Tyr | | | |
| 1010 1015 1020 | | | |
| ACC CCG TAC GTC TTC CCG AGC GAA AAC GGT CTG CGC TGC GGG ACG CGC | | | 3120 |
| Thr Pro Tyr Val Phe Pro Ser Glu Asn Gly Leu Arg Cys Gly Thr Arg | | | |
| 1025 1030 1035 1040 | | | |
| GAA TTG AAT TAT GGC CCA CAC CAG TGG CGC GGC GAC TTC CAG TTC AAC | | | 3168 |
| Glu Leu Asn Tyr Gly Pro His Gln Trp Arg Gly Asp Phe Gln Phe Asn | | | |
| 1045 1050 1055 | | | |

| | | | | | | | | | | | | | | | |
|---|---|---|---|---|---|---|---|---|---|---|---|---|---|---|---|
| ATC | AGC | CGC | TAC | AGT | CAA | CAG | CAA | CTG | ATG | GAA | ACC | AGC | CAT | CGC | CAT | 3216 |
| Ile | Ser | Arg | Tyr 1060 | Ser | Gln | Gln | Gln 1065 | Leu | Met | Glu | Thr | Ser 1070 | His | Arg | His |

| CTG | CTG | CAC | GCG | GAA | GAA | GGC | ACA | TGG | CTG | AAT | ATC | GAC | GGT | TTC | CAT | 3264 |
| Leu | Leu | His 1075 | Ala | Glu | Glu | Gly 1080 | Thr | Trp | Leu | Asn | Ile 1085 | Asp | Gly | Phe | His |

| ATG | GGG | ATT | GGT | GGC | GAC | GAC | TCC | TGG | AGC | CCG | TCA | GTA | TCG | GCG | GAA | 3312 |
| Met | Gly 1090 | Ile | Gly | Gly | Asp | Asp 1095 | Ser | Trp | Ser | Pro | Ser 1100 | Val | Ser | Ala | Glu |

| TTC | CAG | CTG | AGC | GCC | GGT | CGC | TAC | CAT | TAC | CAG | TTG | GTC | TGG | TGT | CAA | 3360 |
| Phe 1105 | Gln | Leu | Ser | Ala | Gly 1110 | Arg | Tyr | His | Tyr | Gln 1115 | Leu | Val | Trp | Cys | Gln 1120 |

| AAA | TA | | | | | | | | | | | | | | | 3365 |
| Lys | | | | | | | | | | | | | | | |

(2) INFORMATION FOR SEQ ID NO:2:

(i) SEQUENCE CHARACTERISTICS:
        (A) LENGTH: 1121 amino acids
        (B) TYPE: amino acid
        (D) TOPOLOGY: linear (ii) MOLECULE TYPE: protein (xi) SEQUENCE DESCRIPTION: SEQ ID NO:2:

| Met 1 | Gln | Ile | Phe | Val 5 | Lys | Thr | Leu | Thr | Gly 10 | Lys | Thr | Ile | Thr | Leu 15 | Glu |
|---|---|---|---|---|---|---|---|---|---|---|---|---|---|---|---|
| Val | Glu | Ser | Ser 20 | Asp | Thr | Ile | Asp | Asn 25 | Val | Lys | Ser | Lys | Ile 30 | Gln | Asp |
| Lys | Glu | Gly 35 | Ile | Pro | Pro | Asp | Gln 40 | Gln | Arg | Leu | Ile | Phe 45 | Ala | Gly | Lys |
| Gln | Leu 50 | Glu | Asp | Gly | Arg | Thr 55 | Leu | Ser | Asp | Tyr | Asn 60 | Ile | Gln | Lys | Glu |
| Ser 65 | Thr | Leu | His | Leu | Val 70 | Leu | Arg | Leu | Arg | Gly 75 | Gly | Met | His | Gly | Ser 80 |
| Gly | Ala | Trp | Leu | Leu 85 | Pro | Val | Ser | Leu | Val 90 | Lys | Arg | Lys | Thr | Thr 95 | Leu |
| Ala | Pro | Asn | Thr 100 | Gln | Thr | Ala | Ser | Pro 105 | Arg | Ala | Leu | Ala | Asp 110 | Ser | Leu |
| Met | Gln | Leu 115 | Ala | Arg | Gln | Val | Ser 120 | Arg | Leu | Asn | Arg | Leu 125 | Ala | Ala | His |
| Pro | Pro 130 | Phe | Ala | Ser | Trp | Arg 135 | Asn | Ser | Glu | Glu | Ala 140 | Arg | Thr | Asp | Arg |
| Pro 145 | Ser | Gln | Gln | Leu | Arg 150 | Ser | Leu | Asn | Gly | Glu 155 | Trp | Arg | Phe | Ala | Trp 160 |
| Phe | Pro | Ala | Pro | Glu 165 | Ala | Val | Pro | Glu | Ser 170 | Trp | Leu | Glu | Cys | Asp 175 | Leu |
| Pro | Glu | Ala | Asp 180 | Thr | Val | Val | Val | Pro 185 | Ser | Asn | Trp | Gln | Met 190 | His | Gly |
| Tyr | Asp | Ala 195 | Pro | Ile | Tyr | Thr | Asn 200 | Val | Thr | Tyr | Pro | Ile 205 | Thr | Val | Asn |
| Pro | Pro 210 | Phe | Val | Pro | Thr | Glu 215 | Asn | Pro | Thr | Gly | Cys 220 | Tyr | Ser | Leu | Thr |
| Phe 225 | Asn | Val | Asp | Glu | Ser 230 | Trp | Leu | Gln | Glu | Gly 235 | Gln | Thr | Arg | Ile | Ile 240 |
| Phe | Asp | Gly | Val | Asn 245 | Ser | Ala | Phe | His | Leu 250 | Trp | Cys | Asn | Gly | Arg 255 | Trp |
| Val | Gly | Tyr | Gly 260 | Gln | Asp | Ser | Arg | Leu 265 | Pro | Ser | Glu | Phe | Asp 270 | Leu | Ser |

```
Ala Phe Leu Arg Ala Gly Glu Asn Arg Leu Ala Val Met Val Leu Arg
        275                 280                 285
Trp Ser Asp Gly Ser Tyr Leu Glu Asp Gln Asp Met Trp Arg Met Ser
    290                 295                 300
Gly Ile Phe Arg Asp Val Ser Leu Leu His Lys Pro Thr Thr Gln Ile
305                     310                 315                 320
Ser Asp Phe His Val Ala Thr Arg Phe Asn Asp Asp Phe Ser Arg Ala
                325                 330                     335
Val Leu Glu Ala Glu Val Gln Met Cys Gly Glu Leu Arg Asp Tyr Leu
            340                 345                 350
Arg Val Thr Val Ser Leu Trp Gln Gly Glu Thr Gln Val Ala Ser Gly
        355                 360                 365
Thr Ala Pro Phe Gly Gly Glu Ile Ile Asp Glu Arg Gly Gly Tyr Ala
    370                 375                 380
Asp Arg Val Thr Leu Arg Leu Asn Val Glu Asn Pro Lys Leu Trp Ser
385                 390                 395                     400
Ala Glu Ile Pro Asn Leu Tyr Arg Ala Val Val Glu Leu His Thr Ala
                405                 410                 415
Asp Gly Thr Leu Ile Glu Ala Glu Ala Cys Asp Val Gly Phe Arg Glu
            420                 425                 430
Val Arg Ile Glu Asn Gly Leu Leu Leu Leu Asn Gly Lys Pro Leu Leu
        435                 440                 445
Ile Arg Gly Val Asn Arg His Glu His His Pro Leu His Gly Gln Val
    450                 455                 460
Met Asp Glu Gln Thr Met Val Gln Asp Ile Leu Leu Met Lys Gln Asn
465                 470                 475                     480
Asn Phe Asn Ala Val Arg Cys Ser His Tyr Pro Asn His Pro Leu Trp
                485                 490                 495
Tyr Thr Leu Cys Asp Arg Tyr Gly Leu Tyr Val Val Asp Glu Ala Asn
            500                 505                 510
Ile Glu Thr His Gly Met Val Pro Met Asn Arg Leu Thr Asp Asp Pro
        515                 520                 525
Arg Trp Leu Pro Ala Met Ser Glu Arg Val Thr Arg Met Val Gln Arg
    530                 535                 540
Asp Arg Asn His Pro Ser Val Ile Ile Trp Ser Leu Gly Asn Glu Ser
545                 550                 555                     560
Gly His Gly Ala Asn His Asp Ala Leu Tyr Arg Trp Ile Lys Ser Val
                565                 570                 575
Asp Pro Ser Arg Pro Val Gln Tyr Glu Gly Gly Gly Ala Asp Thr Thr
            580                 585                 590
Ala Thr Asp Ile Ile Cys Pro Met Tyr Ala Arg Val Asp Glu Asp Gln
        595                 600                 605
Pro Phe Pro Ala Val Pro Lys Trp Ser Ile Lys Lys Trp Leu Ser Leu
    610                 615                 620
Pro Gly Glu Thr Arg Pro Leu Ile Leu Cys Glu Tyr Ala His Ala Met
625                 630                 635                     640
Gly Asn Ser Leu Gly Gly Phe Ala Lys Tyr Trp Gln Ala Phe Arg Gln
                645                 650                 655
Tyr Pro Arg Leu Gln Gly Gly Phe Val Trp Asp Trp Val Asp Gln Ser
            660                 665                 670
Leu Ile Lys Tyr Asp Glu Asn Gly Asn Pro Trp Ser Ala Tyr Gly Gly
        675                 680                 685
Asp Phe Gly Asp Thr Pro Asn Asp Arg Gln Phe Cys Met Asn Gly Leu
    690                 695                 700
```

-continued

| | | | | | | | | | | | | | | | |
|---|---|---|---|---|---|---|---|---|---|---|---|---|---|---|---|
|Val|Phe|Ala|Asp|Arg|Thr|Pro|His|Pro|Ala|Leu|Thr|Glu|Ala|Lys|His|
|705| | | | |710| | | |715| | | | |720| |
|Gln|Gln|Gln|Phe|Phe|Gln|Phe|Arg|Leu|Ser|Gly|Gln|Thr|Ile|Glu|Val|
| | | | |725| | | |730| | | | |735| | |
|Thr|Ser|Glu|Tyr|Leu|Phe|Arg|His|Ser|Asp|Asn|Glu|Leu|Leu|His|Trp|
| | | |740| | | |745| | | | |750| | | |
|Met|Val|Ala|Leu|Asp|Gly|Lys|Pro|Leu|Ala|Ser|Gly|Glu|Val|Pro|Leu|
| | |755| | | |760| | | | |765| | | | |
|Asp|Val|Ala|Pro|Gln|Gly|Lys|Gln|Leu|Ile|Glu|Leu|Pro|Glu|Leu|Pro|
| |770| | | |775| | | |780| | | | | | |
|Gln|Pro|Glu|Ser|Ala|Gly|Gln|Leu|Trp|Leu|Thr|Val|Arg|Val|Val|Gln|
|785| | | | |790| | | |795| | | | | |800|
|Pro|Asn|Ala|Thr|Ala|Trp|Ser|Glu|Ala|Gly|His|Ile|Ser|Ala|Trp|Gln|
| | | | |805| | | |810| | | | |815| | |
|Gln|Trp|Arg|Leu|Ala|Glu|Asn|Leu|Ser|Val|Thr|Leu|Pro|Ala|Ala|Ser|
| | | |820| | | |825| | | | |830| | | |
|His|Ala|Ile|Pro|His|Leu|Thr|Thr|Ser|Glu|Met|Asp|Phe|Cys|Ile|Glu|
| | |835| | | |840| | | | |845| | | | |
|Leu|Gly|Asn|Lys|Arg|Trp|Gln|Phe|Asn|Arg|Gln|Ser|Gly|Phe|Leu|Ser|
| |850| | | | |855| | | |860| | | | | |
|Gln|Met|Trp|Ile|Gly|Asp|Lys|Lys|Gln|Leu|Leu|Thr|Pro|Leu|Arg|Asp|
|865| | | | |870| | | |875| | | | | |880|
|Gln|Phe|Thr|Arg|Ala|Pro|Leu|Asp|Asn|Asp|Ile|Gly|Val|Ser|Glu|Ala|
| | | | |885| | | |890| | | | |895| | |
|Thr|Arg|Ile|Asp|Pro|Asn|Ala|Trp|Val|Glu|Arg|Trp|Lys|Ala|Ala|Gly|
| | | |900| | | |905| | | | |910| | | |
|His|Tyr|Gln|Ala|Glu|Ala|Ala|Leu|Leu|Gln|Cys|Thr|Ala|Asp|Thr|Leu|
| | |915| | | |920| | | | |925| | | | |
|Ala|Asp|Ala|Val|Leu|Ile|Thr|Thr|Ala|His|Ala|Trp|Gln|His|Gln|Gly|
| |930| | | | |935| | | | |940| | | | |
|Lys|Thr|Leu|Phe|Ile|Ser|Arg|Lys|Thr|Tyr|Arg|Ile|Asp|Gly|Ser|Gly|
|945| | | | |950| | | |955| | | | | |960|
|Gln|Met|Ala|Ile|Thr|Val|Asp|Val|Glu|Val|Ala|Ser|Asp|Thr|Pro|His|
| | | | |965| | | |970| | | | |975| | |
|Pro|Ala|Arg|Ile|Gly|Leu|Asn|Cys|Gln|Leu|Ala|Gln|Val|Ala|Glu|Arg|
| | |980| | | |985| | | | |990| | | | |
|Val|Asn|Trp|Leu|Gly|Leu|Gly|Pro|Gln|Glu|Asn|Tyr|Pro|Asp|Arg|Leu|
| | |995| | | |1000| | | | |1005| | | | |
|Thr|Ala|Ala|Cys|Phe|Asp|Arg|Trp|Asp|Leu|Pro|Leu|Ser|Asp|Met|Tyr|
| | |1010| | | |1015| | | |1020| | | | | |
|Thr|Pro|Tyr|Val|Phe|Pro|Ser|Glu|Asn|Gly|Leu|Arg|Cys|Gly|Thr|Arg|
|1025| | | | |1030| | | |1035| | | | | |1040|
|Glu|Leu|Asn|Tyr|Gly|Pro|His|Gln|Trp|Arg|Gly|Asp|Phe|Gln|Phe|Asn|
| | | |1045| | | |1050| | | | |1055| | | |
|Ile|Ser|Arg|Tyr|Ser|Gln|Gln|Gln|Leu|Met|Glu|Thr|Ser|His|Arg|His|
| | |1060| | | |1065| | | | |1070| | | | |
|Leu|Leu|His|Ala|Glu|Glu|Gly|Thr|Trp|Leu|Asn|Ile|Asp|Gly|Phe|His|
| |1075| | | | |1080| | | | |1085| | | | |
|Met|Gly|Ile|Gly|Gly|Asp|Asp|Ser|Trp|Ser|Pro|Ser|Val|Ser|Ala|Glu|
| |1090| | | |1095| | | | |1100| | | | | |
|Phe|Gln|Leu|Ser|Ala|Gly|Arg|Tyr|His|Tyr|Gln|Leu|Val|Trp|Cys|Gln|
|1105| | | | |1110| | | |1115| | | | | |1120|
|Lys| | | | | | | | | | | | | | | |

( 2 ) INFORMATION FOR SEQ ID NO:3:

( i ) SEQUENCE CHARACTERISTICS:
    ( A ) LENGTH: 2845 base pairs
    ( B ) TYPE: nucleic acid
    ( C ) STRANDEDNESS: double
    ( D ) TOPOLOGY: linear ( i x ) FEATURE:
    ( A ) NAME/KEY: CDS
    ( B ) LOCATION: 193..2619

( x i ) SEQUENCE DESCRIPTION: SEQ ID NO:3:

```
TGTGATCTGC GTCCTTTTTT TCTCAGGAAA AAAAAATTTT ATAGACATTC AAAGAATAGA        60

AGCGATTGTC AAAATTCGCT TCTCCTTTCT TTTCCATTAT AACGTCTGAT CATTTTACGT       120

CTTCAGTGCC CTCCCTTGTT CGAAACTAGA TACTTTCGAA CACTTCTCCC CTTTTAATCT       180

ACAAAATTTT GT ATG GAT TTG TTT ATT GAA AGC AAG ATA AAC AGT TTA          228
              Met Asp Leu Phe Ile Glu Ser Lys Ile Asn Ser Leu
                1               5                  10

TTA CAA TTT TTA TTT GGT TCC CGA CAG GAT TTT TTG AGA AAT TTT AAA        276
Leu Gln Phe Leu Phe Gly Ser Arg Gln Asp Phe Leu Arg Asn Phe Lys
         15                  20                  25

ACT TGG AGT AAC AAC AAT AAC AAT CTA TCG ATT TAT TTA TTA ATT TTT        324
Thr Trp Ser Asn Asn Asn Asn Asn Leu Ser Ile Tyr Leu Leu Ile Phe
     30                  35                  40

GGC ATA GTA GTA TTT TTT TAT AAA AAA CCA GAC CAT CTA AAC TAC ATT        372
Gly Ile Val Val Phe Phe Tyr Lys Lys Pro Asp His Leu Asn Tyr Ile
45                  50                  55                  60

GTT GAG AGC GTT AGT GAA ATG ACA ACA AAC TTC AGA AAT AAT AAT AGC        420
Val Glu Ser Val Ser Glu Met Thr Thr Asn Phe Arg Asn Asn Asn Ser
                 65                  70                  75

CTT AGC CGT TGG TTG CCC AGA AGT AAG TTT ACC CAC TTA GAC GAA GAG        468
Leu Ser Arg Trp Leu Pro Arg Ser Lys Phe Thr His Leu Asp Glu Glu
             80                  85                  90

ATC TTG AAA AGA GGT GGT TTC ATT GCT GGT TTA GTT AAT GAT GGT AAC        516
Ile Leu Lys Arg Gly Gly Phe Ile Ala Gly Leu Val Asn Asp Gly Asn
         95                 100                 105

ACT TGT TTT ATG AAC TCT GTT TTG CAA TCA TTG GCA TCA TCC AGA GAA        564
Thr Cys Phe Met Asn Ser Val Leu Gln Ser Leu Ala Ser Ser Arg Glu
    110                 115                 120

TTA ATG GAG TTC TTG GAC AAT AAT GTC ATA AGG ACC TAT GAG GAG ATA        612
Leu Met Glu Phe Leu Asp Asn Asn Val Ile Arg Thr Tyr Glu Glu Ile
125                 130                 135                 140

GAA CAA AAT GAA CAC AAT GAA GAA GGA AAC GGG CAA GAA TCT GCT CAA        660
Glu Gln Asn Glu His Asn Glu Glu Gly Asn Gly Gln Glu Ser Ala Gln
                145                 150                 155

GAT GAA GCC ACT CAT AAG AAA AAC ACT CGT AAG GGT GGC AAA GTT TAT        708
Asp Glu Ala Thr His Lys Lys Asn Thr Arg Lys Gly Gly Lys Val Tyr
            160                 165                 170

GGT AAG CAT AAG AAG AAA TTG AAT AGG AAG TCA AGT TCG AAA GAA GAC        756
Gly Lys His Lys Lys Lys Leu Asn Arg Lys Ser Ser Ser Lys Glu Asp
        175                 180                 185

GAA GAA AAG AGC CAG GAG CCA GAT ATC ACT TTC AGT GTC GCC TTA AGG        804
Glu Glu Lys Ser Gln Glu Pro Asp Ile Thr Phe Ser Val Ala Leu Arg
    190                 195                 200

GAT CTA CTT TCT GCC TTA AAT GCG AAG TAT TAT CGG GAT AAA CCC TAT       852
Asp Leu Leu Ser Ala Leu Asn Ala Lys Tyr Tyr Arg Asp Lys Pro Tyr
205                 210                 215                 220

TTC AAA ACC AAT AGT TTA TTG AAA GCA ATG TCC AAA TCT CCA AGA AAA        900
Phe Lys Thr Asn Ser Leu Leu Lys Ala Met Ser Lys Ser Pro Arg Lys
                225                 230                 235

AAT ATT CTT CTT GGC TAC GAC CAA GAG GAC GCG CAA GAA TTC TTC CAG        948
Asn Ile Leu Leu Gly Tyr Asp Gln Glu Asp Ala Gln Glu Phe Phe Gln
            240                 245                 250
```

| | | | | | | | | | | | | | | | | |
|---|---|---|---|---|---|---|---|---|---|---|---|---|---|---|---|---|
| AAC | ATA | CTA | GCC | GAG | TTG | GAA | AGT | AAC | GTT | AAA | TCA | TTG | AAT | ACT | GAA | 996 |
| Asn | Ile | Leu | Ala | Glu | Leu | Glu | Ser | Asn | Val | Lys | Ser | Leu | Asn | Thr | Glu | |
| | | 255 | | | | | 260 | | | | | 265 | | | | |
| AAA | CTA | GAT | ACC | ACT | CCA | GTT | GCG | AAA | TCA | GAA | TTA | CCC | GAT | GAT | GCT | 1044 |
| Lys | Leu | Asp | Thr | Thr | Pro | Val | Ala | Lys | Ser | Glu | Leu | Pro | Asp | Asp | Ala | |
| 270 | | | | | 275 | | | | | 280 | | | | | | |
| TTA | GTA | GGT | CAA | CTT | AAC | CTT | GGT | GAA | GTT | GGC | ACT | GTT | TAC | ATT | CCA | 1092 |
| Leu | Val | Gly | Gln | Leu | Asn | Leu | Gly | Glu | Val | Gly | Thr | Val | Tyr | Ile | Pro | |
| 285 | | | | | 290 | | | | | 295 | | | | | 300 | |
| ACT | GAA | CAG | ATT | GAT | CCT | AAC | TCT | ATA | CTA | CAT | GAC | AAG | TCC | ATT | CAA | 1140 |
| Thr | Glu | Gln | Ile | Asp | Pro | Asn | Ser | Ile | Leu | His | Asp | Lys | Ser | Ile | Gln | |
| | | | | 305 | | | | | 310 | | | | | 315 | | |
| AAT | TTC | ACA | CCT | TTC | AAA | CTA | ATG | ACT | CCT | TTA | GAT | GGT | ATC | ACG | GCA | 1188 |
| Asn | Phe | Thr | Pro | Phe | Lys | Leu | Met | Thr | Pro | Leu | Asp | Gly | Ile | Thr | Ala | |
| | | | 320 | | | | | 325 | | | | | 330 | | | |
| GAA | AGA | ATT | GGT | TGT | TTA | CAG | TGT | GGT | GAG | AAC | GGT | GGC | ATA | AGA | TAT | 1236 |
| Glu | Arg | Ile | Gly | Cys | Leu | Gln | Cys | Gly | Glu | Asn | Gly | Gly | Ile | Arg | Tyr | |
| | | 335 | | | | | 340 | | | | | 345 | | | | |
| TCC | GTA | TTT | TCG | GGA | TTA | AGC | TTA | AAT | TTA | CCG | AAC | GAG | AAT | ATT | GGT | 1284 |
| Ser | Val | Phe | Ser | Gly | Leu | Ser | Leu | Asn | Leu | Pro | Asn | Glu | Asn | Ile | Gly | |
| | 350 | | | | | 355 | | | | | 360 | | | | | |
| TCC | ACT | TTA | AAA | TTA | TCT | CAG | TTA | TTA | AGC | GAC | TGG | AGT | AAA | CCT | GAA | 1332 |
| Ser | Thr | Leu | Lys | Leu | Ser | Gln | Leu | Leu | Ser | Asp | Trp | Ser | Lys | Pro | Glu | |
| 365 | | | | | 370 | | | | | 375 | | | | | 380 | |
| ATC | ATC | GAA | GGC | GTA | GAA | TGT | AAC | CGT | TGT | GCC | CTC | ACA | GCA | GCG | CAC | 1380 |
| Ile | Ile | Glu | Gly | Val | Glu | Cys | Asn | Arg | Cys | Ala | Leu | Thr | Ala | Ala | His | |
| | | | | 385 | | | | | 390 | | | | | 395 | | |
| TCT | CAT | TTA | TTT | GGT | CAG | TTG | AAA | GAA | TTT | GAA | AAA | AAA | CCT | GAG | GGT | 1428 |
| Ser | His | Leu | Phe | Gly | Gln | Leu | Lys | Glu | Phe | Glu | Lys | Lys | Pro | Glu | Gly | |
| | | | 400 | | | | | 405 | | | | | 410 | | | |
| TCG | ATC | CCA | GAA | AAG | CCA | ATT | AAC | GCT | GTA | AAA | GAT | AGG | GTC | CAT | CAA | 1476 |
| Ser | Ile | Pro | Glu | Lys | Pro | Ile | Asn | Ala | Val | Lys | Asp | Arg | Val | His | Gln | |
| | | 415 | | | | | 420 | | | | | 425 | | | | |
| ATC | GAA | GAA | GTT | CTT | GCC | AAA | CCA | GTT | ATT | GAC | GAT | GAA | GAT | TAT | AAG | 1524 |
| Ile | Glu | Glu | Val | Leu | Ala | Lys | Pro | Val | Ile | Asp | Asp | Glu | Asp | Tyr | Lys | |
| | 430 | | | | | 435 | | | | | 440 | | | | | |
| AAG | TTG | CAT | ACA | GCA | AAT | ATG | GTA | CGT | AAA | TGC | TCT | AAA | TCT | AAG | CAG | 1572 |
| Lys | Leu | His | Thr | Ala | Asn | Met | Val | Arg | Lys | Cys | Ser | Lys | Ser | Lys | Gln | |
| 445 | | | | | 450 | | | | | 455 | | | | | 460 | |
| ATT | TTA | ATA | TCA | AGA | CCT | CCA | CCA | TTA | TTA | TCC | ATT | CAT | ATC | AAC | AGA | 1620 |
| Ile | Leu | Ile | Ser | Arg | Pro | Pro | Pro | Leu | Leu | Ser | Ile | His | Ile | Asn | Arg | |
| | | | | 465 | | | | | 470 | | | | | 475 | | |
| TCC | GTA | TTT | GAT | CCA | AGA | ACG | TAC | ATG | ATT | AGA | AAA | AAT | AAC | TCG | AAA | 1668 |
| Ser | Val | Phe | Asp | Pro | Arg | Thr | Tyr | Met | Ile | Arg | Lys | Asn | Asn | Ser | Lys | |
| | | | 480 | | | | | 485 | | | | | 490 | | | |
| GTA | TTG | TTT | AAG | TCA | AGG | TTG | AAT | CTT | GCC | CCA | TGG | TGT | TGT | GAT | ATT | 1716 |
| Val | Leu | Phe | Lys | Ser | Arg | Leu | Asn | Leu | Ala | Pro | Trp | Cys | Cys | Asp | Ile | |
| | | 495 | | | | | 500 | | | | | 505 | | | | |
| AAT | GAA | ATC | AAT | TTG | GAT | GCT | CGT | TTG | CCA | ATG | TCA | AAA | AAG | GAA | AAA | 1764 |
| Asn | Glu | Ile | Asn | Leu | Asp | Ala | Arg | Leu | Pro | Met | Ser | Lys | Lys | Glu | Lys | |
| | 510 | | | | | 515 | | | | | 520 | | | | | |
| GCT | GCG | CAA | CAA | GAT | TCA | AGT | GAA | GAT | GAA | AAC | ATT | GGC | GGT | GAA | TAC | 1812 |
| Ala | Ala | Gln | Gln | Asp | Ser | Ser | Glu | Asp | Glu | Asn | Ile | Gly | Gly | Glu | Tyr | |
| 525 | | | | | 530 | | | | | 535 | | | | | 540 | |
| TAT | ACG | AAA | TTA | CAT | GAA | CGC | TTC | GAG | CAG | GAA | TTT | GAA | GAC | AGC | GAG | 1860 |
| Tyr | Thr | Lys | Leu | His | Glu | Arg | Phe | Glu | Gln | Glu | Phe | Glu | Asp | Ser | Glu | |
| | | | | 545 | | | | | 550 | | | | | 555 | | |
| GAA | GAA | AAA | GAA | TAC | GAT | GAC | GCA | GAG | GGG | AAC | TAT | GCG | TCT | CAT | TAC | 1908 |
| Glu | Glu | Lys | Glu | Tyr | Asp | Asp | Ala | Glu | Gly | Asn | Tyr | Ala | Ser | His | Tyr | |
| | | | 560 | | | | | 565 | | | | | 570 | | | |
| AAT | CAT | ACC | AAG | GAT | ATC | AGT | AAC | TAT | GAT | CCC | CTA | AAC | GGT | GAA | GTC | 1956 |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Asn | His | Thr | Lys | Asp | Ile | Ser | Asn | Tyr | Asp | Pro | Leu | Asn | Gly | Glu | Val |      |
|     | 575 |     |     |     | 580 |     |     |     |     |     | 585 |     |     |     |     |      |
| GAT | GGC | GTG | ACA | TCC | GAT | GAT | GAA | GAT | GAG | TAC | ATT | GAA | GAA | ACC | GAT | 2004 |
| Asp | Gly | Val | Thr | Ser | Asp | Asp | Glu | Asp | Glu | Tyr | Ile | Glu | Glu | Thr | Asp |      |
|     | 590 |     |     |     | 595 |     |     |     |     | 600 |     |     |     |     |     |      |
| GCT | TTA | GGG | AAT | ACA | ATC | AAA | AAA | AGG | ATC | ATA | GAA | CAT | TCT | GAT | GTT | 2052 |
| Ala | Leu | Gly | Asn | Thr | Ile | Lys | Lys | Arg | Ile | Ile | Glu | His | Ser | Asp | Val |      |
| 605 |     |     |     |     | 610 |     |     |     |     | 615 |     |     |     |     | 620 |      |
| GAA | AAC | GAG | AAT | GTA | AAA | GAT | AAT | GAA | GAA | CTG | CAA | GAA | ATC | GAC | AAT | 2100 |
| Glu | Asn | Glu | Asn | Val | Lys | Asp | Asn | Glu | Glu | Leu | Gln | Glu | Ile | Asp | Asn |      |
|     |     |     |     | 625 |     |     |     |     | 630 |     |     |     |     | 635 |     |      |
| GTG | AGC | CTT | GAC | GAA | CCA | AAG | ATC | AAT | GTT | GAA | GAT | CAA | CTA | GAA | ACA | 2148 |
| Val | Ser | Leu | Asp | Glu | Pro | Lys | Ile | Asn | Val | Glu | Asp | Gln | Leu | Glu | Thr |      |
|     |     |     | 640 |     |     |     |     | 645 |     |     |     |     | 650 |     |     |      |
| TCA | TCT | GAT | GAG | GAA | GAT | GTT | ATA | CCA | GCT | CCA | CCT | ATC | AAT | TAT | GCT | 2196 |
| Ser | Ser | Asp | Glu | Glu | Asp | Val | Ile | Pro | Ala | Pro | Pro | Ile | Asn | Tyr | Ala |      |
|     |     | 655 |     |     |     |     | 660 |     |     |     |     |     | 665 |     |     |      |
| AGG | TCA | TTT | TCC | ACA | GTT | CCA | GCC | ACT | CCA | TTG | ACA | TAT | TCA | TTG | CGC | 2244 |
| Arg | Ser | Phe | Ser | Thr | Val | Pro | Ala | Thr | Pro | Leu | Thr | Tyr | Ser | Leu | Arg |      |
|     | 670 |     |     |     |     | 675 |     |     |     |     | 680 |     |     |     |     |      |
| TCT | GTC | ATT | GTT | CAC | TAC | GGT | ACC | CAT | AAT | TAT | GGT | CAT | TAC | ATT | GCA | 2292 |
| Ser | Val | Ile | Val | His | Tyr | Gly | Thr | His | Asn | Tyr | Gly | His | Tyr | Ile | Ala |      |
| 685 |     |     |     |     | 690 |     |     |     |     | 695 |     |     |     |     | 700 |      |
| TTT | AGA | AAA | TAC | AGG | GGT | TGT | TGG | TGG | AGA | ATA | TCT | GAT | GAG | ACT | GTG | 2340 |
| Phe | Arg | Lys | Tyr | Arg | Gly | Cys | Trp | Trp | Arg | Ile | Ser | Asp | Glu | Thr | Val |      |
|     |     |     |     | 705 |     |     |     |     | 710 |     |     |     |     | 715 |     |      |
| TAC | GTT | GTG | GAC | GAA | GCT | GAA | GTC | CTT | TCA | ACA | CCC | GGT | GTA | TTT | ATG | 2388 |
| Tyr | Val | Val | Asp | Glu | Ala | Glu | Val | Leu | Ser | Thr | Pro | Gly | Val | Phe | Met |      |
|     |     |     | 720 |     |     |     |     | 725 |     |     |     |     | 730 |     |     |      |
| TTA | TTT | TAC | GAA | TAT | GAC | TTT | GAT | GAA | GAA | ACT | GGG | AAG | ATG | AAG | GAT | 2436 |
| Leu | Phe | Tyr | Glu | Tyr | Asp | Phe | Asp | Glu | Glu | Thr | Gly | Lys | Met | Lys | Asp |      |
|     |     | 735 |     |     |     |     | 740 |     |     |     |     | 745 |     |     |     |      |
| GAT | TTG | GAA | GCT | ATT | CAG | AGT | AAT | AAT | GAA | GAA | GAT | GAT | GAA | AAA | GAG | 2484 |
| Asp | Leu | Glu | Ala | Ile | Gln | Ser | Asn | Asn | Glu | Glu | Asp | Asp | Glu | Lys | Glu |      |
|     | 750 |     |     |     |     | 755 |     |     |     |     | 760 |     |     |     |     |      |
| CAG | GAG | CAA | AAA | GGA | GTC | CAG | GAG | CCA | AAG | GAA | AGC | CAA | GAG | CAA | GGA | 2532 |
| Gln | Glu | Gln | Lys | Gly | Val | Gln | Glu | Pro | Lys | Glu | Ser | Gln | Glu | Gln | Gly |      |
| 765 |     |     |     |     | 770 |     |     |     |     | 775 |     |     |     |     | 780 |      |
| GAA | GGT | GAA | GAG | CAA | GAG | GAA | GGT | CAA | GAG | CAG | ATG | AAG | TTC | GAG | AGA | 2580 |
| Glu | Gly | Glu | Glu | Gln | Glu | Glu | Gly | Gln | Glu | Gln | Met | Lys | Phe | Glu | Arg |      |
|     |     |     |     | 785 |     |     |     |     | 790 |     |     |     |     | 795 |     |      |
| ACA | GAA | GAC | CAT | AGA | GAT | ATT | TCT | GGT | AAA | GAT | GTA | AAC | TAAGTTATAA |     |     | 2629 |
| Thr | Glu | Asp | His | Arg | Asp | Ile | Ser | Gly | Lys | Asp | Val | Asn |     |     |     |      |
|     |     |     | 800 |     |     |     |     | 805 |     |     |     |     |     |     |     |      |

ATACGATATC CGTAATTGTG TAAATAACAA TAACTATAAT TAAATTGAAT AATTAAAAGT 2689

CTACGTTATT CGTTAAATCA ATTGTTTAGC TAGTTACGAA TGTCTAAAGT TTTTGTAGGA 2749

CAATTGCAAA AATCACTTCC ATTATTATAC AAATCCTTCT AAGCTTCATT TTTCTTACCA 2809

TTGTACTTCT TCAACTTTTT CTCTTCTCTT CTCTCC 2845

( 2 ) INFORMATION FOR SEQ ID NO:4:

( i ) SEQUENCE CHARACTERISTICS:
        ( A ) LENGTH: 809 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Asp | Leu | Phe | Ile | Glu | Ser | Lys | Ile | Asn | Ser | Leu | Leu | Gln | Phe | Leu |
| 1   |     |     |     | 5   |     |     |     |     | 10  |     |     |     |     | 15  |     |

| | | | | | | | | | | | | | | |
|---|---|---|---|---|---|---|---|---|---|---|---|---|---|---|
|Phe|Gly|Ser|Arg<br>20|Gln|Asp|Phe|Leu|Arg|Asn<br>25|Phe|Lys|Thr|Trp<br>30|Ser|Asn|
|Asn|Asn|Asn<br>35|Asn|Leu|Ser|Ile|Tyr<br>40|Leu|Leu|Ile|Phe|Gly<br>45|Ile|Val|Val|
|Phe|Phe<br>50|Tyr|Lys|Lys|Pro|Asp<br>55|His|Leu|Asn|Tyr|Ile<br>60|Val|Glu|Ser|Val|
|Ser<br>65|Glu|Met|Thr|Thr|Asn<br>70|Phe|Arg|Asn|Asn|Asn<br>75|Ser|Leu|Ser|Arg|Trp<br>80|
|Leu|Pro|Arg|Ser|Lys<br>85|Phe|Thr|His|Leu|Asp<br>90|Glu|Glu|Ile|Leu|Lys<br>95|Arg|
|Gly|Gly|Phe|Ile<br>100|Ala|Gly|Leu|Val|Asn<br>105|Asp|Gly|Asn|Thr|Cys<br>110|Phe|Met|
|Asn|Ser|Val<br>115|Leu|Gln|Ser|Leu|Ala<br>120|Ser|Ser|Arg|Glu|Leu<br>125|Met|Glu|Phe|
|Leu|Asp<br>130|Asn|Asn|Val|Ile|Arg<br>135|Thr|Tyr|Glu|Glu|Ile<br>140|Glu|Gln|Asn|Glu|
|His<br>145|Asn|Glu|Glu|Gly|Asn<br>150|Gly|Gln|Glu|Ser|Ala<br>155|Gln|Asp|Glu|Ala|Thr<br>160|
|His|Lys|Lys|Asn|Thr<br>165|Arg|Lys|Gly|Gly|Lys<br>170|Val|Tyr|Gly|Lys|His<br>175|Lys|
|Lys|Lys|Leu|Asn<br>180|Arg|Lys|Ser|Ser|Ser<br>185|Lys|Glu|Asp|Glu|Glu<br>190|Lys|Ser|
|Gln|Glu|Pro<br>195|Asp|Ile|Thr|Phe|Ser<br>200|Val|Ala|Leu|Arg|Asp<br>205|Leu|Leu|Ser|
|Ala|Leu<br>210|Asn|Ala|Lys|Tyr|Tyr<br>215|Arg|Asp|Lys|Pro|Tyr<br>220|Phe|Lys|Thr|Asn|
|Ser<br>225|Leu|Leu|Lys|Ala|Met<br>230|Ser|Lys|Ser|Pro|Arg<br>235|Lys|Asn|Ile|Leu|Leu<br>240|
|Gly|Tyr|Asp|Gln|Glu<br>245|Asp|Ala|Gln|Glu|Phe<br>250|Phe|Gln|Asn|Ile|Leu<br>255|Ala|
|Glu|Leu|Glu|Ser<br>260|Asn|Val|Lys|Ser|Leu<br>265|Asn|Thr|Glu|Lys|Leu<br>270|Asp|Thr|
|Thr|Pro|Val<br>275|Ala|Lys|Ser|Glu|Leu<br>280|Pro|Asp|Asp|Ala|Leu<br>285|Val|Gly|Gln|
|Leu|Asn<br>290|Leu|Gly|Glu|Val|Gly<br>295|Thr|Val|Tyr|Ile|Pro<br>300|Thr|Glu|Gln|Ile|
|Asp<br>305|Pro|Asn|Ser|Ile|Leu<br>310|His|Asp|Lys|Ser|Ile<br>315|Gln|Asn|Phe|Thr|Pro<br>320|
|Phe|Lys|Leu|Met|Thr<br>325|Pro|Leu|Asp|Gly|Ile<br>330|Thr|Ala|Glu|Arg|Ile<br>335|Gly|
|Cys|Leu|Gln|Cys<br>340|Gly|Glu|Asn|Gly|Gly<br>345|Ile|Arg|Tyr|Ser|Val<br>350|Phe|Ser|
|Gly|Leu|Ser<br>355|Leu|Asn|Leu|Pro|Asn<br>360|Glu|Asn|Ile|Gly|Ser<br>365|Thr|Leu|Lys|
|Leu|Ser<br>370|Gln|Leu|Leu|Ser|Asp<br>375|Trp|Ser|Lys|Pro|Glu<br>380|Ile|Ile|Glu|Gly|
|Val<br>385|Glu|Cys|Asn|Arg|Cys<br>390|Ala|Leu|Thr|Ala|Ala<br>395|His|Ser|His|Leu|Phe<br>400|
|Gly|Gln|Leu|Lys|Glu<br>405|Phe|Glu|Lys|Lys|Pro<br>410|Glu|Gly|Ser|Ile|Pro<br>415|Glu|
|Lys|Pro|Ile|Asn<br>420|Ala|Val|Lys|Asp|Arg<br>425|Val|His|Gln|Ile|Glu<br>430|Glu|Val|
|Leu|Ala|Lys|Pro<br>435|Val|Ile|Asp|Asp|Glu<br>440|Asp|Tyr|Lys|Lys<br>445|Leu|His|Thr|
|Ala|Asn|Met|Val|Arg|Lys|Cys|Ser|Lys|Ser|Lys|Gln|Ile|Leu|Ile|Ser|

|       |     |     |     | 450 |     |     |     |     |     | 455 |     |     |     |     |     | 460 |     |     |     |
|-------|-----|-----|-----|-----|-----|-----|-----|-----|-----|-----|-----|-----|-----|-----|-----|-----|-----|-----|-----|

Arg Pro Pro Pro Leu Leu Ser Ile His Ile Asn Arg Ser Val Phe Asp
465             470             475             480

Pro Arg Thr Tyr Met Ile Arg Lys Asn Asn Ser Lys Val Leu Phe Lys
            485             490             495

Ser Arg Leu Asn Leu Ala Pro Trp Cys Cys Asp Ile Asn Glu Ile Asn
        500             505             510

Leu Asp Ala Arg Leu Pro Met Ser Lys Lys Glu Lys Ala Ala Gln Gln
        515             520             525

Asp Ser Ser Glu Asp Glu Asn Ile Gly Gly Glu Tyr Tyr Thr Lys Leu
        530             535             540

His Glu Arg Phe Glu Gln Glu Phe Glu Asp Ser Glu Glu Glu Lys Glu
545             550             555             560

Tyr Asp Asp Ala Glu Gly Asn Tyr Ala Ser His Tyr Asn His Thr Lys
                565             570             575

Asp Ile Ser Asn Tyr Asp Pro Leu Asn Gly Glu Val Asp Gly Val Thr
            580             585             590

Ser Asp Asp Glu Asp Glu Tyr Ile Glu Glu Thr Asp Ala Leu Gly Asn
        595             600             605

Thr Ile Lys Lys Arg Ile Ile Glu His Ser Asp Val Glu Asn Glu Asn
    610             615             620

Val Lys Asp Asn Glu Glu Leu Gln Glu Ile Asp Asn Val Ser Leu Asp
625             630             635             640

Glu Pro Lys Ile Asn Val Glu Asp Gln Leu Glu Thr Ser Ser Asp Glu
                645             650             655

Glu Asp Val Ile Pro Ala Pro Pro Ile Asn Tyr Ala Arg Ser Phe Ser
            660             665             670

Thr Val Pro Ala Thr Pro Leu Thr Tyr Ser Leu Arg Ser Val Ile Val
        675             680             685

His Tyr Gly Thr His Asn Tyr Gly His Tyr Ile Ala Phe Arg Lys Tyr
    690             695             700

Arg Gly Cys Trp Trp Arg Ile Ser Asp Glu Thr Val Tyr Val Val Asp
705             710             715             720

Glu Ala Glu Val Leu Ser Thr Pro Gly Val Phe Met Leu Phe Tyr Glu
            725             730             735

Tyr Asp Phe Asp Glu Glu Thr Gly Lys Met Lys Asp Asp Leu Glu Ala
        740             745             750

Ile Gln Ser Asn Asn Glu Glu Asp Asp Glu Lys Glu Gln Glu Gln Lys
        755             760             765

Gly Val Gln Glu Pro Lys Glu Ser Gln Glu Gln Gly Glu Gly Glu Glu
    770             775             780

Gln Glu Glu Gly Gln Glu Gln Met Lys Phe Glu Arg Thr Glu Asp His
785             790             795             800

Arg Asp Ile Ser Gly Lys Asp Val Asn
            805

( 2 ) INFORMATION FOR SEQ ID NO:5:

( i ) SEQUENCE CHARACTERISTICS:
        ( A ) LENGTH: 6008 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 983..4774

( x i ) SEQUENCE DESCRIPTION: SEQ ID NO:5:

| | | | | | |
|---|---|---|---|---|---|
| GCATGCTCCC | AAGTGTCAGA | ATTTATCAGA | TGCTCAGGCT | GCATTTTTGG | ACCGTGTTAT | 60 |
| TCGTGTAGAT | CAAGCTGGCG | AATTAGGTGC | AGACTACATC | TACGCTGGCC | AGTACTTCGT | 120 |
| GTTGGCTCAT | AGGTACCCTC | ACTTGAAACC | TGTGCTAAAG | CACATATGGG | ACCAGGAGAT | 180 |
| ACATCATCAT | AATACTTTTA | ACAATTTGCA | ATTGAAAAGG | AGAGTCAGGC | CTTCCTTATT | 240 |
| AACGCCTTTG | TGGAAGGCAG | GAGCCTTTGC | AATGGGGGCT | GGTACCGCAT | TGATTTCTCC | 300 |
| AGAAGCAGCT | ATGGCTTGTA | CTGAAGCTGT | CGAGACAGTA | ATCGGAGGGC | ACTACAATGG | 360 |
| CCAATTGCGA | AACTTGGCCA | ATCAATTCAA | TTTAGAAAGA | ACAGATGGAA | CAAAGGGTCC | 420 |
| AAGTGAGGAA | ATCAAATCCT | TAACTTCTAC | TATCCAACAG | TTCAGGGATG | ACGAGCTAGA | 480 |
| GCATCTAGAC | ACCGCTATCA | AGCATGATTC | GTATATGGCA | GTTCCATATA | CAGTTATCAC | 540 |
| TGAAGGTATT | AAAACGATTT | GCAGAGTAGC | TATATGGAGT | GCCGAAAGAA | TTTAACCACC | 600 |
| AGAAAGTGGC | ATACATCAGT | CGCGTTATGC | CAGAAAAGGA | GAATTGAAAG | GAAAACGGTT | 660 |
| TGATAAATGT | CCTAATTAAA | CTATCATGTA | TAAAATTATG | TATCATCCTT | ACGCATTTTA | 720 |
| ACGCTATATG | ACCAATATGA | CAGGAATAGA | TACACTGTCT | ATAATTATGT | AAATGGGGTA | 780 |
| TGGGTTCATA | GTCTAAGGGT | GAGTACAAAC | TGGATCTTTA | ACAAGAGTAA | CAGTTAATTA | 840 |
| GAGCAAAACT | ATAGTACATA | TAGCTTGAAA | AAAACAAGCG | GCTTGCCATT | GGAAGAACAT | 900 |
| TGCATAAAAA | CGGGGCCACT | GCTAATAATA | AAGTGGTAAT | TAAAAGAAA | GCTTTTGTTC | 960 |

| | | | | | |
|---|---|---|---|---|---|
| AAGGTTAAGA | AGGTATAAGG | AA ATG CCG | AAC GAA GAT | AAT GAA CTT | CAA AAA | 1012 |
| | | Met Pro | Asn Glu Asp | Asn Glu Leu | Gln Lys |
| | | 1 | 5 | | 10 |

| | | | | | | | | | | | | | | | | |
|---|---|---|---|---|---|---|---|---|---|---|---|---|---|---|---|---|
| GCA | ATT | GAG | AAC | CAT | CAT | AAT | CAA | CTA | CTA | AAC | CAG | GAT | AAA | GAA | AAT | 1060 |
| Ala | Ile | Glu | Asn | His | His | Asn | Gln | Leu | Leu | Asn | Gln | Asp | Lys | Glu | Asn | |
| | | | | 15 | | | | 20 | | | | | 25 | | | |
| GCT | GAC | AGA | AAT | GGG | TCT | GTT | ATA | GAA | GAC | CTC | CCA | TTA | TAC | GGG | ACA | 1108 |
| Ala | Asp | Arg | Asn | Gly | Ser | Val | Ile | Glu | Asp | Leu | Pro | Leu | Tyr | Gly | Thr | |
| | | 30 | | | | | 35 | | | | | 40 | | | | |
| AGT | ATA | AAC | CAG | CAG | TCT | ACC | CCT | GGA | GAT | GTT | GAC | GAT | GGA | AAA | CAC | 1156 |
| Ser | Ile | Asn | Gln | Gln | Ser | Thr | Pro | Gly | Asp | Val | Asp | Asp | Gly | Lys | His | |
| | | 45 | | | | 50 | | | | | 55 | | | | | |
| TTA | CTG | TAT | CCA | GAT | ATT | GCC | ACC | AAC | CTA | CCA | CTG | AAG | ACT | TCT | GAC | 1204 |
| Leu | Leu | Tyr | Pro | Asp | Ile | Ala | Thr | Asn | Leu | Pro | Leu | Lys | Thr | Ser | Asp | |
| | 60 | | | | 65 | | | | | 70 | | | | | | |
| AGA | CTT | TTG | GAC | GAT | ATA | CTT | TGC | GAT | ACT | ATT | TTT | CTC | AAT | TCT | ACA | 1252 |
| Arg | Leu | Leu | Asp | Asp | Ile | Leu | Cys | Asp | Thr | Ile | Phe | Leu | Asn | Ser | Thr | |
| 75 | | | | 80 | | | | | 85 | | | | | 90 | | |
| GAC | CCG | AAG | GTC | ATG | CAA | AAG | GGC | CTG | CAA | TCG | AGG | GGT | ATT | TTA | AAA | 1300 |
| Asp | Pro | Lys | Val | Met | Gln | Lys | Gly | Leu | Gln | Ser | Arg | Gly | Ile | Leu | Lys | |
| | | | | 95 | | | | 100 | | | | | 105 | | | |
| GAG | TCT | ATG | CTT | TCT | TAC | TCA | ACT | TTC | AGA | AGT | AGT | ATT | CGC | CCT | AAC | 1348 |
| Glu | Ser | Met | Leu | Ser | Tyr | Ser | Thr | Phe | Arg | Ser | Ser | Ile | Arg | Pro | Asn | |
| | | | 110 | | | | | 115 | | | | | 120 | | | |
| TGC | TTG | GGT | TCA | TTA | ACT | GAT | CAA | GTG | GTT | TTT | CAA | ACA | AAA | TCC | GAG | 1396 |
| Cys | Leu | Gly | Ser | Leu | Thr | Asp | Gln | Val | Val | Phe | Gln | Thr | Lys | Ser | Glu | |
| | | 125 | | | | | 130 | | | | | 135 | | | | |
| TAT | GAT | TCC | ATT | TCA | TGC | CCA | AAA | TAT | AAT | AAA | ATA | CAT | GTA | TTT | CAG | 1444 |
| Tyr | Asp | Ser | Ile | Ser | Cys | Pro | Lys | Tyr | Asn | Lys | Ile | His | Val | Phe | Gln | |
| | 140 | | | | | 145 | | | | | 150 | | | | | |
| GCG | GTC | ATC | TTT | AAT | CCA | TCA | CTG | GCA | GAA | CAG | CAA | ATT | TCA | ACT | TTT | 1492 |
| Ala | Val | Ile | Phe | Asn | Pro | Ser | Leu | Ala | Glu | Gln | Gln | Ile | Ser | Thr | Phe | |
| 155 | | | | | 160 | | | | | 165 | | | | | 170 | |
| GAT | GAT | ATT | GTT | AAA | ATT | CCT | ATT | TAT | CAT | CTT | AAG | GTT | AGC | GTA | AAA | 1540 |
| Asp | Asp | Ile | Val | Lys | Ile | Pro | Ile | Tyr | His | Leu | Lys | Val | Ser | Val | Lys | |
| | | | | 175 | | | | 180 | | | | | 185 | | | |
| GTC | CGC | CAA | GAA | CTG | GAG | CGG | TTG | AAG | AAG | CAT | GTC | GGT | GTT | ACT | CAA | 1588 |

|     |     |     |     |     |     |     |     |     |     |     |     |     |     |     |     |
| --- | --- | --- | --- | --- | --- | --- | --- | --- | --- | --- | --- | --- | --- | --- | --- |
| Val | Arg | Gln | Glu<br>190 | Leu | Glu | Arg | Leu<br>195 | Lys | Lys | His | Val | Gly<br>200 | Val | Thr | Gln |

| | | | | | | | | | | | | | | | | |
|---|---|---|---|---|---|---|---|---|---|---|---|---|---|---|---|---|
| TTC | CAC | TCA | CTA | GAT | CAT | TTG | CAC | GAA | TAC | GAT | CGA | GTA | GAC | CTT | TCG | 1636 |
| Phe | His | Ser<br>205 | Leu | Asp | His | Leu | His<br>210 | Glu | Tyr | Asp | Arg | Val<br>215 | Asp | Leu | Ser | |
| ACT | TTT | GAT | TCT | TCC | GAT | CCT | AAT | TTG | TTG | GAT | TAC | GGT | ATT | TAC | GTT | 1684 |
| Thr | Phe<br>220 | Asp | Ser | Ser | Asp<br>225 | Pro | Asn | Leu | Leu | Asp<br>230 | Tyr | Gly | Ile | Tyr | Val | |
| TCT | GAT | GAT | ACT | AAC | AAA | CTG | ATC | TTG | ATT | GAA | ATT | TTT | AAA | CCC | GAG | 1732 |
| Ser<br>235 | Asp | Asp | Thr | Asn | Lys<br>240 | Leu | Ile | Leu | Ile | Glu<br>245 | Ile | Phe | Lys | Pro | Glu<br>250 | |
| TTT | AAT | TCA | CCT | GAA | GAG | CAT | GAG | AGT | TTT | ACT | GCC | GAC | GCA | ATT | AAG | 1780 |
| Phe | Asn | Ser | Pro<br>255 | Glu | Glu | His | Glu | Ser<br>260 | Phe | Thr | Ala | Asp | Ala<br>265 | Ile | Lys | |
| AAG | AGA | TAC | AAT | GCT | ATG | TGT | GTA | AAA | AAT | GAA | TCA | CTA | GAT | AAA | AGC | 1828 |
| Lys | Arg | Tyr | Asn<br>270 | Ala | Met | Cys | Val | Lys<br>275 | Asn | Glu | Ser | Leu | Asp<br>280 | Lys | Ser | |
| GAG | ACG | CCA | TCT | CAA | GTT | GAC | TGT | TTT | TAC | ACA | CTT | TTT | AAA | ATT | TTT | 1876 |
| Glu | Thr | Pro<br>285 | Ser | Gln | Val | Asp | Cys<br>290 | Phe | Tyr | Thr | Leu | Phe<br>295 | Lys | Ile | Phe | |
| AAA | GGG | CCT | TTG | ACG | AGG | AAA | AGT | AAA | GCG | GAA | CCT | ACA | AAG | ACA | ATT | 1924 |
| Lys | Gly<br>300 | Pro | Leu | Thr | Arg | Lys<br>305 | Ser | Lys | Ala | Glu | Pro<br>310 | Thr | Lys | Thr | Ile | |
| GAT | TCT | GGA | AAT | TTG | GCC | CTT | AAC | ACT | CAC | CTG | AAT | CCT | GAA | TGG | TTA | 1972 |
| Asp<br>315 | Ser | Gly | Asn | Leu | Ala<br>320 | Leu | Asn | Thr | His | Leu<br>325 | Asn | Pro | Glu | Trp | Leu<br>330 | |
| ACG | TCC | AAG | TAT | GGA | TTT | CAA | GCA | AGC | TCA | GAA | ATC | GAT | GAG | GAA | ACT | 2020 |
| Thr | Ser | Lys | Tyr | Gly<br>335 | Phe | Gln | Ala | Ser | Ser<br>340 | Glu | Ile | Asp | Glu | Glu<br>345 | Thr | |
| AAT | GAG | ATA | TTT | ACT | GAA | TAC | GTC | CCT | CCA | GAT | ATG | GTG | GAC | TAT | GTA | 2068 |
| Asn | Glu | Ile | Phe | Thr<br>350 | Glu | Tyr | Val | Pro | Pro<br>355 | Asp | Met | Val | Asp | Tyr<br>360 | Val | |
| AAC | GAT | TTG | GAG | ACA | AGA | AAA | ATT | CGA | GAA | TCG | TTT | GTG | AGG | AAG | TGT | 2116 |
| Asn | Asp | Leu | Glu<br>365 | Thr | Arg | Lys | Ile | Arg<br>370 | Glu | Ser | Phe | Val | Arg<br>375 | Lys | Cys | |
| TTA | CAA | CTG | ATA | TTT | TGG | GGT | CAA | CTA | TCT | ACC | TCA | TTA | CTG | GCA | CCT | 2164 |
| Leu | Gln | Leu<br>380 | Ile | Phe | Trp | Gly | Gln<br>385 | Leu | Ser | Thr | Ser | Leu<br>390 | Leu | Ala | Pro | |
| AAT | TCT | CCC | TTG | AAA | AAT | ACG | AAA | AGC | GTA | AAG | GGA | ATG | TCT | TCA | TTA | 2212 |
| Asn<br>395 | Ser | Pro | Leu | Lys | Asn<br>400 | Thr | Lys | Ser | Val | Lys<br>405 | Gly | Met | Ser | Ser<br>410 | Leu | |
| CAA | ACT | TCT | TTC | TCA | ACA | CTA | CCT | TGG | TTC | CAT | TTA | TTG | GGA | GAA | TCC | 2260 |
| Gln | Thr | Ser | Phe | Ser<br>415 | Thr | Leu | Pro | Trp | Phe<br>420 | His | Leu | Leu | Gly | Glu<br>425 | Ser | |
| AGA | GCA | AGG | ATT | CTA | TTA | AAT | TCC | AAT | GAG | CAA | ACT | CAT | TCT | CCT | TTG | 2308 |
| Arg | Ala | Arg | Ile<br>430 | Leu | Leu | Asn | Ser | Asn<br>435 | Glu | Gln | Thr | His | Ser<br>440 | Pro | Leu | |
| GAC | GCA | GAA | CCT | CAT | TTT | ATT | AAT | CTT | TCC | GTT | TCG | CAT | TAT | TAT | ACC | 2356 |
| Asp | Ala | Glu | Pro<br>445 | His | Phe | Ile | Asn | Leu<br>450 | Ser | Val | Ser | His | Tyr<br>455 | Tyr | Thr | |
| GAT | AGA | GAT | ATA | ATC | AGA | AAC | TAC | GAA | TCT | TTG | TCT | TCT | TTG | GAT | CCT | 2404 |
| Asp | Arg | Asp<br>460 | Ile | Ile | Arg | Asn | Tyr<br>465 | Glu | Ser | Leu | Ser | Ser<br>470 | Leu | Asp | Pro | |
| GAA | AAT | ATT | GGG | CTG | TAT | TTT | GAC | GCA | CTG | ACA | TAC | ATT | GCA | AAT | AGG | 2452 |
| Glu<br>475 | Asn | Ile | Gly | Leu | Tyr<br>480 | Phe | Asp | Ala | Leu | Thr<br>485 | Tyr | Ile | Ala | Asn<br>490 | Arg | |
| AAG | GGG | GCA | TAT | CAA | TTG | ATT | GCT | TAC | TGT | GGA | AAA | CAG | GAC | ATT | ATA | 2500 |
| Lys | Gly | Ala | Tyr | Gln<br>495 | Leu | Ile | Ala | Tyr | Cys<br>500 | Gly | Lys | Gln | Asp | Ile<br>505 | Ile | |
| GGC | CAA | GAA | GCT | CTA | GAA | AAT | GCT | TTG | TTA | ATG | TTT | AAA | ATT | AAC | CCT | 2548 |
| Gly | Gln | Glu | Ala<br>510 | Leu | Glu | Asn | Ala | Leu<br>515 | Leu | Met | Phe | Lys | Ile<br>520 | Asn | Pro | |

| | | | | | | | | | | | | | | | | |
|---|---|---|---|---|---|---|---|---|---|---|---|---|---|---|---|---|
| AAA | GAG | TGT | AAC | ATC | TCC | GAA | TTA | AAT | GAG | GCG | ACT | TTG | CTA | TCT | ATT | 2596 |
| Lys | Glu 525 | Cys | Asn | Ile | Ser | Glu 530 | Leu | Asn | Glu | Ala | Thr | Leu 535 | Leu | Ser | Ile | |
| TAC | AAA | TAT | GAA | ACA | TCA | AAT | AAG | AGC | CAA | GTA | ACC | TCT | AAT | CAC | CTA | 2644 |
| Tyr | Lys 540 | Tyr | Glu | Thr | Ser | Asn | Lys 545 | Ser | Gln | Val | Thr | Ser 550 | Asn | His | Leu | |
| ACA | AAT | TTG | AAA | AAT | GCT | CTA | AGA | TTG | TTG | GCC | AAA | TAT | ACC | AAA | TCT | 2692 |
| Thr 555 | Asn | Leu | Lys | Asn | Ala 560 | Leu | Arg | Leu | Leu | Ala 565 | Lys | Tyr | Thr | Lys | Ser 570 | |
| GAC | AAA | CTA | AAA | TTT | TAC | GTC | GAT | CAT | GAG | CCC | TAC | AGA | GCT | TTA | TCC | 2740 |
| Asp | Lys | Leu | Lys | Phe 575 | Tyr | Val | Asp | His | Glu 580 | Pro | Tyr | Arg | Ala | Leu 585 | Ser | |
| CAG | GCA | TAC | GAC | ACA | CTT | TCA | ATT | GAC | GAG | TCT | GTT | GAT | GAA | GAC | ATT | 2788 |
| Gln | Ala | Tyr | Asp 590 | Thr | Leu | Ser | Ile | Asp 595 | Glu | Ser | Val | Asp | Glu 600 | Asp | Ile | |
| ATA | AAA | ACT | GCA | TAT | TCG | GTC | AAG | ATT | AAC | GAC | TCT | CCC | GGA | TTA | AAG | 2836 |
| Ile | Lys | Thr 605 | Ala | Tyr | Ser | Val | Lys 610 | Ile | Asn | Asp | Ser | Pro 615 | Gly | Leu | Lys | |
| TTG | GAT | TGT | GAT | AGA | GCA | CTT | TAC | ACC | ATT | GCT | ATC | AGT | AAA | AGA | AGC | 2884 |
| Leu | Asp 620 | Cys | Asp | Arg | Ala | Leu 625 | Tyr | Thr | Ile | Ala | Ile 630 | Ser | Lys | Arg | Ser | |
| CTT | GAT | TTG | TTC | AAT | TTT | TTA | ACA | GAG | GAA | TGC | CCA | CAG | TTT | TCC | AAC | 2932 |
| Leu 635 | Asp | Leu | Phe | Asn | Phe 640 | Leu | Thr | Glu | Glu | Cys 645 | Pro | Gln | Phe | Ser | Asn 650 | |
| TAT | TAT | GGT | CCA | GAG | AAG | CTT | CTT | CAA | GTG | AAT | GAA | AAT | GCC | TCT | GAC | 2980 |
| Tyr | Tyr | Gly | Pro | Glu 655 | Lys | Leu | Leu | Gln | Val 660 | Asn | Glu | Asn | Ala | Ser 665 | Asp | |
| GAA | ACC | ATT | TTG | AAA | ATC | TTT | AAA | CAA | AAG | TGG | TTT | GAT | GAA | AAC | GTT | 3028 |
| Glu | Thr | Ile | Leu 670 | Lys | Ile | Phe | Lys | Gln 675 | Lys | Trp | Phe | Asp | Glu 680 | Asn | Val | |
| TAT | GAG | CCT | GAC | CAA | TTT | CTT | ATT | TTG | AGG | GCA | GCA | TTG | ACC | AAA | ATC | 3076 |
| Tyr | Glu | Pro 685 | Asp | Gln | Phe | Leu | Ile 690 | Leu | Arg | Ala | Ala | Leu 695 | Thr | Lys | Ile | |
| AGT | ATA | GAA | AGA | AAT | TCA | ACT | TTA | ATC | ACC | AAC | TTC | TTA | CTA | ACT | GGT | 3124 |
| Ser | Ile 700 | Glu | Arg | Asn | Ser | Thr 705 | Leu | Ile | Thr | Asn | Phe 710 | Leu | Leu | Thr | Gly | |
| ACG | ATA | GAT | CCA | AAT | TCC | TTG | CCG | CCA | GAA | AAT | TGG | CCA | ACT | GGC | ATT | 3172 |
| Thr 715 | Ile | Asp | Pro | Asn | Ser 720 | Leu | Pro | Pro | Glu | Asn 725 | Trp | Pro | Thr | Gly | Ile 730 | |
| AAT | AAT | ATC | GGG | AAC | ACC | TGT | TAC | CTA | AAT | TCT | TTA | TTA | CAA | TAT | TAC | 3220 |
| Asn | Asn | Ile | Gly | Asn 735 | Thr | Cys | Tyr | Leu | Asn 740 | Ser | Leu | Leu | Gln | Tyr 745 | Tyr | |
| TTT | TCC | ATT | GCG | CCA | CTA | AGA | AGA | TAT | GTA | TTG | GAA | TAT | CAA | AAA | ACG | 3268 |
| Phe | Ser | Ile | Ala 750 | Pro | Leu | Arg | Arg | Tyr 755 | Val | Leu | Glu | Tyr | Gln 760 | Lys | Thr | |
| GTA | GAA | AAT | TTC | AAT | GAC | CAC | CTC | TCT | AAT | AGT | GGG | CAT | ATT | AGA | AGA | 3316 |
| Val | Glu | Asn 765 | Phe | Asn | Asp | His | Leu 770 | Ser | Asn | Ser | Gly | His 775 | Ile | Arg | Arg | |
| ATT | GGT | GGA | AGA | GAA | ATT | AGT | AGA | GGC | GAA | GTG | GAA | AGA | TCT | ATT | CAA | 3364 |
| Ile | Gly | Gly | Arg 780 | Glu | Ile | Ser | Arg | Gly 785 | Glu | Val | Glu | Arg | Ser 790 | Ile | Gln | |
| TTC | ATA | TAC | CAA | CTT | CGC | AAC | CTT | TTC | TAT | GCG | ATG | GTT | CAT | ACA | AGA | 3412 |
| Phe 795 | Ile | Tyr | Gln | Leu | Arg 800 | Asn | Leu | Phe | Tyr | Ala 805 | Met | Val | His | Thr | Arg 810 | |
| GAA | AGA | TGT | GTA | ACA | CCC | TCA | AAA | GAG | CTA | GCA | TAT | TTG | GCA | TTT | GCT | 3460 |
| Glu | Arg | Cys | Val | Thr 815 | Pro | Ser | Lys | Glu | Leu 820 | Ala | Tyr | Leu | Ala | Phe 825 | Ala | |
| CCA | AGT | AAT | GTT | GAA | GTA | GAA | TTT | GAA | GTG | GAA | GGC | AAT | AAA | GTA | GTT | 3508 |
| Pro | Ser | Asn | Val 830 | Glu | Val | Glu | Phe | Glu 835 | Val | Glu | Gly | Asn | Lys 840 | Val | Val | |
| GAT | CAA | ACA | GGA | GTT | CTT | TCG | GAT | TCA | AAG | AAG | GAA | ACA | ACG | GAT | GAC | 3556 |

|     |     |     |     |     |     |     |     |     |     |     |     |     |     |     |     |
| --- | --- | --- | --- | --- | --- | --- | --- | --- | --- | --- | --- | --- | --- | --- | --- |
| Asp | Gln | Thr | Gly | Val | Leu | Ser | Asp | Ser | Lys | Lys | Glu | Thr | Thr | Asp | Asp |
|     |     |     | 845 |     |     |     | 850 |     |     |     |     | 855 |     |     |     |

| GCA | TTT | ACT | ACA | AAA | ATA | AAG | GAT | ACA | AGC | CTG | ATT | GAT | TTA | GAA | ATG | 3604 |
| --- | --- | --- | --- | --- | --- | --- | --- | --- | --- | --- | --- | --- | --- | --- | --- | --- |
| Ala | Phe | Thr | Thr | Lys | Ile | Lys | Asp | Thr | Ser | Leu | Ile | Asp | Leu | Glu | Met |      |
|     | 860 |     |     |     | 865 |     |     |     |     | 870 |     |     |     |     |     |      |

| GAA | GAT | GGC | CTT | AAT | GGC | GAT | GTT | GGT | ACA | GAT | GCG | AAC | AGA | AAA | AAA | 3652 |
| --- | --- | --- | --- | --- | --- | --- | --- | --- | --- | --- | --- | --- | --- | --- | --- | --- |
| Glu | Asp | Gly | Leu | Asn | Gly | Asp | Val | Gly | Thr | Asp | Ala | Asn | Arg | Lys | Lys |      |
| 875 |     |     |     |     | 880 |     |     |     |     | 885 |     |     |     |     | 890 |      |

| AAT | GAA | TCG | AAT | GAT | GCT | GAA | GTA | AGT | GAG | AAC | GAA | GAT | ACA | ACA | GGA | 3700 |
| --- | --- | --- | --- | --- | --- | --- | --- | --- | --- | --- | --- | --- | --- | --- | --- | --- |
| Asn | Glu | Ser | Asn | Asp | Ala | Glu | Val | Ser | Glu | Asn | Glu | Asp | Thr | Thr | Gly |      |
|     |     |     |     | 895 |     |     |     |     | 900 |     |     |     |     | 905 |     |      |

| TTA | ACT | TCA | CCT | ACG | CGT | GTG | GCA | AAA | ATC | AGT | TCT | GAT | CAA | TTA | GAA | 3748 |
| --- | --- | --- | --- | --- | --- | --- | --- | --- | --- | --- | --- | --- | --- | --- | --- | --- |
| Leu | Thr | Ser | Pro | Thr | Arg | Val | Ala | Lys | Ile | Ser | Ser | Asp | Gln | Leu | Glu |      |
|     |     |     | 910 |     |     |     |     | 915 |     |     |     |     | 920 |     |     |      |

| AAT | GCT | TTG | GAA | ATG | GGT | AGG | CAA | CAA | GAT | GTT | ACT | GAA | TGC | ATA | GGA | 3796 |
| --- | --- | --- | --- | --- | --- | --- | --- | --- | --- | --- | --- | --- | --- | --- | --- | --- |
| Asn | Ala | Leu | Glu | Met | Gly | Arg | Gln | Gln | Asp | Val | Thr | Glu | Cys | Ile | Gly |      |
|     |     |     | 925 |     |     |     | 930 |     |     |     |     | 935 |     |     |     |      |

| AAC | GTG | TTA | TTT | CAG | ATA | GAA | AGC | GGT | TCA | GAG | CCT | ATC | CGA | TAT | GAT | 3844 |
| --- | --- | --- | --- | --- | --- | --- | --- | --- | --- | --- | --- | --- | --- | --- | --- | --- |
| Asn | Val | Leu | Phe | Gln | Ile | Glu | Ser | Gly | Ser | Glu | Pro | Ile | Arg | Tyr | Asp |      |
|     | 940 |     |     |     |     | 945 |     |     |     |     | 950 |     |     |     |     |      |

| GAA | GAC | AAC | GAG | CAA | TAT | GAC | TTG | GTT | AAG | CAA | CTA | TTT | TAT | GGT | ACT | 3892 |
| --- | --- | --- | --- | --- | --- | --- | --- | --- | --- | --- | --- | --- | --- | --- | --- | --- |
| Glu | Asp | Asn | Glu | Gln | Tyr | Asp | Leu | Val | Lys | Gln | Leu | Phe | Tyr | Gly | Thr |      |
| 955 |     |     |     |     | 960 |     |     |     |     | 965 |     |     |     |     | 970 |      |

| ACT | AAA | CAA | AGT | ATT | GTT | CCT | TTG | TCC | GCA | ACA | AAT | AAA | GTC | CGT | ACG | 3940 |
| --- | --- | --- | --- | --- | --- | --- | --- | --- | --- | --- | --- | --- | --- | --- | --- | --- |
| Thr | Lys | Gln | Ser | Ile | Val | Pro | Leu | Ser | Ala | Thr | Asn | Lys | Val | Arg | Thr |      |
|     |     |     |     | 975 |     |     |     |     | 980 |     |     |     |     | 985 |     |      |

| AAA | GTT | GAA | AGA | TTC | CTA | TCG | TTA | CTG | ATA | AAT | ATT | GGC | GAT | CAT | CCT | 3988 |
| --- | --- | --- | --- | --- | --- | --- | --- | --- | --- | --- | --- | --- | --- | --- | --- | --- |
| Lys | Val | Glu | Arg | Phe | Leu | Ser | Leu | Leu | Ile | Asn | Ile | Gly | Asp | His | Pro |      |
|     |     |     | 990 |     |     |     |     | 995 |     |     |     |     | 1000|     |     |      |

| AAA | GAT | ATT | TAT | GAT | GCG | TTT | GAT | TCT | TAT | TTT | AAA | GAC | GAA | TAT | CTG | 4036 |
| --- | --- | --- | --- | --- | --- | --- | --- | --- | --- | --- | --- | --- | --- | --- | --- | --- |
| Lys | Asp | Ile | Tyr | Asp | Ala | Phe | Asp | Ser | Tyr | Phe | Lys | Asp | Glu | Tyr | Leu |      |
|     |     |     | 1005|     |     |     |     | 1010|     |     |     |     | 1015|     |     |      |

| ACA | ATG | GAA | GAG | TAT | GGT | GAT | GTT | ATA | CGT | ACC | GTT | GCT | GTT | ACA | ACT | 4084 |
| --- | --- | --- | --- | --- | --- | --- | --- | --- | --- | --- | --- | --- | --- | --- | --- | --- |
| Thr | Met | Glu | Glu | Tyr | Gly | Asp | Val | Ile | Arg | Thr | Val | Ala | Val | Thr | Thr |      |
|     |     | 1020|     |     |     |     | 1025|     |     |     |     | 1030|     |     |     |      |

| TTT | CCT | ACT | ATT | TTG | CAG | GTA | CAA | ATC | CAA | AGA | GTT | TAT | TAC | GAT | CGT | 4132 |
| --- | --- | --- | --- | --- | --- | --- | --- | --- | --- | --- | --- | --- | --- | --- | --- | --- |
| Phe | Pro | Thr | Ile | Leu | Gln | Val | Gln | Ile | Gln | Arg | Val | Tyr | Tyr | Asp | Arg |      |
| 1035|     |     |     |     | 1040|     |     |     |     | 1045|     |     |     |     | 1050|      |

| GAA | AGA | TTA | ATG | CCG | TTT | AAA | TCC | ATT | GAG | CCC | TTA | CCA | TTC | AAA | GAA | 4180 |
| --- | --- | --- | --- | --- | --- | --- | --- | --- | --- | --- | --- | --- | --- | --- | --- | --- |
| Glu | Arg | Leu | Met | Pro | Phe | Lys | Ser | Ile | Glu | Pro | Leu | Pro | Phe | Lys | Glu |      |
|     |     |     |     | 1055|     |     |     |     | 1060|     |     |     |     | 1065|     |      |

| GTT | ATT | TAC | ATG | GAC | AGA | TAC | GCG | GAT | ACA | GAG | AAC | CCT | TTA | TTG | TTG | 4228 |
| --- | --- | --- | --- | --- | --- | --- | --- | --- | --- | --- | --- | --- | --- | --- | --- | --- |
| Val | Ile | Tyr | Met | Asp | Arg | Tyr | Ala | Asp | Thr | Glu | Asn | Pro | Leu | Leu | Leu |      |
|     |     |     | 1070|     |     |     |     | 1075|     |     |     |     | 1080|     |     |      |

| GCA | AAA | AAG | AAA | GAA | ACA | GAA | GAA | ATG | AAG | CAA | AAG | TTG | AAG | GTA | ATG | 4276 |
| --- | --- | --- | --- | --- | --- | --- | --- | --- | --- | --- | --- | --- | --- | --- | --- | --- |
| Ala | Lys | Lys | Lys | Glu | Thr | Glu | Glu | Met | Lys | Gln | Lys | Leu | Lys | Val | Met |      |
|     |     |     |     | 1085|     |     |     |     | 1090|     |     |     |     | 1095|     |      |

| AAA | AAT | AGA | CAA | AGA | GAG | CTT | TTG | AGT | CGT | GAT | GAT | TCA | GGG | CTT | ACA | 4324 |
| --- | --- | --- | --- | --- | --- | --- | --- | --- | --- | --- | --- | --- | --- | --- | --- | --- |
| Lys | Asn | Arg | Gln | Arg | Glu | Leu | Leu | Ser | Arg | Asp | Asp | Ser | Gly | Leu | Thr |      |
|     | 1100|     |     |     | 1105|     |     |     |     | 1110|     |     |     |     |     |      |

| AGG | AAG | GAT | GCA | TTT | TTG | GAG | AGT | ATC | AAG | CTA | TTG | GAA | TCG | GAT | ACC | 4372 |
| --- | --- | --- | --- | --- | --- | --- | --- | --- | --- | --- | --- | --- | --- | --- | --- | --- |
| Arg | Lys | Asp | Ala | Phe | Leu | Glu | Ser | Ile | Lys | Leu | Leu | Glu | Ser | Asp | Thr |      |
| 1115|     |     |     | 1120|     |     |     |     | 1125|     |     |     |     | 1130|     |      |

| ATA | AAG | AAA | ACT | CCT | TTA | AAA | ATT | GAG | GCT | GCT | AAT | GAT | GTG | ATA | AAG | 4420 |
| --- | --- | --- | --- | --- | --- | --- | --- | --- | --- | --- | --- | --- | --- | --- | --- | --- |
| Ile | Lys | Lys | Thr | Pro | Leu | Lys | Ile | Glu | Ala | Ala | Asn | Asp | Val | Ile | Lys |      |
|     |     |     |     | 1135|     |     |     |     | 1140|     |     |     |     | 1145|     |      |

| ACG | CTG | AGA | AAC | AAC | GTT | CAA | AAT | ATC | GAT | AAT | GAA | TTG | ATG | AAA | TTA | 4468 |
| --- | --- | --- | --- | --- | --- | --- | --- | --- | --- | --- | --- | --- | --- | --- | --- | --- |
| Thr | Leu | Arg | Asn | Asn | Val | Gln | Asn | Ile | Asp | Asn | Glu | Leu | Met | Lys | Leu |      |
|     |     |     |     | 1150|     |     |     |     | 1155|     |     |     |     | 1160|     |      |

| TAC | AAT | GAT | ATC | AAC | AGT | TTG | GAA | GAG | AAA | ATA | AGC | CAT | CAA | TTT | GAC | 4516 |
| --- | --- | --- | --- | --- | --- | --- | --- | --- | --- | --- | --- | --- | --- | --- | --- | --- |
| Tyr | Asn | Asp | Ile | Asn | Ser | Leu | Glu | Glu | Lys | Ile | Ser | His | Gln | Phe | Asp |      |
|     |     |     | 1165|     |     |     |     | 1170|     |     |     |     | 1175|     |     |      |

```
GAT TTC AAG GAA TAT GGT TAC TCA CTG TTT TCG GTT TTT ATT CAT CGC       4564
Asp Phe Lys Glu Tyr Gly Tyr Ser Leu Phe Ser Val Phe Ile His Arg
    1180                1185                1190

GGC GAG GCC AGT TAT GGT CAC TAT TGG ATA TAT ATC AAG GAC AGA AAT       4612
Gly Glu Ala Ser Tyr Gly His Tyr Trp Ile Tyr Ile Lys Asp Arg Asn
1195                1200                1205                1210

CGC AAT GGA ATT TGG AGG AAG TAC AAT GAT GAA ACC ATC AGC GAG GTC       4660
Arg Asn Gly Ile Trp Arg Lys Tyr Asn Asp Glu Thr Ile Ser Glu Val
                1215                1220                1225

CAG GAA GAG GAG GTC TTC AAT TTC AAT GAG GGT AAC ACT GCA ACT CCA       4708
Gln Glu Glu Glu Val Phe Asn Phe Asn Glu Gly Asn Thr Ala Thr Pro
            1230                1235                1240

TAT TTC CTA GTA TAT GTC AAA CAA GGA CAA GAA GGT GAT ATT GAG CCA       4756
Tyr Phe Leu Val Tyr Val Lys Gln Gly Gln Glu Gly Asp Ile Glu Pro
        1245                1250                1255

TTG AAA AGA ATT CTA AAG TAGTCTTAGT CAATGAAGAG TTTATGTAAA              4804
Leu Lys Arg Ile Leu Lys
    1260
```

| | | | | | |
|---|---|---|---|---|---|
| ATGTCACTAT | TGCCATAAGT | ACCATTATTA | TGTAAAAAGC | TTTGCCATAT | TCAATGTTAC | 4864 |
| GGGTGACTAT | CTGCTACGTA | AAGAAAAACG | AAAAACAAA | AAAAAAAGA | ACAAGCTCAT | 4924 |
| AGAAGTGAAT | ACGAAAGCTG | AAGAAAGTCG | TTAAGTAGAT | AGGTTGCGTA | ACTAGGTGC | 4984 |
| GTCCAATCAA | AGTAATCCAA | TTAGATATAC | TGGACTATAA | TTAAGATGTC | ATCTGAAAGC | 5044 |
| CCACAGGATC | AACCACAGAA | GGAGCAAATC | AGCAATAACG | TCGGCGTTAC | CACCAATAGT | 5104 |
| ACAAGCAATG | AGGAAACAAG | CCGCTCTCAA | GATGATAATG | TCAAGGAAGT | CAATGGAAAT | 5164 |
| GATGATACTA | AAGAAGAGGA | ACAAGAAGAA | GACGCAGAAC | TAGATGATTT | ATTTGGAGAT | 5224 |
| GACAATGATG | ACGATGATGA | TGATGATGTT | AAAAAATCGG | AGACTGAAAA | AAGTGATAGT | 5284 |
| GATAGTGATG | AAGACGACGA | GGGAGAGAAT | ATCAACCATA | GAAGTCGTCA | TAGAGAAAGT | 5344 |
| CTCGGGTTAG | ATGATGATGA | AGCAGAGGAG | CAAGCCATGT | ACACCCGAAA | ATTTTATGGT | 5404 |
| GAGGATGCTA | ATAACTTTTC | TGATCTTGAT | GAGACTACTC | ACACTTTTAA | AGAGGAAAAT | 5464 |
| GTAGAGCTTG | TCAGACATAT | TATTCCAAGT | AAAGCTAATG | TGAATGAAAC | GGCGTCTCAC | 5524 |
| AACGAAATTT | TCTATGCTAG | AATTCCCAAC | TTTTTAACTA | TCGATCCAAT | TCCTTTCGAC | 5584 |
| CCTCCAAGTT | TTGAGGCCAA | AGTAAACGAA | AGGGCAAGCA | ATTCAGCTTC | TAGGGAGGAT | 5644 |
| CAACTGGACG | ACCGCCTGAT | TGATGAAAAC | ACTGTTAGAT | GGAGATACTC | TCGTGACAAA | 5704 |
| GACCAACATG | TCTTTAAAGA | ATCAAATACA | CAAATAGTGC | AGTGGTCAGA | CGGTACATAT | 5764 |
| TCGCTAAAAG | TTGGTGAAGA | GTGTACAGAT | ATATTGGTCA | ACGATACGAG | CAACACTTTT | 5824 |
| TTGACAGTAT | CGCATGACCA | ACAAGAGTTG | ATCCAGTGTT | ACGAAGGGGG | TGAAATAAAA | 5884 |
| AAGACGTTGA | TGTTTATTCC | AACTTCGACG | AATTCAAAAA | TACATCAAAA | ACTAAGTAAA | 5944 |
| GCTGTTATAA | GAAGGAACCA | AAGACAAAGC | AAGGGTCCTG | GAAATACATT | GTAAGTATGG | 6004 |
| ATCC | | | | | | 6008 |

( 2 ) INFORMATION FOR SEQ ID NO:6:

( i ) SEQUENCE CHARACTERISTICS:
        ( A ) LENGTH: 1264 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Pro Asn Glu Asp Asn Glu Leu Gln Lys Ala Ile Glu Asn His His
1               5                   10                  15
```

| | | | | | | | | | | | | | |
|---|---|---|---|---|---|---|---|---|---|---|---|---|---|
|Asn|Gln|Leu|Leu|Asn|Gln|Asp|Lys|Glu|Asn|Ala|Asp|Arg|Asn|Gly|Ser|
| | | |20| | | |25| | | |30| | |
|Val|Ile|Glu|Asp|Leu|Pro|Leu|Tyr|Gly|Thr|Ser|Ile|Asn|Gln|Gln|Ser|
| | |35| | | |40| | | |45| | | |
|Thr|Pro|Gly|Asp|Val|Asp|Asp|Gly|Lys|His|Leu|Leu|Tyr|Pro|Asp|Ile|
| |50| | | |55| | | |60| | | | |
|Ala|Thr|Asn|Leu|Pro|Leu|Lys|Thr|Ser|Asp|Arg|Leu|Leu|Asp|Asp|Ile|
|65| | | |70| | | |75| | | | |80|
|Leu|Cys|Asp|Thr|Ile|Phe|Leu|Asn|Ser|Thr|Asp|Pro|Lys|Val|Met|Gln|
| | | |85| | | |90| | | |95| | |
|Lys|Gly|Leu|Gln|Ser|Arg|Gly|Ile|Leu|Lys|Glu|Ser|Met|Leu|Ser|Tyr|
| | |100| | | |105| | | |110| | | |
|Ser|Thr|Phe|Arg|Ser|Ser|Ile|Arg|Pro|Asn|Cys|Leu|Gly|Ser|Leu|Thr|
| |115| | | |120| | | |125| | | | |
|Asp|Gln|Val|Val|Phe|Gln|Thr|Lys|Ser|Glu|Tyr|Asp|Ser|Ile|Ser|Cys|
|130| | | |135| | | |140| | | | | |
|Pro|Lys|Tyr|Asn|Lys|Ile|His|Val|Phe|Gln|Ala|Val|Ile|Phe|Asn|Pro|
|145| | | |150| | | |155| | | | |160|
|Ser|Leu|Ala|Glu|Gln|Gln|Ile|Ser|Thr|Phe|Asp|Asp|Ile|Val|Lys|Ile|
| | | |165| | | |170| | | | |175| |
|Pro|Ile|Tyr|His|Leu|Lys|Val|Ser|Val|Lys|Val|Arg|Gln|Glu|Leu|Glu|
| | |180| | | |185| | | |190| | | |
|Arg|Leu|Lys|Lys|His|Val|Gly|Val|Thr|Gln|Phe|His|Ser|Leu|Asp|His|
| |195| | | |200| | | |205| | | | |
|Leu|His|Glu|Tyr|Asp|Arg|Val|Asp|Leu|Ser|Thr|Phe|Asp|Ser|Ser|Asp|
|210| | | |215| | | |220| | | | | |
|Pro|Asn|Leu|Leu|Asp|Tyr|Gly|Ile|Tyr|Val|Ser|Asp|Asp|Thr|Asn|Lys|
|225| | | |230| | | |235| | | | |240|
|Leu|Ile|Leu|Ile|Glu|Ile|Phe|Lys|Pro|Glu|Phe|Asn|Ser|Pro|Glu|Glu|
| | | |245| | | |250| | | |255| | |
|His|Glu|Ser|Phe|Thr|Ala|Asp|Ala|Ile|Lys|Lys|Arg|Tyr|Asn|Ala|Met|
| | |260| | | |265| | | |270| | | |
|Cys|Val|Lys|Asn|Glu|Ser|Leu|Asp|Lys|Ser|Glu|Thr|Pro|Ser|Gln|Val|
| |275| | | |280| | | |285| | | | |
|Asp|Cys|Phe|Tyr|Thr|Leu|Phe|Lys|Ile|Phe|Lys|Gly|Pro|Leu|Thr|Arg|
|290| | | |295| | | |300| | | | | |
|Lys|Ser|Lys|Ala|Glu|Pro|Thr|Lys|Thr|Ile|Asp|Ser|Gly|Asn|Leu|Ala|
|305| | | |310| | | |315| | | | |320|
|Leu|Asn|Thr|His|Leu|Asn|Pro|Glu|Trp|Leu|Thr|Ser|Lys|Tyr|Gly|Phe|
| | | |325| | | |330| | | | |335| |
|Gln|Ala|Ser|Ser|Glu|Ile|Asp|Glu|Glu|Thr|Asn|Glu|Ile|Phe|Thr|Glu|
| | | |340| | | |345| | | | |350| |
|Tyr|Val|Pro|Pro|Asp|Met|Val|Asp|Tyr|Val|Asn|Asp|Leu|Glu|Thr|Arg|
| | |355| | | |360| | | |365| | | |
|Lys|Ile|Arg|Glu|Ser|Phe|Val|Arg|Lys|Cys|Leu|Gln|Leu|Ile|Phe|Trp|
| |370| | | |375| | | |380| | | | |
|Gly|Gln|Leu|Ser|Thr|Ser|Leu|Leu|Ala|Pro|Asn|Ser|Pro|Leu|Lys|Asn|
|385| | | |390| | | |395| | | | |400|
|Thr|Lys|Ser|Val|Lys|Gly|Met|Ser|Ser|Leu|Gln|Thr|Ser|Phe|Ser|Thr|
| | | |405| | | |410| | | | |415| |
|Leu|Pro|Trp|Phe|His|Leu|Leu|Gly|Glu|Ser|Arg|Ala|Arg|Ile|Leu|Leu|
| | |420| | | |425| | | |430| | | |
|Asn|Ser|Asn|Glu|Gln|Thr|His|Ser|Pro|Leu|Asp|Ala|Glu|Pro|His|Phe|
| | |435| | | |440| | | |445| | | |
|Ile|Asn|Leu|Ser|Val|Ser|His|Tyr|Tyr|Thr|Asp|Arg|Asp|Ile|Ile|Arg|

```
            450                      455                      460
Asn  Tyr  Glu  Ser  Leu  Ser  Ser  Leu  Asp  Pro  Glu  Asn  Ile  Gly  Leu  Tyr
465                      470                      475                      480

Phe  Asp  Ala  Leu  Thr  Tyr  Ile  Ala  Asn  Arg  Lys  Gly  Ala  Tyr  Gln  Leu
                         485                      490                      495

Ile  Ala  Tyr  Cys  Gly  Lys  Gln  Asp  Ile  Ile  Gly  Gln  Glu  Ala  Leu  Glu
                    500                      505                      510

Asn  Ala  Leu  Leu  Met  Phe  Lys  Ile  Asn  Pro  Lys  Glu  Cys  Asn  Ile  Ser
               515                      520                      525

Glu  Leu  Asn  Glu  Ala  Thr  Leu  Leu  Ser  Ile  Tyr  Lys  Tyr  Glu  Thr  Ser
     530                      535                      540

Asn  Lys  Ser  Gln  Val  Thr  Ser  Asn  His  Leu  Thr  Asn  Leu  Lys  Asn  Ala
545                      550                      555                      560

Leu  Arg  Leu  Leu  Ala  Lys  Tyr  Thr  Lys  Ser  Asp  Lys  Leu  Lys  Phe  Tyr
                    565                      570                      575

Val  Asp  His  Glu  Pro  Tyr  Arg  Ala  Leu  Ser  Gln  Ala  Tyr  Asp  Thr  Leu
               580                      585                      590

Ser  Ile  Asp  Glu  Ser  Val  Asp  Glu  Asp  Ile  Ile  Lys  Thr  Ala  Tyr  Ser
          595                      600                      605

Val  Lys  Ile  Asn  Asp  Ser  Pro  Gly  Leu  Lys  Leu  Asp  Cys  Asp  Arg  Ala
     610                      615                      620

Leu  Tyr  Thr  Ile  Ala  Ile  Ser  Lys  Arg  Ser  Leu  Asp  Leu  Phe  Asn  Phe
625                      630                      635                      640

Leu  Thr  Glu  Glu  Cys  Pro  Gln  Phe  Ser  Asn  Tyr  Tyr  Gly  Pro  Glu  Lys
                    645                      650                      655

Leu  Leu  Gln  Val  Asn  Glu  Asn  Ala  Ser  Asp  Glu  Thr  Ile  Leu  Lys  Ile
               660                      665                      670

Phe  Lys  Gln  Lys  Trp  Phe  Asp  Glu  Asn  Val  Tyr  Glu  Pro  Asp  Gln  Phe
          675                      680                      685

Leu  Ile  Leu  Arg  Ala  Ala  Leu  Thr  Lys  Ile  Ser  Ile  Glu  Arg  Asn  Ser
     690                      695                      700

Thr  Leu  Ile  Thr  Asn  Phe  Leu  Leu  Thr  Gly  Thr  Ile  Asp  Pro  Asn  Ser
705                      710                      715                      720

Leu  Pro  Pro  Glu  Asn  Trp  Pro  Thr  Gly  Ile  Asn  Asn  Ile  Gly  Asn  Thr
                    725                      730                      735

Cys  Tyr  Leu  Asn  Ser  Leu  Leu  Gln  Tyr  Tyr  Phe  Ser  Ile  Ala  Pro  Leu
               740                      745                      750

Arg  Arg  Tyr  Val  Leu  Glu  Tyr  Gln  Lys  Thr  Val  Glu  Asn  Phe  Asn  Asp
          755                      760                      765

His  Leu  Ser  Asn  Ser  Gly  His  Ile  Arg  Arg  Ile  Gly  Gly  Arg  Glu  Ile
     770                      775                      780

Ser  Arg  Gly  Glu  Val  Glu  Arg  Ser  Ile  Gln  Phe  Ile  Tyr  Gln  Leu  Arg
785                      790                      795                      800

Asn  Leu  Phe  Tyr  Ala  Met  Val  His  Thr  Arg  Glu  Arg  Cys  Val  Thr  Pro
                    805                      810                      815

Ser  Lys  Glu  Leu  Ala  Tyr  Leu  Ala  Phe  Ala  Pro  Ser  Asn  Val  Glu  Val
               820                      825                      830

Glu  Phe  Glu  Val  Glu  Gly  Asn  Lys  Val  Val  Asp  Gln  Thr  Gly  Val  Leu
          835                      840                      845

Ser  Asp  Ser  Lys  Lys  Glu  Thr  Thr  Asp  Ala  Phe  Thr  Thr  Lys  Ile
850                      855                      860

Lys  Asp  Thr  Ser  Leu  Ile  Asp  Leu  Glu  Met  Glu  Asp  Gly  Leu  Asn  Gly
865                      870                      875                      880

Asp  Val  Gly  Thr  Asp  Ala  Asn  Arg  Lys  Lys  Asn  Glu  Ser  Asn  Asp  Ala
                    885                      890                      895
```

| Glu | Val | Ser | Glu | Asn | Glu | Asp | Thr | Thr | Gly | Leu | Thr | Ser | Pro | Thr | Arg |
|---|---|---|---|---|---|---|---|---|---|---|---|---|---|---|---|
| | | | 900 | | | | 905 | | | | | 910 | | | |
| Val | Ala | Lys | Ile | Ser | Ser | Asp | Gln | Leu | Glu | Asn | Ala | Leu | Glu | Met | Gly |
| | | 915 | | | | 920 | | | | | 925 | | | | |
| Arg | Gln | Gln | Asp | Val | Thr | Glu | Cys | Ile | Gly | Asn | Val | Leu | Phe | Gln | Ile |
| | 930 | | | | | 935 | | | | | 940 | | | | |
| Glu | Ser | Gly | Ser | Glu | Pro | Ile | Arg | Tyr | Asp | Glu | Asp | Asn | Glu | Gln | Tyr |
| 945 | | | | | 950 | | | | | 955 | | | | | 960 |
| Asp | Leu | Val | Lys | Gln | Leu | Phe | Tyr | Gly | Thr | Thr | Lys | Gln | Ser | Ile | Val |
| | | | | 965 | | | | | 970 | | | | | 975 | |
| Pro | Leu | Ser | Ala | Thr | Asn | Lys | Val | Arg | Thr | Lys | Val | Glu | Arg | Phe | Leu |
| | | | 980 | | | | | 985 | | | | | 990 | | |
| Ser | Leu | Leu | Ile | Asn | Ile | Gly | Asp | His | Pro | Lys | Asp | Ile | Tyr | Asp | Ala |
| | | 995 | | | | | 1000 | | | | | 1005 | | | |
| Phe | Asp | Ser | Tyr | Phe | Lys | Asp | Glu | Tyr | Leu | Thr | Met | Glu | Glu | Tyr | Gly |
| | 1010 | | | | | 1015 | | | | | 1020 | | | | |
| Asp | Val | Ile | Arg | Thr | Val | Ala | Val | Thr | Thr | Phe | Pro | Thr | Ile | Leu | Gln |
| 1025 | | | | | 1030 | | | | | 1035 | | | | | 1040 |
| Val | Gln | Ile | Gln | Arg | Val | Tyr | Tyr | Asp | Arg | Glu | Arg | Leu | Met | Pro | Phe |
| | | | | 1045 | | | | | 1050 | | | | | 1055 | |
| Lys | Ser | Ile | Glu | Pro | Leu | Pro | Phe | Lys | Glu | Val | Ile | Tyr | Met | Asp | Arg |
| | | | 1060 | | | | | 1065 | | | | | 1070 | | |
| Tyr | Ala | Asp | Thr | Glu | Asn | Pro | Leu | Leu | Leu | Ala | Lys | Lys | Lys | Glu | Thr |
| | | 1075 | | | | | 1080 | | | | | 1085 | | | |
| Glu | Glu | Met | Lys | Gln | Lys | Leu | Lys | Val | Met | Lys | Asn | Arg | Gln | Arg | Glu |
| | 1090 | | | | | 1095 | | | | | 1100 | | | | |
| Leu | Leu | Ser | Arg | Asp | Asp | Ser | Gly | Leu | Thr | Arg | Lys | Asp | Ala | Phe | Leu |
| 1105 | | | | | 1110 | | | | | 1115 | | | | | 1120 |
| Glu | Ser | Ile | Lys | Leu | Leu | Glu | Ser | Asp | Thr | Ile | Lys | Lys | Thr | Pro | Leu |
| | | | | 1125 | | | | | 1130 | | | | | 1135 | |
| Lys | Ile | Glu | Ala | Ala | Asn | Asp | Val | Ile | Lys | Thr | Leu | Arg | Asn | Asn | Val |
| | | | 1140 | | | | | 1145 | | | | | 1150 | | |
| Gln | Asn | Ile | Asp | Asn | Glu | Leu | Met | Lys | Leu | Tyr | Asn | Asp | Ile | Asn | Ser |
| | | 1155 | | | | | 1160 | | | | | 1165 | | | |
| Leu | Glu | Glu | Lys | Ile | Ser | His | Gln | Phe | Asp | Asp | Phe | Lys | Glu | Tyr | Gly |
| | 1170 | | | | | 1175 | | | | | 1180 | | | | |
| Tyr | Ser | Leu | Phe | Ser | Val | Phe | Ile | His | Arg | Gly | Glu | Ala | Ser | Tyr | Gly |
| 1185 | | | | | 1190 | | | | | 1195 | | | | | 1200 |
| His | Tyr | Trp | Ile | Tyr | Ile | Lys | Asp | Arg | Asn | Arg | Asn | Gly | Ile | Trp | Arg |
| | | | 1205 | | | | | 1210 | | | | | 1215 | | |
| Lys | Tyr | Asn | Asp | Glu | Thr | Ile | Ser | Glu | Val | Gln | Glu | Glu | Glu | Val | Phe |
| | | | 1220 | | | | | 1225 | | | | | 1230 | | |
| Asn | Phe | Asn | Glu | Gly | Asn | Thr | Ala | Thr | Pro | Tyr | Phe | Leu | Val | Tyr | Val |
| | | 1235 | | | | | 1240 | | | | | 1245 | | | |
| Lys | Gln | Gly | Gln | Glu | Gly | Asp | Ile | Glu | Pro | Leu | Lys | Arg | Ile | Leu | Lys |
| | | 1250 | | | | | 1255 | | | | | 1260 | | | |

( 2 ) INFORMATION FOR SEQ ID NO:7:

( i ) SEQUENCE CHARACTERISTICS:
        ( A ) LENGTH: 4887 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1278..4013

( x i ) SEQUENCE DESCRIPTION: SEQ ID NO:7:

| | | | | | |
|---|---|---|---|---|---|
| GCATGCTGAA | CATCCTTCTG | CAAACAACCT | TGCCACATAA | CGGGTATACC | AGGCAGGCGT | 60
| TCATCATCAC | GCCAACATAT | TTCTTGATCA | ACAATTGCTT | CACAGATGCG | GGATTCAAGG | 120
| GGAAAATGAC | CGCCATCAAC | GAGCAGGGCC | ACGACTCGAT | TGATTTCGAG | TCGTTGATTT | 180
| CTGCCCTTGA | GCAGCACGAG | GCGGAGCCGC | AGCCCCATAG | TACCACAGAG | ATGATTCAGG | 240
| GGCCAAAGTT | GACCAAGAAG | GTCTACAGGT | ACGTTATGTA | CTGCATCCCG | ACGTTTGCAA | 300
| ACCCATCGGG | AAACACATAC | TCGCTTGAGA | CCAGACGCAG | ACTTATCGAC | ATCGCTCGGA | 360
| AGTACGACAT | GCTGATAATC | ACTGATGACG | TGTACGATAT | TCTAGATTAC | ACGACGCCCT | 420
| CAGATGAGCT | GCCCTCTCCG | CCCCTAAGGA | TGGTGCACAT | AGACAGAAGT | ACAGCGCCCT | 480
| CCGGTGAGGA | CTCGTTCGGG | AATACAGTGT | CCAACGCAAC | TTTCTCCAAG | CTGATCGCCC | 540
| CTGGGCTCAG | ATTTGGATAC | CATGAGTCAA | TCAACGCGAA | TCTCGCCAGA | CAGCTATCTA | 600
| AAGGTGGTGC | AAACGTCTCT | GGCGGAACTC | CCTCACAACT | GAACTCCATG | ATCGTGGGTG | 660
| AGATGCTGCG | TAGTGGTGCC | GCCCAGAGAT | GCATTGCACA | TCTGAGATCC | GTATACTCCG | 720
| AGAGGGCCAC | TGTCTTGACC | TCGGCGCTTA | AGAAATACAT | GCCCCATGGA | ACCGAGATTA | 780
| TGCCATTGAA | GGGCGGCTAT | TTTACTTGGA | TCACTCTCCC | ACCAGCGTAC | AATGCCATGG | 840
| AGATATCCAC | TATTCTTGCC | AAGAAATTTA | ATGTCATCCT | TGCCGACGGC | TCCAATTTCG | 900
| AGGTCATCGG | CGATGAGAAA | AACTGGGGTC | AGTCATGCTT | TAGGCTTTCT | ATTAGTTTCT | 960
| TAGAAGTTGA | TGATATCGAC | AGGGGCATTG | AGCTGTTTGG | AGCTGTTTGC | AAATCTCATG | 1020
| CGATCACCAA | TAACATAACT | ATGTAGAAGG | AATACGTATA | TAGGTGAACG | GTAATAAGAG | 1080
| GGTAATTTTT | CTACGGGCAA | AGGCAAGGAA | GAAAAGAAA | AAGAAGGAAA | AAAATATAAT | 1140
| GTGATAAAAC | AAACAAGCAG | CGAAAAAGCG | AAAGGGAAGA | GAAGTGTTCT | AGAGAAGAAA | 1200
| GTCATTTTAA | TAGTAAGTCA | GACTCGTCTG | CTACCATCAT | CCAGGTACCG | CTTTCCTTTC | 1260
| CATCATCATT | AAAAAAA ATG | AAC ATG CAA | GAC GCT AAC | AAA GAA GAG TCG | 1310

| | | | | | | | | | | |
|---|---|---|---|---|---|---|---|---|---|---|
| | | | | | | | | | Met Asn Met Gln Asp Ala Asn Lys Glu Glu Ser | |
| | | | | | | | | | 1 5 10 | |

| TAC | TCG | ATG | TAC | CCG | AAA | ACC | TCT | TCT | CCA | CCA | CCA | CCT | ACG | CCA | ACC | 1358 |
|---|---|---|---|---|---|---|---|---|---|---|---|---|---|---|---|---|
| Tyr | Ser | Met | Tyr | Pro | Lys | Thr | Ser | Ser | Pro | Pro | Pro | Pro | Thr | Pro | Thr | |
| | | | 15 | | | | 20 | | | | | 25 | | | | |

| AAT | ATG | CAG | ATT | CCT | ATT | TAT | CAA | GCG | CCT | TTG | CAG | ATG | TAC | GGC | TAC | 1406 |
|---|---|---|---|---|---|---|---|---|---|---|---|---|---|---|---|---|
| Asn | Met | Gln | Ile | Pro | Ile | Tyr | Gln | Ala | Pro | Leu | Gln | Met | Tyr | Gly | Tyr | |
| | | 30 | | | | | 35 | | | | | | 40 | | | |

| ACT | CAG | GCC | CCA | TAT | CTA | TAC | CCC | ACA | CAA | ATA | CCT | GCC | TAT | TCG | TTT | 1454 |
|---|---|---|---|---|---|---|---|---|---|---|---|---|---|---|---|---|
| Thr | Gln | Ala | Pro | Tyr | Leu | Tyr | Pro | Thr | Gln | Ile | Pro | Ala | Tyr | Ser | Phe | |
| | | 45 | | | | 50 | | | | | 55 | | | | | |

| AAT | ATG | GTC | AAC | CAA | AAC | CAG | CCA | ATC | TAC | CAT | CAA | AGT | GGC | AGC | CCA | 1502 |
|---|---|---|---|---|---|---|---|---|---|---|---|---|---|---|---|---|
| Asn | Met | Val | Asn | Gln | Asn | Gln | Pro | Ile | Tyr | His | Gln | Ser | Gly | Ser | Pro | |
| 60 | | | | | 65 | | | | | 70 | | | | | 75 | |

| CAT | CAC | TTG | CCT | CCG | CAA | AAC | AAT | ATT | AAC | GGC | GGA | AGC | ACT | ACC | AAT | 1550 |
|---|---|---|---|---|---|---|---|---|---|---|---|---|---|---|---|---|
| His | His | Leu | Pro | Pro | Gln | Asn | Asn | Ile | Asn | Gly | Gly | Ser | Thr | Thr | Asn | |
| | | | | 80 | | | | | 85 | | | | | 90 | | |

| AAC | AAC | AAC | ATT | AAC | AAG | AAG | AAG | TGG | CAC | TCT | AAT | GGC | ATT | ACC | AAT | 1598 |
|---|---|---|---|---|---|---|---|---|---|---|---|---|---|---|---|---|
| Asn | Asn | Asn | Ile | Asn | Lys | Lys | Lys | Trp | His | Ser | Asn | Gly | Ile | Thr | Asn | |
| | | | | 95 | | | | 100 | | | | | 105 | | | |

| AAC | AAT | GGA | AGC | AGC | GGT | AAT | CAA | GGC | GCC | AAC | TCT | AGC | GGT | AGC | GGC | 1646 |
|---|---|---|---|---|---|---|---|---|---|---|---|---|---|---|---|---|
| Asn | Asn | Gly | Ser | Ser | Gly | Asn | Gln | Gly | Ala | Asn | Ser | Ser | Gly | Ser | Gly | |
| | | 110 | | | | | 115 | | | | | 120 | | | | |

| ATG | AGC | TAC | AAC | AAA | TCC | CAC | ACC | TAC | CAT | CAC | AAT | TAC | TCT | AAC | AAT | 1694 |
|---|---|---|---|---|---|---|---|---|---|---|---|---|---|---|---|---|
| Met | Ser | Tyr | Asn | Lys | Ser | His | Thr | Tyr | His | His | Asn | Tyr | Ser | Asn | Asn | |
| | 125 | | | | | 130 | | | | | 135 | | | | | |

| CAT | ATC | CCC | ATG | ATG | GCC | TCT | CCA | AAC | AGT | GGC | AGC | AAT | GCG | GGC | ATG | 1742 |

55

-continued

| | | | | | | | | | | | | | | | | |
|---|---|---|---|---|---|---|---|---|---|---|---|---|---|---|---|---|
| His | Ile | Pro | Met | Met | Ala | Ser | Pro | Asn | Ser | Gly | Ser | Asn | Ala | Gly | Met | |
| 140 | | | | 145 | | | | | 150 | | | | | 155 | | |

```
AAA AAA CAG ACC AAC TCT TCC AAC GGC AAC GGT TCT TCG GCT ACT TCA          1790
Lys Lys Gln Thr Asn Ser Ser Asn Gly Asn Gly Ser Ser Ala Thr Ser
                160             165             170

CCA TCG TAC TCT TCC TAC AAC TCT TCT TCA CAG TAT GAT TTA TAC AAG          1838
Pro Ser Tyr Ser Ser Tyr Asn Ser Ser Ser Gln Tyr Asp Leu Tyr Lys
            175             180             185

TTT GAT GTC ACT AAA TTA AAG AAT CTC AAG GAA AAT TCA TCA AAC TTG          1886
Phe Asp Val Thr Lys Leu Lys Asn Leu Lys Glu Asn Ser Ser Asn Leu
        190             195             200

ATT CAA TTG CCA CTG TTC ATA AAC ACT ACG GAA GCA GAA TTT GCT GCG          1934
Ile Gln Leu Pro Leu Phe Ile Asn Thr Thr Glu Ala Glu Phe Ala Ala
    205             210             215

GCA AGT GTC CAA AGG TAC GAA TTA AAC ATG AAG GCT TTG AAC CTA AAC          1982
Ala Ser Val Gln Arg Tyr Glu Leu Asn Met Lys Ala Leu Asn Leu Asn
220             225             230             235

TCT GAA AGC TTA GAG AAC TCA TCT GTA GAA AAG AGC TCT GCC CAT CAT          2030
Ser Glu Ser Leu Glu Asn Ser Ser Val Glu Lys Ser Ser Ala His His
            240             245             250

CAC ACA AAA AGC CAT AGT ATA CCA AAG CAT AAT GAG GAA GTA AAG ACA          2078
His Thr Lys Ser His Ser Ile Pro Lys His Asn Glu Glu Val Lys Thr
        255             260             265

GAA ACA CAT GGG GAA GAA GAA GAT GCT CAT GAT AAA AAA CCA CAT GCG          2126
Glu Thr His Gly Glu Glu Glu Asp Ala His Asp Lys Lys Pro His Ala
    270             275             280

AGC AAA GAT GCG CAC GAG CTT AAA AAG AAA ACT GAA GTA AAG AAA GAG          2174
Ser Lys Asp Ala His Glu Leu Lys Lys Lys Thr Glu Val Lys Lys Glu
285             290             295

GAT GCT AAG CAA GAC CGT AAC GAA AAA GTT ATA CAG GAA CCT CAA GCT          2222
Asp Ala Lys Gln Asp Arg Asn Glu Lys Val Ile Gln Glu Pro Gln Ala
300             305             310             315

ACT GTT TTA CCT GTA GTG GAT AAG AAG GAA CCA GAG GAA TCT GTT GAA          2270
Thr Val Leu Pro Val Val Asp Lys Lys Glu Pro Glu Glu Ser Val Glu
            320             325             330

GAA AAT ACT TCC AAG ACA TCT TCA CCT TCA CCA TCT CCT CCA GCA GCA          2318
Glu Asn Thr Ser Lys Thr Ser Ser Pro Ser Pro Ser Pro Pro Ala Ala
        335             340             345

AAA TCC TGG TCC GCC ATA GCA TCA GAT GCG ATT AAA AGT AGA CAA GCT          2366
Lys Ser Trp Ser Ala Ile Ala Ser Asp Ala Ile Lys Ser Arg Gln Ala
    350             355             360

AGT AAC AAA ACA GTC TCC GGA TCG ATG GTC ACT AAA ACA CCA ATT TCT          2414
Ser Asn Lys Thr Val Ser Gly Ser Met Val Thr Lys Thr Pro Ile Ser
365             370             375

GGT ACG ACC GCA GGC GTT TCA TCA ACA AAC ATG GCT GCG GCG ACT ATA          2462
Gly Thr Thr Ala Gly Val Ser Ser Thr Asn Met Ala Ala Ala Thr Ile
380             385             390             395

GGT AAA TCC AGC TCT CCC CTG TTG TCC AAG CAG CCT CAG AAA AAG GAT          2510
Gly Lys Ser Ser Ser Pro Leu Leu Ser Lys Gln Pro Gln Lys Lys Asp
            400             405             410

AAA AAA TAC GTT CCA CCT TCT ACA AAG GGT ATT GAG CCA CTG GGT TCG          2558
Lys Lys Tyr Val Pro Pro Ser Thr Lys Gly Ile Glu Pro Leu Gly Ser
        415             420             425

ATT GCG TTA AGA ATG TGT TTT GAT CCC GAT TTC ATT AGT TAC GTT TTA          2606
Ile Ala Leu Arg Met Cys Phe Asp Pro Asp Phe Ile Ser Tyr Val Leu
    430             435             440

CGG AAT AAA GAT GTT GAA AAC AAA ATA CCA GTC CAT TCC ATT ATT CCA          2654
Arg Asn Lys Asp Val Glu Asn Lys Ile Pro Val His Ser Ile Ile Pro
445             450             455

AGA GGC ATA ATT AAC AGA GCC AAC ATT TGT TTT ATG AGT TCT GTG TTA          2702
Arg Gly Ile Ile Asn Arg Ala Asn Ile Cys Phe Met Ser Ser Val Leu
460             465             470             475
```

|     |     |     |     |     |     |     |     |     |     |     |     |     |     |     |     |     |
|---|---|---|---|---|---|---|---|---|---|---|---|---|---|---|---|---|
| CAA | GTG | TTA | CTC | TAC | TGT | AAG | CCA | TTT | ATT | GAT | GTA | ATT | AAC | GTT | CTC | 2750 |
| Gln | Val | Leu | Leu | Tyr | Cys | Lys | Pro | Phe | Ile | Asp | Val | Ile | Asn | Val | Leu | |
| | | | | 480 | | | | 485 | | | | | 490 | | | |
| AGT | ACA | CGG | AAT | ACC | AAT | TCA | AGA | GTC | GGC | ACA | TCA | TCC | TGT | AAA | TTA | 2798 |
| Ser | Thr | Arg | Asn | Thr | Asn | Ser | Arg | Val | Gly | Thr | Ser | Ser | Cys | Lys | Leu | |
| | | | 495 | | | | | 500 | | | | 505 | | | | |
| TTA | GAT | GCT | TGT | TTG | ACT | ATG | TAT | AAG | CAA | TTC | GAT | AAG | GAA | ACC | TAT | 2846 |
| Leu | Asp | Ala | Cys | Leu | Thr | Met | Tyr | Lys | Gln | Phe | Asp | Lys | Glu | Thr | Tyr | |
| | | 510 | | | | | 515 | | | | | 520 | | | | |
| GAG | AAA | AAA | TTC | CTA | GAG | AAT | GCT | GAT | GAT | GCT | GAA | AAA | ACC | ACG | GAA | 2894 |
| Glu | Lys | Lys | Phe | Leu | Glu | Asn | Ala | Asp | Asp | Ala | Glu | Lys | Thr | Thr | Glu | |
| | 525 | | | | | 530 | | | | | 535 | | | | | |
| AGT | GAT | GCA | AAA | AAA | TCA | TCA | AAA | TCC | AAG | AGT | TTC | CAA | CAC | TGC | GCC | 2942 |
| Ser | Asp | Ala | Lys | Lys | Ser | Ser | Lys | Ser | Lys | Ser | Phe | Gln | His | Cys | Ala | |
| 540 | | | | | 545 | | | | | 550 | | | | | 555 | |
| ACT | GCC | GAT | GCT | GTC | AAA | CCT | GAC | GAA | TTT | TAC | AAA | ACT | TTG | TCT | ACT | 2990 |
| Thr | Ala | Asp | Ala | Val | Lys | Pro | Asp | Glu | Phe | Tyr | Lys | Thr | Leu | Ser | Thr | |
| | | | | 560 | | | | | 565 | | | | | 570 | | |
| ATA | CCG | AAG | TTC | AAA | GAC | TTG | CAA | TGG | GGC | CAT | CAG | GAA | GAC | GCA | GAA | 3038 |
| Ile | Pro | Lys | Phe | Lys | Asp | Leu | Gln | Trp | Gly | His | Gln | Glu | Asp | Ala | Glu | |
| | | | 575 | | | | | 580 | | | | | 585 | | | |
| GAA | TTT | TTG | ACC | CAC | TTA | TTG | GAC | CAA | TTA | CAC | GAG | GAA | TTA | ATT | TCT | 3086 |
| Glu | Phe | Leu | Thr | His | Leu | Leu | Asp | Gln | Leu | His | Glu | Glu | Leu | Ile | Ser | |
| | | 590 | | | | | 595 | | | | | 600 | | | | |
| GCA | ATT | GAT | GGC | TTA | ACC | GAT | AAT | GAA | ATT | CAA | AAT | ATG | CTG | CAA | AGT | 3134 |
| Ala | Ile | Asp | Gly | Leu | Thr | Asp | Asn | Glu | Ile | Gln | Asn | Met | Leu | Gln | Ser | |
| | 605 | | | | | 610 | | | | | 615 | | | | | |
| ATT | AAT | GAT | GAA | CAA | TTG | AAA | GTT | TTC | TTT | ATT | AGA | AAT | TTG | TCA | CGT | 3182 |
| Ile | Asn | Asp | Glu | Gln | Leu | Lys | Val | Phe | Phe | Ile | Arg | Asn | Leu | Ser | Arg | |
| 620 | | | | | 625 | | | | | 630 | | | | | 635 | |
| TAT | GGA | AAA | GCA | GAG | TTT | ATC | AAA | AAT | GCT | AGT | CCT | AGA | CTG | AAG | GAG | 3230 |
| Tyr | Gly | Lys | Ala | Glu | Phe | Ile | Lys | Asn | Ala | Ser | Pro | Arg | Leu | Lys | Glu | |
| | | | | 640 | | | | | 645 | | | | | 650 | | |
| TTG | ATA | GAA | AAA | TAT | GGC | GTG | ATC | AAT | GAT | GAC | TCT | ACC | GAA | GAA | AAT | 3278 |
| Leu | Ile | Glu | Lys | Tyr | Gly | Val | Ile | Asn | Asp | Asp | Ser | Thr | Glu | Glu | Asn | |
| | | | 655 | | | | | 660 | | | | | 665 | | | |
| GGT | TGG | CAT | GAA | GTG | AGC | GGA | TCT | AGC | AAA | AGA | GGC | AAG | AAA | ACT | AAG | 3326 |
| Gly | Trp | His | Glu | Val | Ser | Gly | Ser | Ser | Lys | Arg | Gly | Lys | Lys | Thr | Lys | |
| | | 670 | | | | | 675 | | | | | 680 | | | | |
| ACC | GCT | GCC | AAG | AGG | ACT | GTC | GAG | ATT | GTT | CCA | TCA | CCA | ATC | TCC | AAA | 3374 |
| Thr | Ala | Ala | Lys | Arg | Thr | Val | Glu | Ile | Val | Pro | Ser | Pro | Ile | Ser | Lys | |
| | 685 | | | | | 690 | | | | | 695 | | | | | |
| CTT | TTC | GGT | GGC | CAG | TTC | AGA | TCT | GTG | TTA | GAT | ATA | CCG | AAC | AAT | AAG | 3422 |
| Leu | Phe | Gly | Gly | Gln | Phe | Arg | Ser | Val | Leu | Asp | Ile | Pro | Asn | Asn | Lys | |
| 700 | | | | | 705 | | | | | 710 | | | | | 715 | |
| GAA | TCT | CAA | TCG | ATT | ACA | CTC | GAT | CCG | TTC | CAA | ACA | ATT | CAA | TTG | GAC | 3470 |
| Glu | Ser | Gln | Ser | Ile | Thr | Leu | Asp | Pro | Phe | Gln | Thr | Ile | Gln | Leu | Asp | |
| | | | | 720 | | | | | 725 | | | | | 730 | | |
| ATT | TCA | GAT | GCT | GGT | GTG | AAT | GAT | CTA | GAA | ACT | GCA | TTC | AAA | AAA | TTT | 3518 |
| Ile | Ser | Asp | Ala | Gly | Val | Asn | Asp | Leu | Glu | Thr | Ala | Phe | Lys | Lys | Phe | |
| | | | 735 | | | | | 740 | | | | | 745 | | | |
| AGT | GAA | TAC | GAA | TTG | CTA | CCC | TTT | AAG | TCC | TCG | TCA | GGG | AAT | GAT | GTC | 3566 |
| Ser | Glu | Tyr | Glu | Leu | Leu | Pro | Phe | Lys | Ser | Ser | Ser | Gly | Asn | Asp | Val | |
| | | | | 750 | | | | | 755 | | | | | 760 | | |
| GAG | GCC | AAG | AAG | CAG | ACT | TTT | ATT | GAT | AAA | TTG | CCG | CAA | GTT | CTT | TTA | 3614 |
| Glu | Ala | Lys | Lys | Gln | Thr | Phe | Ile | Asp | Lys | Leu | Pro | Gln | Val | Leu | Leu | |
| | 765 | | | | | 770 | | | | | 775 | | | | | |
| ATC | CAA | TTC | AAA | AGA | TTC | TCA | TTC | ATA | AAT | AAT | GTG | AAC | AAA | GAC | AAC | 3662 |
| Ile | Gln | Phe | Lys | Arg | Phe | Ser | Phe | Ile | Asn | Asn | Val | Asn | Lys | Asp | Asn | |
| 780 | | | | | 785 | | | | | 790 | | | | | 795 | |
| GCA | ATG | ACG | AAC | TAT | AAC | GCG | TAC | AAT | GGA | CGT | ATT | GAG | AAG | ATC | AGG | 3710 |

| | | | | | | | | | | | | | | |
|---|---|---|---|---|---|---|---|---|---|---|---|---|---|---|
| Ala | Met | Thr | Asn | Tyr | Asn | Ala | Tyr | Asn | Gly | Arg | Ile | Glu | Lys | Ile | Arg |
| | | | | 800 | | | | | 805 | | | | | 810 | |

| AAA | AAA | ATT | AAA | TAT | GGT | CAC | GAG | TTA | ATC | ATA | CCT | GAA | GAA | TCA | ATG | 3758 |
|---|---|---|---|---|---|---|---|---|---|---|---|---|---|---|---|---|
| Lys | Lys | Ile | Lys | Tyr | Gly | His | Glu | Leu | Ile | Ile | Pro | Glu | Glu | Ser | Met |  |
| | | | 815 | | | | 820 | | | | | 825 | | | | |

| TCT | TCC | ATA | ACA | TTG | AAA | AAC | AAC | ACC | TCA | GGG | ATT | GAT | GAT | AGA | AGA | 3806 |
|---|---|---|---|---|---|---|---|---|---|---|---|---|---|---|---|---|
| Ser | Ser | Ile | Thr | Leu | Lys | Asn | Asn | Thr | Ser | Gly | Ile | Asp | Asp | Arg | Arg |  |
| | | 830 | | | | | 835 | | | | | 840 | | | | |

| TAT | AAG | CTA | ACC | GGA | GTT | ATA | TAC | CAT | CAT | GGG | GTA | AGT | TCC | GAT | GGC | 3854 |
|---|---|---|---|---|---|---|---|---|---|---|---|---|---|---|---|---|
| Tyr | Lys | Leu | Thr | Gly | Val | Ile | Tyr | His | His | Gly | Val | Ser | Ser | Asp | Gly |  |
| | 845 | | | | | 850 | | | | | 855 | | | | | |

| GGT | CAT | TAC | ACA | GCG | GAT | GTT | TAT | CAT | AGC | GAG | CAC | AAC | AAA | TGG | TAT | 3902 |
|---|---|---|---|---|---|---|---|---|---|---|---|---|---|---|---|---|
| Gly | His | Tyr | Thr | Ala | Asp | Val | Tyr | His | Ser | Glu | His | Asn | Lys | Trp | Tyr |  |
| 860 | | | | | 865 | | | | | 870 | | | | | 875 | |

| AGA | ATA | GAT | GAT | GTA | AAT | ATT | ACC | GAA | CTA | GAG | GAC | GAT | GAC | GTT | TTG | 3950 |
|---|---|---|---|---|---|---|---|---|---|---|---|---|---|---|---|---|
| Arg | Ile | Asp | Asp | Val | Asn | Ile | Thr | Glu | Leu | Glu | Asp | Asp | Asp | Val | Leu |  |
| | | | | 880 | | | | | 885 | | | | | 890 | | |

| AAA | GGT | GGC | GAA | GAA | GCT | TCT | GAT | TCG | AGG | ACT | GCC | TAT | ATT | TTA | ATG | 3998 |
|---|---|---|---|---|---|---|---|---|---|---|---|---|---|---|---|---|
| Lys | Gly | Gly | Glu | Glu | Ala | Ser | Asp | Ser | Arg | Thr | Ala | Tyr | Ile | Leu | Met |  |
| | | | 895 | | | | | 900 | | | | | 905 | | | |

| TAT | CAA | AAG | AGA | AAT | TAAGACGGGG | GGTGGTATTA | TAGACAAAAT | ACATAAAAAA | 4053 |
|---|---|---|---|---|---|---|---|---|---|
| Tyr | Gln | Lys | Arg | Asn | | | | | |
| | | 910 | | | | | | | |

| TAATATAGCA | ATAATACAAT | ACAATACAAT | ACAATACGAT | AGTGAGCACG | ATTTTAAAAA | 4113 |
|---|---|---|---|---|---|---|
| AGAAATAGAG | ACAGACAGAG | AAACAGAGTT | ACACTTTATG | CTTGGCATAT | TTAAAAAATG | 4173 |
| ATTTCGCCCA | GGATCGAACT | GGGGACGTTC | TGCGTGTTAA | GCAGATGCCA | TAACCGACTA | 4233 |
| GACCACGAAA | CCAATTATTT | CTTGGAGATG | AACATTTAAG | AAACAAATAC | CTTGTAGAAG | 4293 |
| GAATGTGAAT | TTCAAAATAT | TATGGCCTTT | GGCAACAATG | GAATCACAAC | AATTATCACA | 4353 |
| AAACTCATAC | ATCTCTTAAG | ATTCATTTCT | TACTTTAAGT | AATCATCCAA | ATTTAGCCAA | 4413 |
| AGTTTGATTT | TACCTAAAAA | AAGCAGAGGA | TTCCCGATTT | CAATCATATG | TGCACAGACG | 4473 |
| ATGAGTCCAA | CACGTTATCG | TTAACATAGT | GCTCAATATT | GCCACTGCGC | TTCGCAGGAG | 4533 |
| CATATTTCGT | ATACGCCAAG | CCCAAGGAGG | GTTTTGTCAT | TAAGCAGCTT | ACGCCAATTA | 4593 |
| AGTGCTAACC | TCGAAGCACC | ATACTTTATC | TCAGGATTTA | CAAACTCCCT | ATTGCACAAC | 4653 |
| GGCAAACAAC | ATAATCATGA | CCAAATGGGT | AAAAAGATG | AGCTGTGAAA | AAGCCAAAAA | 4713 |
| AAAAAAGGAA | GAACTAGAAT | TACATTTATT | ATTCTACACA | CAAAAAGAAA | AAATAGTTTC | 4773 |
| TTTATTTAAA | TGATTTGAAG | AAAAAGAACT | ATAACGACTA | CATCGAAGAA | TACAATATTA | 4833 |
| GTAAAAAACA | CATGTCCTGT | TTAAAATAAG | TCTCTAGTTA | AAGACTATTC | GATC | 4887 |

( 2 ) INFORMATION FOR SEQ ID NO:8:

( i ) SEQUENCE CHARACTERISTICS:
        ( A ) LENGTH: 912 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Met | Asn | Met | Gln | Asp | Ala | Asn | Lys | Glu | Glu | Ser | Tyr | Ser | Met | Tyr | Pro |
|---|---|---|---|---|---|---|---|---|---|---|---|---|---|---|---|
| 1 | | | | 5 | | | | | 10 | | | | | 15 | |

| Lys | Thr | Ser | Ser | Pro | Pro | Pro | Thr | Pro | Thr | Asn | Met | Gln | Ile | Pro |
|---|---|---|---|---|---|---|---|---|---|---|---|---|---|---|
| | | | 20 | | | | 25 | | | | | 30 | | |

| Ile | Tyr | Gln | Ala | Pro | Leu | Gln | Met | Tyr | Gly | Tyr | Thr | Gln | Ala | Pro | Tyr |
|---|---|---|---|---|---|---|---|---|---|---|---|---|---|---|---|
| | | | 35 | | | | 40 | | | | | 45 | | | |

| Leu | Tyr | Pro | Thr | Gln | Ile | Pro | Ala | Tyr | Ser | Phe | Asn | Met | Val | Asn | Gln |
|---|---|---|---|---|---|---|---|---|---|---|---|---|---|---|---|
| | 50 | | | | | 55 | | | | | 60 | | | | |

```
Asn Gln Pro Ile Tyr His Gln Ser Gly Ser Pro His His Leu Pro Pro
 65                  70                  75                   80

Gln Asn Asn Ile Asn Gly Gly Ser Thr Thr Asn Asn Asn Asn Ile Asn
             85                  90                  95

Lys Lys Lys Trp His Ser Asn Gly Ile Thr Asn Asn Asn Gly Ser Ser
            100             105             110

Gly Asn Gln Gly Ala Asn Ser Ser Gly Ser Gly Met Ser Tyr Asn Lys
            115             120             125

Ser His Thr Tyr His His Asn Tyr Ser Asn Asn His Ile Pro Met Met
    130             135             140

Ala Ser Pro Asn Ser Gly Ser Asn Ala Gly Met Lys Lys Gln Thr Asn
145             150             155                         160

Ser Ser Asn Gly Asn Gly Ser Ser Ala Thr Ser Pro Ser Tyr Ser Ser
            165             170             175

Tyr Asn Ser Ser Ser Gln Tyr Asp Leu Tyr Lys Phe Asp Val Thr Lys
            180             185             190

Leu Lys Asn Leu Lys Glu Asn Ser Ser Asn Leu Ile Gln Leu Pro Leu
            195             200             205

Phe Ile Asn Thr Thr Glu Ala Glu Phe Ala Ala Ala Ser Val Gln Arg
210             215             220

Tyr Glu Leu Asn Met Lys Ala Leu Asn Leu Asn Ser Glu Ser Leu Glu
225             230             235             240

Asn Ser Ser Val Glu Lys Ser Ser Ala His His His Thr Lys Ser His
            245             250             255

Ser Ile Pro Lys His Asn Glu Glu Val Lys Thr Glu Thr His Gly Glu
            260             265             270

Glu Glu Asp Ala His Asp Lys Lys Pro His Ala Ser Lys Asp Ala His
        275             280             285

Glu Leu Lys Lys Lys Thr Glu Val Lys Lys Glu Asp Ala Lys Gln Asp
290             295             300

Arg Asn Glu Lys Val Ile Gln Glu Pro Gln Ala Thr Val Leu Pro Val
305             310             315             320

Val Asp Lys Lys Glu Pro Glu Glu Ser Val Glu Glu Asn Thr Ser Lys
            325             330             335

Thr Ser Ser Pro Ser Pro Ser Pro Pro Ala Ala Lys Ser Trp Ser Ala
            340             345             350

Ile Ala Ser Asp Ala Ile Lys Ser Arg Gln Ala Ser Asn Lys Thr Val
            355             360             365

Ser Gly Ser Met Val Thr Lys Thr Pro Ile Ser Gly Thr Thr Ala Gly
            370             375             380

Val Ser Ser Thr Asn Met Ala Ala Ala Thr Ile Gly Lys Ser Ser Ser
385             390             395             400

Pro Leu Leu Ser Lys Gln Pro Gln Lys Lys Asp Lys Lys Tyr Val Pro
            405             410             415

Pro Ser Thr Lys Gly Ile Glu Pro Leu Gly Ser Ile Ala Leu Arg Met
            420             425             430

Cys Phe Asp Pro Asp Phe Ile Ser Tyr Val Leu Arg Asn Lys Asp Val
            435             440             445

Glu Asn Lys Ile Pro Val His Ser Ile Ile Pro Arg Gly Ile Ile Asn
450                 455             460

Arg Ala Asn Ile Cys Phe Met Ser Ser Val Leu Gln Val Leu Leu Tyr
465             470             475             480

Cys Lys Pro Phe Ile Asp Val Ile Asn Val Leu Ser Thr Arg Asn Thr
            485             490             495
```

| | | | | | | | | | | | | | | |
|---|---|---|---|---|---|---|---|---|---|---|---|---|---|---|
| Asn | Ser | Arg | Val 500 | Gly | Thr | Ser | Ser | Cys 505 | Lys | Leu | Leu | Asp | Ala 510 | Cys | Leu |
| Thr | Met | Tyr 515 | Lys | Gln | Phe | Asp | Lys 520 | Glu | Thr | Tyr | Glu | Lys 525 | Lys | Phe | Leu |
| Glu | Asn 530 | Ala | Asp | Asp | Ala | Glu 535 | Lys | Thr | Thr | Glu | Ser 540 | Asp | Ala | Lys | Lys |
| Ser 545 | Ser | Lys | Ser | Lys | Ser 550 | Phe | Gln | His | Cys | Ala 555 | Thr | Ala | Asp | Ala | Val 560 |
| Lys | Pro | Asp | Glu | Phe 565 | Tyr | Lys | Thr | Leu | Ser 570 | Thr | Ile | Pro | Lys | Phe 575 | Lys |
| Asp | Leu | Gln | Trp 580 | Gly | His | Gln | Glu | Asp 585 | Ala | Glu | Glu | Phe | Leu 590 | Thr | His |
| Leu | Leu | Asp 595 | Gln | Leu | His | Glu | Glu 600 | Leu | Ile | Ser | Ala | Ile 605 | Asp | Gly | Leu |
| Thr | Asp 610 | Asn | Glu | Ile | Gln | Asn 615 | Met | Leu | Gln | Ser | Ile 620 | Asn | Asp | Glu | Gln |
| Leu 625 | Lys | Val | Phe | Phe | Ile 630 | Arg | Asn | Leu | Ser | Arg 635 | Tyr | Gly | Lys | Ala | Glu 640 |
| Phe | Ile | Lys | Asn | Ala 645 | Ser | Pro | Arg | Leu | Lys 650 | Glu | Leu | Ile | Glu | Lys 655 | Tyr |
| Gly | Val | Ile | Asn 660 | Asp | Asp | Ser | Thr | Glu 665 | Glu | Asn | Gly | Trp | His 670 | Glu | Val |
| Ser | Gly | Ser 675 | Ser | Lys | Arg | Gly | Lys 680 | Lys | Thr | Lys | Thr | Ala 685 | Ala | Lys | Arg |
| Thr | Val 690 | Glu | Ile | Val | Pro | Ser 695 | Pro | Ile | Ser | Lys | Leu 700 | Phe | Gly | Gly | Gln |
| Phe 705 | Arg | Ser | Val | Leu | Asp 710 | Ile | Pro | Asn | Asn | Lys 715 | Glu | Ser | Gln | Ser | Ile 720 |
| Thr | Leu | Asp | Pro | Phe 725 | Gln | Thr | Ile | Gln | Leu 730 | Asp | Ile | Ser | Asp | Ala 735 | Gly |
| Val | Asn | Asp | Leu 740 | Glu | Thr | Ala | Phe | Lys 745 | Lys | Phe | Ser | Glu | Tyr 750 | Glu | Leu |
| Leu | Pro | Phe 755 | Lys | Ser | Ser | Ser | Gly 760 | Asn | Asp | Val | Glu | Ala 765 | Lys | Lys | Gln |
| Thr | Phe 770 | Ile | Asp | Lys | Leu | Pro 775 | Gln | Val | Leu | Leu | Ile 780 | Gln | Phe | Lys | Arg |
| Phe 785 | Ser | Phe | Ile | Asn | Asn 790 | Val | Asn | Lys | Asp | Asn 795 | Ala | Met | Thr | Asn | Tyr 800 |
| Asn | Ala | Tyr | Asn | Gly 805 | Arg | Ile | Glu | Lys | Ile 810 | Arg | Lys | Lys | Ile | Lys 815 | Tyr |
| Gly | His | Glu | Leu 820 | Ile | Ile | Pro | Glu | Glu 825 | Ser | Met | Ser | Ser | Ile 830 | Thr | Leu |
| Lys | Asn | Asn 835 | Thr | Ser | Gly | Ile | Asp 840 | Asp | Arg | Arg | Tyr | Lys 845 | Leu | Thr | Gly |
| Val | Ile | Tyr 850 | His | His | Gly | Val 855 | Ser | Ser | Asp | Gly | Gly 860 | His | Tyr | Thr | Ala |
| Asp 865 | Val | Tyr | His | Ser | Glu 870 | His | Asn | Lys | Trp | Tyr 875 | Arg | Ile | Asp | Asp | Val 880 |
| Asn | Ile | Thr | Glu | Leu 885 | Glu | Asp | Asp | Val 890 | Leu | Lys | Gly | Gly | Glu 895 | Glu |
| Ala | Ser | Asp | Ser 900 | Arg | Thr | Ala | Tyr | Ile 905 | Leu | Met | Tyr | Gln | Lys 910 | Arg | Asn |

NUCLEIC ACID ENCODING UBIQUITIN-SPECIFIC PROTEASES

GOVERNMENT FUNDING

This invention was partially supported by the U.S. Government and the government has certain rights to the invention.

RELATED APPLICATIONS

This is a continuation-in-part application of U.S. Ser. No. 07/573,958 abandoned filed Aug. 28, 1990; which is a continuation-in-part application of U.S. Ser. No. 07/521,089 abandoned filed May 9, 1990.

BACKGROUND OF THE INVENTION

Ubiquitin (Ub), a highly conserved 76-residue protein, is present in eukaryotic cells either free or covalently joined to a great variety of proteins. The posttranslational coupling of ubiquitin to other proteins is catalyzed by a family of Ub-conjugating (E2) enzymes and involves formation of an isopeptide bond between the C-terminal Gly residue of ubiquitin and the ε-amino group of a Lys residue in an acceptor protein. One function of ubiquitin is to mark proteins destined for selective degradation. Ubiquitin was also shown to have a chaperone function, in that its transient (cotranslational) covalent association with specific ribosomal proteins promotes the assembly of ribosomal subunits.

Unlike branched Ub-protein conjugates, which are formed posttranslationally, linear Ub-protein adducts are formed as the translational products of natural or engineered gene fusions. Thus, in the yeast *Saccharomyces cerevisiae* for example, ubiquitin is generated exclusively by proteolytic processing of precursors in which ubiquitin is joined either to itself, as in the linear polyubiquitin protein Ubi4, or to unrelated amino acid sequences, as in the hybrid proteins Ubi1-Ubi3. In growing yeast cells, ubiquitin is generated largely from the Ubi1-Ubi3 precursors whose "tails" are specific ribosomal proteins. The polyubiquitin (UBI4) gene is dispensable in growing cells but becomes essential (as the main supplier of ubiquitin) during stress. The lack of genes encoding mature ubiquitin, and the fusion structure of ubiquitin precursors in yeast are characteristic of other eukaryotes as well.

Ub-specific, ATP-independent proteases capable of cleaving ubiquitin from its linear or branched conjugates have been detected in all eukarotes examined but not in bacteria such as *Escherichia coli*, which lack ubiquitin and Ub-specific enzymes. Miller et al. (*Biotechnology* 1: 698-704 (1989)) have cloned a *S. cerevisiae* gene, named YUH1, encoding a Ub-specific protease that cleaves ubiquitin from its relatively short C-terminal extensions but is virtually inactive with larger fusions such as Ub-β-galactosidase (Ub-βgal). Wilkinson et al. (*Science* 246: 670-673 (1989)) have also cloned a cDNA encoding a mammalian homolog of the yeast Yuh1 protease. Tobias and Varshavsky (*J. Biol. Chem.* 266: 12021-12028 (1991)) reported the cloning and functional analysis of another yeast gene, named UBP1, which encodes a Ub-specific processing protease whose amino acid sequence is dissimilar to those of the Yuh1 protease and other known proteins. Unlike YUH1 and its known homologues in other species, Ubp1 deubiquitinates ubiquitin fusion proteins irrespective of their size or the presence of an N-terminal ubiquitin extension.

SUMMARY OF THE INVENTION

The subject invention relates to a generic class of ubiquitin-specific proteases which specifically cleave at the C-terminus of the ubiquitin moiety in a ubiquitin fusion protein irrespective of the size of the ubiquitin fusion protein. More specifically, the invention relates to ubiquitin-specific proteases of this class which have been isolated from a cell. The invention also relates to isolated DNA sequences encoding the proteases of this class.

One useful property of ubiquitin-specific proteases is that they cleave ubiquitin from its C-terminal extensions irrespective of the identity of the extension's residue abutting the cleavage site. This property of the Ubp proteases make possible the in vivo or in vitro generation of proteins or peptides bearing predetermined N-terminal residues, a method with applications in both basic research and biotechnology.

DETAILED DESCRIPTION OF THE INVENTION

Figure 1:
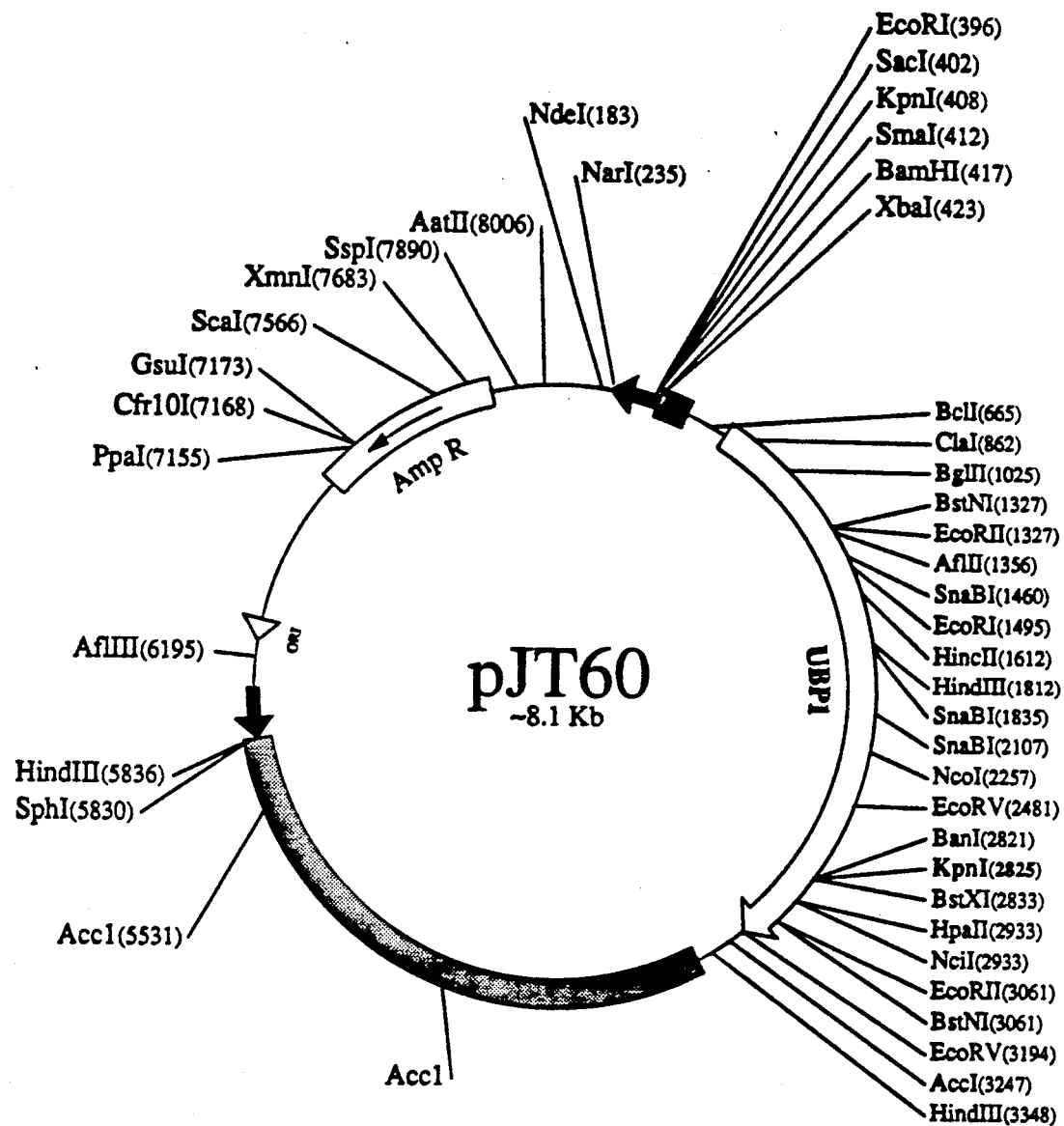
FIG. 1 is a diagram representing the plasmid pJT60.

A ubiquitin fusion protein, as used herein, is defined as a fusion protein comprising ubiquitin or its functional homolog having its C-terminal amino acid residue fused to the N-terminal amino acid residue of a non-ubiquitin protein or peptide. As discussed in the Examples which follow, the ubiquitin fusion protein can be a naturally occurring fusion protein, or a fusion protein produced by recombinant DNA technology. The specific cleavage takes place either in vivo or in vitro, between the C-terminal residue of ubiquitin and the N-terminal residue of the protein or peptide.

In contrast to the class of ubiquitin-specific proteases disclosed herein, the previously isolated YUH1 enzyme cleaves ubiquitin off a ubiquitin fusion protein only if the non-ubiquitin portion of the fusion is relatively short (shorter than about 60 residues). Since, for instance, many of the pharmaceutically important proteins are much longer than 60 residues, the YUH1 protease cannot be used to deubiquitinate fusions of these proteins with ubiquitin. The proteases of the class disclosed herein, however, can be used for this purpose, thereby allowing the generation of desired residues at the N-terminal of either large or small proteins, polypeptides or peptides (the terms protein, polypeptide and peptide are often used interchangeably in the art).

Disclosed in the Examples which follow are DNA sequences which encode three of the proteases which are members of the class of ubiquitin-specific proteases to which this invention pertains. These proteases have been designated UBP1, UBP2 and UBP3. The DNA sequences which encode these proteases, and their deduced amino acid sequences, are set forth in Sequence I.D. Numbers 3-4, Sequence I.D. Numbers 5-6 and Sequence I.D. Numbers 7-8, respectively. The DNA sequences which encode the proteases disclosed herein can be isolated by the methods described below, or by using the polymerase chain reaction amplification method. Primer sequences to be used in such an amplification method can be determined by reference to the DNA Sequence Listing below.

The proteases UBP1 and UBP2 demonstrate activity both in vivo and in vitro, whereas the UBP3 protease demonstrates activity only in vivo. Each of these proteases has been shown to specifically cleave a ubiquitin fusion protein having a molecular weight of about 120 kilo-daltons (ubiquitin-methionine-$\beta$-galactosidase). By contrast, the YUH1 ubiquitin-specific protease is virtually inactive with this ubiquitin fusion either in vitro or in vivo. The DNA sequence encoding this 120 kilodalton fusion protein is represented in Sequence I.D. Number 1. The amino acid sequence is represented in Sequence I.D. Numbers 1-2.

The scope of the invention encompasses an isolated DNA sequence encoding a ubiquitin-specific protease, or a biologically active portion thereof, which is characterized by the ability to hybridize specifically with the DNA sequence represented in Sequence I.D. Number 3, Sequence I.D. Number 5 or Sequence I.D. Number 7, under stringent hybridization conditions. DNA sequences which hybridize to the listed sequences under stringent hybridization conditions are either perfectly complementary, or highly homologous to the listed sequence. Homologous, as used herein, refers to DNA sequences which differ from the listed sequence, but the difference has no substantial effect on the biological activity (i.e., cleavage properties) of the encoded protease. One of the possible sets of stringent hybridization conditions is 50% formamide, 5×SSPE (1×SSPE is 0.15 mMaCl, 1 mM Na-EDTA, 10 mM Na-phosphate, pH 7.0), 5×Denhardt's solution (0.1% polyvinylpyrrolidone, 0.1% Ficoll) at 45° C.

The isolated DNA sequences which fall within the scope of this invention can be used to express the encoded protease in large quantities in either prokaryotic or eukaryotic host cells. For this purpose, the DNA is inserted into a prokaryotic or eukaryotic expression vector, with the appropriate regulatory signals, and used to transform cells. A variety of appropriate vectors and regulatory signals have been previously developed for this purpose and are well known to those skilled in the art.

As discussed in the Examples below, the proteases of this invention have been overexpressed in *E. coli* to the extent that they represent a substantial proportion of the total cellular protein. The purification of a protein which is expressed at such substantial levels, and for which a simple assay system is established, is a straightforward matter to one skilled in the art.

Isolated UBP1 or UBP2, or a cellular extract containing UBP1 or UBP2 produced from a recombinant DNA expression vector can be used to cleave ubiquitin off ubiquitin fusions in vitro. A cellular extract can be prepared from a culture of host cells expressing a recombinant DNA expression vector by simply concentrating and lysing the cell culture. The lysis can be followed, optionally, by various degrees of purification as described above. The range of conditions appropriate for in vitro cleavage can be determined empirically by one skilled in the art, using no more than routine experimentation, from the information provided in the Examples which follow.

In addition, the UBP1, UBP2 and UBP3 proteases can be used to deubiquitinate fusion proteins in vivo. For example, prokaryotic cells harboring an expression vector encoding the protease can be transformed with an expression vector encoding a ubiquitin fusion protein. Such cells will produce a deubiquitinated product having a predetermined N-terminal amino acid residue. There are many well known advantages to producing recombinant proteins in prokaryotic organisms such as *E. coli*.

In some fusions of ubiquitin to a non-ubiquitin protein or peptide, the presence of the ubiquitin moiety may inhibit or modify the functional activity of the non-ubiquitin protein or peptide. In this case, ubiquitin can be used as a temporary inhibitor (or modifier) of the functional activity of the non-ubiquitin protein or peptide, with the ability to restore the original functional activity at any desired time, either in vitro or in vivo, by contacting the corresponding ubiquitin fusion with the ubiquitin-specific protease to remove the ubiquitin moiety.

The invention is further illustrated by the following Examples.

EXAMPLES

Example 1

Cloning and Analysis of UBP1

Preparation of Yeast Genomic DNA Library and Lysate for Screening

*Escherichia coli* (strain HB101) transformed with a *Saccharomyces cerevisiae* genomic library was used for a sib selection strategy. The library, RB237, was produced by partially digesting yeast genomic DNA with SauIIIA and ligating the fragments into the BamH1 site in the Tet$^R$ gene of the yeast/*E. coli* shuttle vector YC$_p$50. Upon initial analysis, the library contained inserts with an average size of ~19 Kb.

*E. coli*, transformed with the above library, were plated on agar containing Luria Broth (LB) and ampicillin (amp) (100μg/ml) at a density of about 40 viable cells per plate. The plates were incubated at 36° C. for 16 hours. The colonies were then replicated onto LB/amp plates. The original plates were stored at 4° C., and their replicas were grown for 24 hours at 36° C. Each replicate was eluted with 1 ml of LB/amp (50 μg/ml) by repeated washing over the surface of the plate until all of the colonies were loosened into the liquid. The entire eluate was then added to 4 ml of LB/amp, and incubated on a roller drum at 36° C. overnight.

The *E. coli* cells in these overnight (stationary-phase) cultures were then lysed. 1.7 ml of each culture was placed in a microcentrifuge tube on ice, and then centrifuged at 12,000 × g for 1 min at 4° C. The cell pellet was resuspended, by vortexing at high speed, in 50 μl of 25% sucrose (w/v), 250 mM Tris-HCl (pH 8.0). 10μl of freshly made lysozyme solution (10 mg/ml chicken egg-white lysozyme (Sigma) in 0.25 M Tris-HCl (pH 8.0)) was then added, and mixed by light vortexing. The suspension was incubated on ice for 5 minutes, 150 μl of 75 mM EDTA, 0.33 M Tris-HCl (pH 8.0) was then added, mixed by light vortexing, and the tube was incubated on ice for 5 minutes with occasional stirring. 1 μl of 10% Triton X-100 (Pierce) was then added to each tube, and mixed by pipetting. The cell lysate was centrifuged at 12,000 × g for 15 minutes 4° C. The supernatant was retained on ice, and the pellet was discarded.

Preparation of Labeled Substrate

Cell lysates were assayed for the Ub-specific protease activity using a $^{35}$S-labeled substrate. $^{35}$S-labeled ubiquitin-methionine-dihydrofolate reductase (Ub-Met-DHFR) was prepared as follows: Luria Broth (50 ml) supplemented with 50 μg/ml ampicillin was inoculated with 1 ml of a saturated overnight culture of *E. coli* strain JM101 containing a plasmid expressing the Ub-Met-DHFR fusion protein from an IPTG-inducible, highly active derivative of the lac promoter. The cells were grown with shaking at 37° C. until they reached an $A_{600}$ of ~0.9. The culture was chilled on ice for 15 minutes, then centrifuged at 3000×g for 5 minutes and washed 2 times with M9 salts at 0° C. The cells were resuspended after the final wash in 25 ml of M9 salts supplemented with 0.2% glucose, 1.8 μg/ml thiamine, 40 μg/ml ampicillin, 1 mM IPTG, 0.0625% (w/v) methionine assay medium (Difco). The suspension was then shaken for 1 hour at 37° C. and the cells were labeled by the addition of 1 mCi of $^{35}$S-Translabel (ICN), followed by a 5-min incubation, with shaking. Unlabeled L-methionine was then added to a final concentration of 0.0032% (w/v), and the cells were shaken for an additional 10 min. The cells were then harvested (3000×g for 5 minutes) and washed once in cold M9 salts. After the M9 wash, the cell pellet was resuspended in 0.5 ml 25% Sucrose, 50 mM Tris-HCl (pH 8.0), and incubated on ice for 5 minutes. During this time, chicken egg-white lysozyme (Sigma) was dissolved freshly in 250 mM Tris-HCl (pH 8.0) to a concentration of 10 mg/ml. 10 μl of the lysozyme solution was added to the cell suspension, mixed, and incubated for 5 minutes at 0° C. 5 μl of 0.5M EDTA (pH 8.0) was then added, and the suspension left at 0° C. for 5 minutes, with intermittent mixing. The cell suspension was then added to a centrifuge tube containing 0.975 ml of 65 mM EDTA (pH 8.0), 50 mM Tris-HCl (pH 8.0) and protease inhibitors antipain, chymostatin, leupeptin, aprotinin and pepstatin, each at 25 μg/ml. 10 μl 10% Triton X-100 (Pierce) was then added, and dispersed by pipetting. The lysate was centrifuged at 39,000×g for 30 minutes. The supernatant was retained, quickly frozen in liquid nitrogen, and stored at −85° C.

To affinity-purify the $^{35}$S-labeled Ub-Met-DHFR, a methotrexate (MTX)-agarose affinity matrix was prepared according to the method of Kaufman (*Meth. Enzymol.* 34:272-281 (1974)). A 0.5 ml bed volume column was filled with the MTX-agarose, and washed with 10 ml of MTX column buffer (20 mM Hepes (pH 7.5), 1 mM EDTA 200 mM NaCl, 0.2 mM dithiothreitol). The $^{35}$S-labeled supernatant of the preceding step was thawed and applied to the MTX-agarose column. The column was washed with 50 ml of MTX column buffer, 50 ml of MTX column buffer containing 2M urea, and again with 50 ml of MTX column buffer. The labeled Ub-Met-DHFR was eluted from the column with folic acid elution buffer (0.2M potassium borate (pH 9.0), 1M KCl, 1 mM DTT, 1 mM EDTA, 10 mM folic acid). The elution buffer was applied to the column in 1 ml aliquots, and 1 ml fractions were collected. The fractions were assayed for $^{35}$S radioactivity and those fractions that contained the major radioactive peak were pooled. The pooled fractions were dialyzed for ~20 hours against two changes of a storage buffer containing 40 mM Tris-HCl (pH 7.5), 1 mM $MgCl_2$, 0.1 mM EDTA, 50% glycerol. The purified $^{35}$S-labeled Ub-Met-DHFR was assayed by SDS-PAGE, followed by fluorography and found to be greater than 95% pure.

Deubiquitination Assay

The cell lysates were assayed for the Ub-specific protease activity, by combining 9 μl of the cell lysate supernatant with 1 μl of the affinity purified $^{35}$S-labeled Ub-Met-DHFR fusion in a 0.5 ml microcentrifuge tube, and incubated at 36° C. for 3 hr. 5 μl of a 3-fold concentrated electrophoretic sample buffer (30% glycerol, 3% SDS (w/v), 15 mM EDTA, 0.2M 2-mercaptoethanol, 0.3 μg/ml bromophenol blue, 375 mM Tris-HCl (pH 6.8) was then added, and each tube was placed in a boiling water bath for 3 min. The samples were loaded onto a 12% polyacrylamide-SDS gel, and electrophoresed at 50 V until the bromophenol dye reached the bottom of the gel. Positions of the radioactively labeled proteins in the gel were visualized by fluorography. The gel was washed in 10% acetic acid, 25% methanol for 15 minutes, rinsed in $H_2O$ for 15 minutes and incubated with Autofluor (National Diagnostics) for 1 hour. The gel was then dried at 80° C. under vacuum, placed in a light-proof cassette against Kodak XAR-5 film and stored at −85° C. overnight.

The above deubiquitination assay was repeated with lysates from different pools of *E. coli* transformants until the gel analysis revealed a lysate that displayed proteolytic activity acting at the ubiquitin-DHFR junction. This assay indicated that at least one of the ~40 *E. coli* colonies on the original LB/amp plate (from which the pooled lysate had been derived) contained a YCp50-based plasmid having a yeast DNA insert conferring Ub-specific proteolytic activity.

The next step of this sib selection approach to cloning the UBP1 gene was to carry out a similar Ub-Met-DHFR cleavage assay to determine which of the ~40 colonies in a "positive" pool contained the desired plasmid. To do so, a sample of each individual colony on the plate of interest was inoculated into LB/amp and grown overnight. The Ub-Met-DHFR cleavage assay was then repeated exactly as above, but this time each lysate sample was representative of a single clonal *E. coli* transformant rather than a mixture of ~40 such transformants. This analysis revealed a single colony that contained a plasmid which conferred the ability to specifically cleave at the Ub-DHFR junction.

Cloning and DNA Sequence Analysis of UBP1

Analysis of the initially isolated plasmid (pJT55) revealed a ~15 kb insert of yeast genomic DNA in the YCp50 vector. SphI digestion of this plasmid yielded a ~14 kb fragment, which, upon subcloning into the vector pUC19, conferred the same proteolytic activity. This plasmid was called pJT57. The ~14 kb fragment was subcloned further by cutting with SphI and XhoI, isolating the ~5.5 kb of the insert DNA and subcloning it into the pUC19 vector pre-cut with SphI and SalI. This resulted in ~8.1 kb plasmid pJT60 containing the ~5.5 kb yeast DNA insert that conferred the same Ub-specific proteolytic activity as the original plasmid.

A map showing restriction endonuclease recognition sites in plasmid pJT60 is shown in FIG. 1. In the map, base pair positions are indicated by a number in parentheses following a restriction site. The yeast DNA insert in pJT60 contained a KpnI site near its center that divided the insert into two smaller fragments A and B (bases 423 and 5830). In this fragment, the open arrow indicates the open reading frame (ORF) representing UBP1. The entire ORF, and the thin lines bracketing it, represent the extent of the sequenced DNA shown in Sequence I.D. Number 3. Both fragments were subcloned into pUC19, yielding pJT60A and pJT60B. Fragment A was isolated from pJT57 after cutting with KpnI and SphI. This fragment was subcloned into pUC19 that had been cut with the same restriction endonucleases. Fragment B was isolated from pJT57 that had been cut by KpnI and XhoI; it was subcloned into pUC19 that had been cut by KpnI and SalI. Neither pJT60A nor pJT60B was able to confer Ub-specific proteolytic activity. This result suggested that the gene of interest straddled the KpnI site of the ~5.5 kb insert of pJT60.

To sequence the cloned gene, the inserts of pJT60A and pJT60B were subcloned into the M13mp19 phage vector. Nucleotide sequence was determined (using the chain termination method) in both directions from the internal KpnI site in pJT60. The KpnI site was found to be ensconced within an open reading frame extending from this site in both directions. Unidirectional deletions were then made in the sequencing templates by the methods of Dale et al., (*Plasmid* 13:31–40 (1989)) and the entire open reading frame (ORF) was determined. The 5' end of the ORF was in fragment B and the termination codon was in fragment A. The ORF was 2427 nucleotides long, and encoded an 809-residue protein, with a molecular mass of 93 kD. The sequenced ORF was then isolated on a 2.8 kb fragment by cutting pJT60 with AccI, filing in the 5' overhangs with Klenow PolI, and ligating SalI linkers to the blunt ends. This construct was digested with SalI and BamHI, the 2.8 kb fragment was electrophoretically purified and ligated into pUC19 that had been digested with BamHI and SalI. The resulting plasmid was called pJT70. This plasmid, when transformed into *E. coli*, was able to confer the Ub-specific proteolytic activity to the same extent as either the original ~15 kb insert in YCp50 or the ~5.5 kb insert of the pJT60 plasmid that includes the ~2.8 kb fragment of pJT70. The plasmid pJT60 has been deposited with the American Type Culture Collection (Rockville, Md.), and has been assigned ATCC designation 68211. The 2.8 kb fragment contained no other ORFs of significant size, indicating that the sequenced ORF shown in Sequence I.D. Number 3 encoded the Ub-specific protease. This new gene has been named UBP1, for Ubiquitin-specific protease.

Substrate Specificity of UBP1

The in vitro substrate specificity of the UBP1 encoded product was examined by testing for cleavage using a variety of substrates. These experiments demonstrated the ability of Ubp1 to deubiquitinate [$^{35}$S]Ub-Met-DHFR and [$^{35}$S]ubiquitin-methionine-$\beta$-galactosidase (Ub-Met-$\beta$gal). The construction of the [$^{35}$S]Ub-Met-$\beta$gal fusion protein has been described previously (Bachmair et al., *Science* 234: 179–186 (1986)). The labeled substrates were employed in a deubiquitination assay as described above. Both fusion proteins were specifically deubiquitinated. Fluorograms of electrophoretic patterns from these deubiquitination experiments revealed deubiquitination reaction products of the expected molecular mass.

The Ubp1 protease was also shown to deubiquitinate natural ubiquitin fusions to yeast ribosomal proteins (Ubi2 and Ubi3) in vitro. An expression construct encoding Ubi2, a natural ubiquitin-ribosomal protein fusion of *S. cerevisiae*, was used to transform *E. coli*. A cellular extract from a culture of the transformed cells was treated with an *E. coli* extract from cells expressing Ubp1, followed by electrophoresis in a polyacrylamide-SDS-gel, blotting onto polyvinylidene difluoride membrane, and detection using a rabbit anti-ubiquitin antibody, with subsequent application of a secondary goat anti-rabbit antibody linked to alkaline phosphatase, and colorgenic substrates of alkaline phosphatase. These experiments demonstrated that an extract from *E. coli* expressing the Ubp1 gene product effectively deubiquitinated the natural ubiquitin fusion proteins Ubi2 and Ubi3.

To determine whether a sandwich-type ubiquitin fusion protein in which the ubiquitin moiety had an N-terminal extension was a substrate for Ubp1, a plasmid was constructed that encoded a triple fusion protein consisting of an N-terminal dihydrofolate reductase (DHFR) moiety, a flexible linker region of three glycine residues and a serine, followed by ubiquitin and Met-$\beta$gal moieties. The mouse DHFR gene was isolated on a BamHI/HindII fragment from a plasmid encoding Ub-Met-DHFR (Bachmair and Varshavsky, *Cell* 56:1019–1032 (1989)). This fragment was treated with Klenow PolI to fill in the ends, and KpnI linkers were ligated. The fragment was then cut with KpnI to yield a 678 bp fragment which was cloned into the KpnI site in a modified Ub-Met-$\beta$gal expression vector in which the second codon of the ubiquitin moiety was altered to encode a KpnI site (Gonda et al., *J. Biol. Chem.* 264:16700–16712 (1989)). This procedure yielded a plasmid that encoded DHFR, ubiquitin (without the initial Met codon) and Met-$\beta$gal, with the open reading frames for each moiety not yet aligned into a single open reading frame. To effect the alignment of the open reading frames and to position the initiator codon of DHFR correctly with respect to the GAL promoter in the vector, site-directed mutagenesis was performed at two locations in the plasmid.

The plasmid was cut with BamHI and HindIII, and the ~2.76 kb fragment encoding DHFR, ubiquitin and the first few residues of Met-$\beta$gal was cloned into M13mp19 that had been cut with the same enzymes. Oligonucleotide-mediated, site-directed mutagenesis was performed using the single-stranded M13 derivative and standard protocols. The first oligodeoxynucleotide was designed to produce a 20 bp deletion that would bring the initiator codon of DHFR to a proper position relative to the GAL5 promoter of the vector. The second oligodeoxynucleotide was designed to bring together the reading frames of DHFR and ubiquitin, and to introduce the 4-residue spacer (-Gly-Gly-Gly-Ser-) between the DHFR and ubiquitin moieties. After mutagenesis, DNA clones were tested for incorporation of both changes by direct nucleotide sequencing using the chain termination method.

Figure 2:
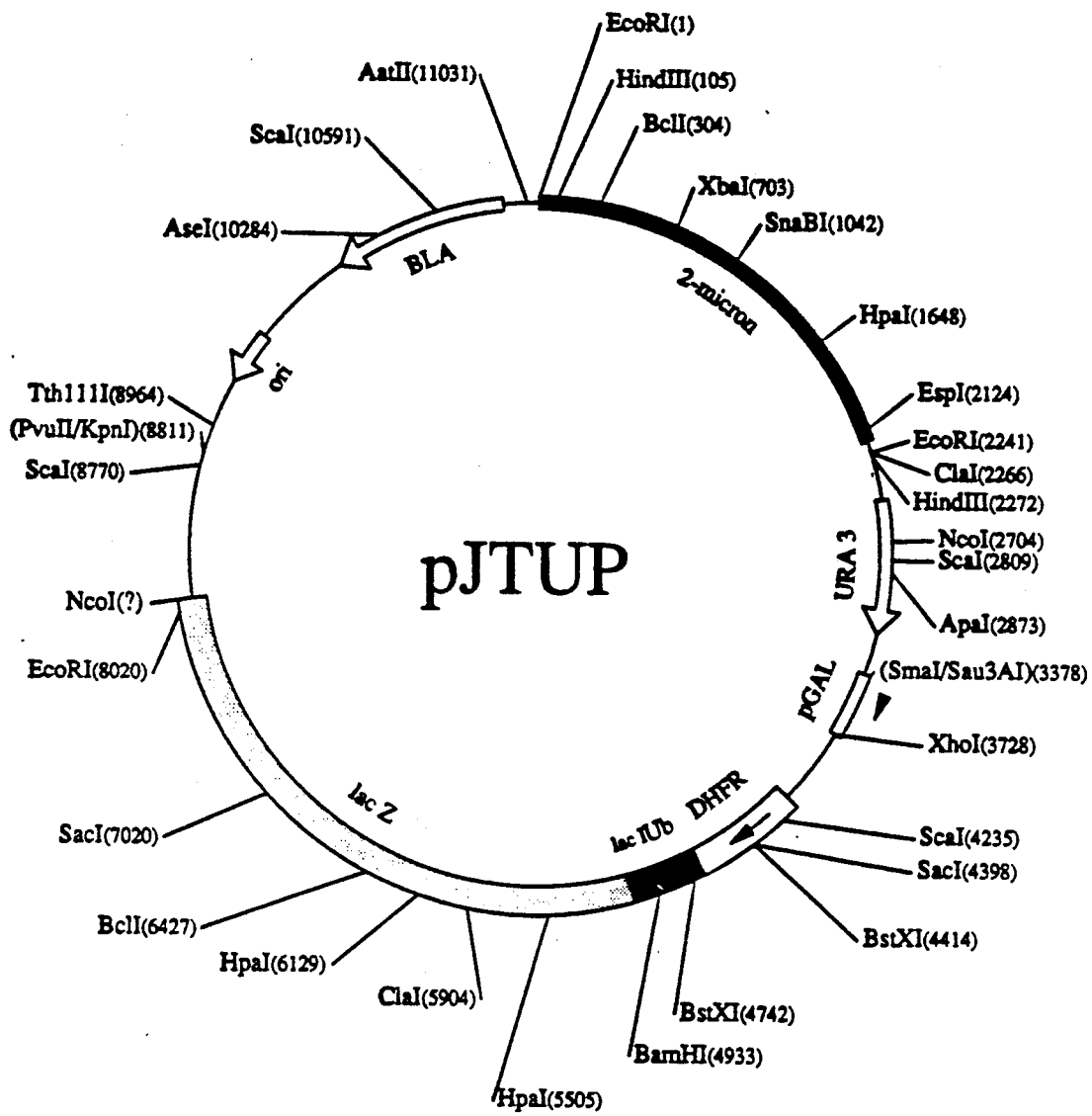
FIG. 2 is a diagram representing the plasmid pJTUP.

Double stranded, replicative form (RF) of the desired M13 clone was isolated and digested with BamHI and XhoI. The resulting ~1.2 kb fragment was cloned into the ~9.87 kb fragment of a Ub-Met-$\beta$gal expression vector digested with the same enzymes, replacing the Ub-Met-coding fragment with the DHFR-Ub-Met-coding fragment produced by the site-directed mutagenesis. This last step yielded an expression vector that encoded the triple fusion DHFR-Ub-Met-$\beta$gal. The vector was named pJTUP (FIG. 2).

pJTUP was used to test whether a ubiquitin fusion in which the ubiquitin moiety is located between two non-ubiquitin moieties would be a substrate for cleavage by Ubp1. In *E. coli* metabolically labelled with [$^{35}$S]methionine, the fate of expressed DHFR-Ub-Met-$\beta$gal was determined in the presence or absence of Ubp1 using immunoprecipitation with a monoclonal antibody to $\beta$-galactosidase, followed by polyacrylamide-SDS gel electrophoresis and fluorography. These experiments demonstrated that UBP1 efficiently cleaves the triple fusion protein.

The ability to cleave such a sandwich construct is particularly useful in situations wherein the first non-ubiquitin moiety confers some desirable property on the sandwich ubiquitin fusion. For example, the first non-ubiquitin moiety may facilitate affinity purification of the ubiquitin fusion protein. In such a case, the fusion protein can be expressed in a cell (e.g., *E. coli*) that lacks ubiquitin-specific proteases, and a cellular lysate can be passed over an affinity column specific for the first non-ubiquitin moiety. One example of a protein which is useful for affinity purification is streptavidin. Following affinity purification of the fusion protein, the latter is contacted with the ubiquitin-specific protease. The second non-ubiquitin moiety is thereby liberated from the sandwich ubiquitin fusion construct.

EXAMPLE 2

Cloning and Analysis of UBP2 and UBP3

Cloning Strategy

The strategy employed to clone the genes encoding Ub-specific proteases of *S. cerevisiae* other than Ubp1 and Yuh1 took advantage of the fact that bacteria such as *E. coli* lack ubiquitin and Ub-specific enzymes, and was also based on the recent demonstration that the N-end rule, a relation between the in vivo half-life of a protein and the identity of its N-terminal residue, operates not only in eukaryotes but in *E. coli* as well. In eukaryotes, ubiquitin fusions to test proteins such as $\beta$-galactosidase are deubiquitinated by Ub-specific processing proteases irrespective of the identity of a residue at the Ub-$\beta$gal junction, making it possible to expose in vivo different residues at the N-termini of otherwise identical test proteins. This technique, required for detection and analysis of the N-end rule in eukaryotes, has been made applicable in bacteria through the isolation of the yeast UBP1 gene (see Example 1), inasmuch as *E. coli* transformed with UBP1 acquires the ability to deubiquitinate ubiquitin fusions. The finding that an X-$\beta$gal test protein such as Arg-$\beta$gal is short-lived in *E. coli*, whereas Ub-Arg-$\beta$gal is long-lived, made possible a new *E. coli*-based in vivo screen for Ub-specific proteases. *E. coli* expressing the (long-lived) Ub-Arg-$\beta$gal fusion protein form blue colonies on plates containing X-Gal, a chromogenic substrate of $\beta$gal. However, if a deubiquitinating activity is present in the cells as well, Ub-Arg-$\beta$gal is converted into a short-lived Arg-$\beta$gal, whose low steady-state level results in white *E. coli* colonies on X-Gal plates.

To be clonable by this strategy using a conventional yeast genomic DNA library, a yeast gene must have a promoter that functions in *E. coli* (a minority of yeast promoters can do so), must lack introns in its coding region (most yeast genes lack introns), and must encode a Ub-specific processing protease that functions as a monomer or a homooligomer. One advantage of this in vivo screen over the previously used in vitro screen that yielded UBP1 is that the former requires a relevant protease to be active in vivo but not necessarily in vitro (in *E. coli* extracts).

Plasmids Expressing Ubiquitin-Containing Test Proteins

The plasmid pACUb-R-$\beta$gal, expressing Ub-Arg-$\beta$gal, was constructed by subcloning the ~5 kb ScaI fragment of pUB23-R (Bachmair et al., *Science* 234: 179–186 (1986)) that contains the Ub-Arg-$\beta$gal coding region downstream from the GAL10 promoter, into HincII-digested pACYC184, whose P15A origin of replication makes this plasmid compatible with pMB1(ColE1)-based *E. coli* vectors such as pUC19 and pBR322. pACUb-R-$\beta$gal expressed Ub-Arg-$\beta$gal in *E. coli* from the galactose-inducible yeast GAL10 promoter, which functions as a weak constitutive promoter in *E. coli*. The plasmid pACUb-M-$\beta$gal, expressing Ub-Met-$\beta$gal, was constructed identically to pACUb-R-$\beta$gal except that pUB23-M was used instead of pUB23-R. Plasmids pKKUBI2, pKKUBI3 and pUB17 expressed in *E. coli* the natural yeast ubiquitin fusions (ubiquitin precursors) Ubi2, Ubi3 and Ubi4 (polyubiquitin), respectively (Ozkaynak et al., EMBO J. 6: 1429–1439 (1987)), using an isopropylthiogalactoside (IPTG)-inducible promoter in the vector pKK223-3 (Ausubel et al., *Current Protocols in Molecular Biology*, J. Wiley & Sons, N.Y. (1989)). The plasmids pKKHUb2 and pKKHUb3 that expressed, respectively, the human diubiquitin and triubiquitin (both of which contain the naturally occurring 1-residue C-terminal extension, cysteine), were constructed as follows. A 1.77 kb BamHI fragment containing the human UbB (triubiquitin) gene from the plasmid pB8.3 was ligated into BamHI-digested pUC19 in the orientation that placed the 3' end of UbB adjacent to the SmaI site of the polylinker in pUC19, yielding pUbB. A 1.04 kb DraI/SmaI fragment of pUbB containing the UbB coding and 3' flanking regions (the DraI site is located 10 bp upstream of the UbB start codon) was subcloned into the SmaI/HincII-digested pUC19, placing the UbB start codon adjacent to the EcoRI site in the polylinker, and yielding pHUb3. This plasmid was partially digested with SalI, which cleaves once within each Ub-coding repeat (the polylinker's SalI site was removed during the construction of pHUb3); the vector-containing fragment that retained two Ub-coding repeats was isolated and self-ligated, yielding pHUb2. The inserts of pHUb2 and pHUb3 were excised with EcoRI and PstI, and subcloned into the EcoRI/PstI-cut pKK223-3, yielding, respectively, pKKHUb2 and pKKHUb3. The start codon of the Ub-coding region in these plasmids is 36 bp downstream of the Shine-Dalgarno sequence in pKK223-3.

Screening Results

*E. coli* carrying a plasmid expressing Ub-Arg-$\beta$gal were transformed with the *S. cerevisiae* genomic DNA library RB237 carried in the plasmid YCp50, plated on X-Gal plates containing antibiotics that selected for the presence of both plasmids, and incubated overnight at 37° C. Of ~800 colonies thus screened, six (named pRBW1–pRBW6) were white or pale blue, whereas the other colonies were dark blue (comparable to control colonies of *E. coli* transformed with the YCp50 vector alone). Three of the six candidate colonies were found to be false positives, two contained plasmids (termed pRBW1 and pRBW6) with overlapping inserts of yeast DNA, while the remaining colony contained a plasmid (termed pRBW2) with a distinct yeast DNA insert. Plasmids pRBW1 and pRBW2 were isolated and re-transformed into *E. coli* expressing either Ub-Arg-$\beta$gal or Ub-Met-$\beta$gal. Transformants expressing Ub-Arg-$\beta$gal formed white colonies on X-Gal plates, confirming the original results, whereas transformants expressing Ub-Met-$\beta$gal formed blue colonies on these plates, indicating that the metabolic destabilization of Ub-Arg-$\beta$gal by inserts in pRBW1 and pRBW2 was N-end rule-specific. (Arg and Met are, respectively, destabilizing and stabilizing residues in the *E. coli* N-end rule).

Surprisingly, extracts of *E. coli* carrying pRBW1 or pRBW2 were inactive in an in vitro deubiquitinating assay with Ub-Met-DHFR, suggesting that Ub-specific proteases encoded by pRBW1 and pRBW2 were either inactivated in cell extracts or, alternatively, could deubiquitinate ubiquitin fusions cotranslationally but not posttranslationally. The Ub-specific protease activities conferred by pRBW1 and pRBW2 on *E. coli* were therefore assayed in vivo by pulse-chase analyses with Ub-Met-βgal, using a monoclonal antibody to βgal. The results confirmed that pRBW1 and pRBW2 (but not the YCp50 vector alone) did confer deubiquitinating activity on *E. coli*. Subsequent overexpression of Ub-specific proteases encoded by pRBW1 and pRBW2 made possible their detection in *E. coli* extracts as well.

Figure 3:
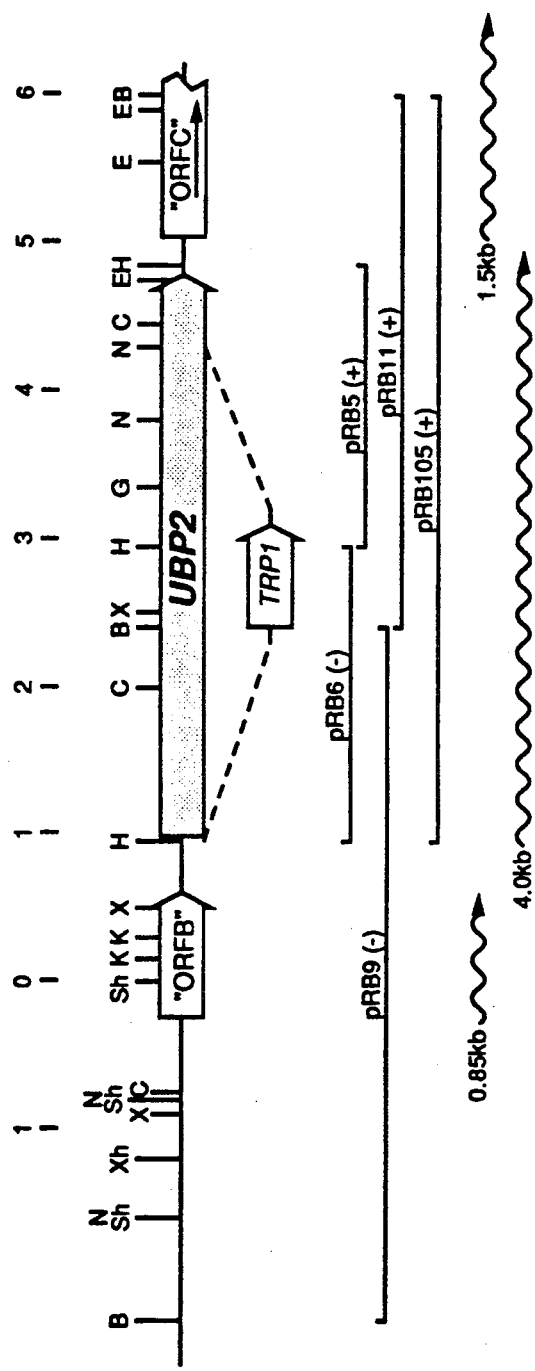
FIG. 3 is a diagram representing a restriction map of UBP2.

The ORF encoding deubiquitinating activity of pRBW2 was identified by subcloning experiments and nucleotide sequencing, and was named the UBP2 gene (FIG. 3 and Sequence I.D. Number 5). The position of the start (ATG) codon in the UBP2 was inferred so as to yield the longest (3715 bp) ORF encoding an acidic (calculated pI of 4.95), 1264-residue (145 kDa) protein.

Figure 4:
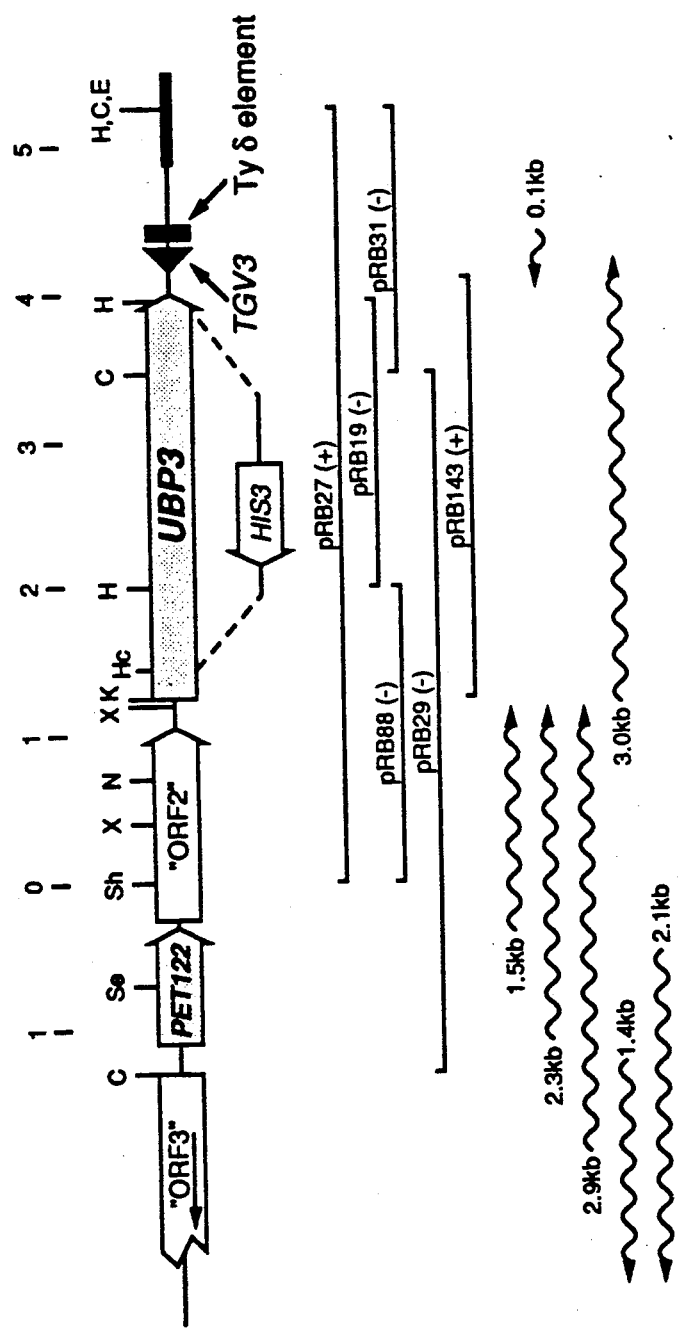
FIG. 4 is a diagram representing a restriction map of UBP3.

The ORF encoding deubiquitinating protease of pRBW1 was identified by subcloning experiments and nucleotide sequencing, and was named the UBP3 gene (FIGS. 4 and Sequence I.D. Number 7). The position of the start (ATG) codon was inferred so as to yield the longest (2736 bp) ORF, which encodes a slightly basic (calculated pI of 7.92), 912-residue (102 kDa) protein. A plasmid (pRB143) containing this ORF downstream of an *E. coli* promoter conferred deubiquitinating activity on *E. coli*.

Expression of UBP1, UBP2 and UBP3 in *E. coli*

The previously constructed plasmids pJT70 (pUC19-based) and pJT184 (pACYC184-based) expressed the yeast UBP1 in *E. coli* from the yeast UBP1 promoter, which is weakly active in *E. coli*. Although a 1.9 kb HindIII subclone of pRBW2 conferred deubiquitinating activity on *E. coli*, it contained only the 3' half of the UBP2 ORF. Pilot experiments indicated that the truncated Ubp2 protein yielded variable levels of deubiquitinating activity in *E. coli* extracts. To construct a plasmid that expressed the full-length Ubp2 in *E. coli*, a 5' portion of UBP2, isolated as the 1.56 kb HindIII/XbaI fragment of pRB6 (see FIG. 3), was subcloned into pRS316 (Sikorski and Hieter, *Genetics* 122: 19–27 (1989)), which contains a polylinker, placing an EcoRI site close to the HindIII site in UBP2. The resulting insert was then excised as the 1.57 kb EcoRI/XbaI fragment. A 3' portion of UBP2 was isolated as the ~3.4 kb XbaI/BamHI fragment from pRB11 (see FIG. 3), and subcloned into pRS316, placing a PstI site close to the BamHI site in UBP2. The resulting insert was then excised as a ~3.4 kb XbaI/PstI fragment. This fragment and the above 1.57 kb EcoRI/XbaI fragment were ligated into the EcoRI/XbaI-cut pKK223-3, yielding (among other products) the plasmid pRB105, which contained UBP2 in the correct orientation, 50 bp downstream from the Shine-Dalgarno sequence of pKK223-3. For experiments requiring the simultaneous presence of two distinct plasmids in *E. coli*, the UBP2/rrnB terminator region of pRB105 was excised as the ~6.4 kb SphI/ScaI fragment, and subcloned into the SphI/EcoRV-cut pACYC184, yielding pRB173.

Since in the initial experiments, the Ub-specific protease activity of Ubp3 could be detected in vivo but not in *E. coli* extracts, a UBP3-overexpressing plasmid was constructed. The ~2.9 kb KpnI/DraI fragment of pRB27 that contained the entire UBP3 gene was subcloned into the KpnI/HincII-cut pUC19, placing the EcoRI and the PstI site of the plasmid near, respectively, the KpnI site and the DraI site of the introduced insert. The insert was then excised with EcoRI/PstI and subcloned into the EcoRI/PstI-cut pKK223-3, yielding pRB143, which contained UBP3 in the correct orientation, 50 bp downstream form the Shine-Dalgarno sequence of pKK223-3. For experiments requiring the simultaneous presence of two distinct plasmids in *E. coli*, the UBP3/rrnB terminator region of pRB143 was excised as the ~4.2 kb SphI/ScaI fragment and subcloned into the SphI/EcoRV-cut pACYC184, yielding pRB175.

In more recent experiments, UBP1, UBP2 and UBP3 were overexpressed in *E. coli* from a pKK-based expression vector (Ausubel et al., *Current Protocols in Molecular Biology*, J. Wiley & Sons, N.Y. (1989)). Each of the UBP proteins was expressed to a level where it comprises a substantial proportion (1–5%) of the total cellular protein.

Sequence Comparisons of Ub-specific Proteases

Sequence alignment of the 809-residue Ubp1, 1264-residue Ubp2 and 912-residue Ubp3 demonstrated the lack of overall sequence similarity between these proteins, as well as the presence of two short regions of statistically significant similarity that are spaced a few hundred residues apart in each of the Ubp proteases. The two regions of similarity are centered around a Cys and two His residues. As has been seen with Ubp1, neither Ubp2 nor Ubp3 have significant sequence similarities to the fourth Ub-specific protease of yeast, Yuh1 or its mammalian homologs. The region in Yuh1 and its mammalian homologs that contains a putative active-site Cys residue is not similar to the conserved "Cys" region of Ubp1–Ubp3: apart from the Cys residue, only one other residue position is occupied by an identical residue (Asn) in all six proteins. No such identities are seen in an analogous alignment of the two conserved His residues in Yuh1-like proteases with either of the conserved His residues in Ubp1–Ubp3.

In Vitro Properties of Ub-specific Proteases

The previously characterized Ubp1 protease can efficiently deubiquitinate in vitro a variety of linear ubiquitin fusion proteins, including the natural ubiquitin precursors Ubi1–Ubi3 and engineered fusions such as Ub-X-βgal and Ub-X-DHFR. Similar assays, in which an extract of *E. coli* carrying an overexpression vector-based plasmid expressing either Ubp2 (pRB105), Ubp3 (pRB143), or Yuh1 (pKKYUH1) is incubated with Ub-containing test proteins, were used to analyze in vitro the substrate specificity of these proteases. Extracts of *E. coli* carrying the UBP1-expressing plasmid pJT70 or vector alone, were also used in these assays. The cleavage products were fractionated by SDS-PAGE and visualized by immunoblotting, using anti-Ub antibodies or, with purified, $^{35}$S-labeled test proteins, directly by fluorography.

In these in vitro assays, the Ubp2 protease efficiently deubiquitinated Ub-Met-βgal and Ub-Met-DHFR, as well as Ubi2 and Ubi3, the natural precursors of ubiquitin, in which it is fused to specific ribosomal proteins. Both Ubp1 and Ubp2 released the Cys residue from Ub-Ub-Cys (diubiquitin bearing a one-residue C-terminal extension) but were unable to cleave at the Ub-Ub junction in Ub-Ub-Cys. Ubp1 and Ubp2 were also unable to cleave at the Ub-Ub junctions in the yeast polyubiquitin, a natural ubiquitin precursor containing five head-to-tail ubiquitin repeats as was previously reported for Ubp1. Thus, Ubp1 and Ubp2 efficiently cleaved in vitro after the last (Gly$^{76}$) residue of ubiquitin in all of the tested ubiquitin fusions, the Ub-Ub linkage in polyubiquitins being the single exception. However, as shown below, these proteases are able to cleave polyubiquitin when coexpressed with it E. coli.

Although the expression of Ubp3 in E. coli from the pKK overexpression vector-based plasmid pRB143 resulted in a substantial overproduction of a protein with the expected molecular mass, extracts of Ubp3-expressing E. coli lacked deubiquitinating activity. Since Ubp3 is certainly active in E. coli in vivo, it is either inactivated in cell extracts or is able to cleave ubiquitin fusions exclusively during or shortly after their ribosome-mediated synthesis.

In agreement with previously reported findings, extracts of E. coli expressing Yuh1 efficiently deubiquitinated short ubiquitin fusions such as Ubi2 and Ubi3. However, Yuh1 was much less active against the larger fusion Ub-Met-DHFR (a 229-residue C-terminal extension of ubiquitin), deubiquitinating at most ~50% of the fusion even after a prolonged incubation, and was virtually inactive against Ub-Met-βgal (Sequence I.D. Numbers 1-2).

In Vivo Properties of Ub-specific Proteases

As expected from their activities in E. coli extracts, both Ubp1, Ubp2 and Yuh1 were active in vivo against the natural ubiquitin fusions Ubi2 and Ubi3. Ubp3, which was inactive in E. coli extracts, efficiently deubiquitinated Ubi2 and Ubi3 when coexpressed with them in E. coli. While Ubp1 and Ubp2 were unable to cleave at the Ub-Ub junction in polyubiquitins in vitro, both of them were active against yeast polyubiquitin when coexpressed with it in E. coli. In contrast, the Ubp3 protease, while active in vivo against ubiquitin fusions such as Ubi2 and Ubi3, was inactive, under the same conditions, against polyubiquitin. These distinctions among Ub-specific processing proteases indicate subtle differences in their requirements for the conformation of protein domains in the vicinities of Ub-X peptide bonds.

The in vivo deubiquitination of ubiquitin fusions such as Ub-Met-βgal by Ubp2 and Ubp3 was also followed by pulse-chase analysis, in part to confirm the findings of the original X-Gal screen. As expected, both proteases deubiquitinated Ub-Met-βgal in vivo, except that the cleavage by Ubp3 was incomplete, and a significant proportion of pulse-labeled Ub-Met-βgal remained intact 15 min after the pulse. These results are consistent with the pattern of deubiquitination by Ubp3 that is more strictly cotranslational than that by Ubp2. In a similar pulse-chase assay, Yuh1 was unable to deubiquitinate Ub-Met-βgal in vivo, indicating that an apparently greater susceptibility of the Ub-Met peptide bond in a nascent (as distinguished from mature) Ub-Met-βgal is insufficient to allow its deubiquitination by Yuh1. By contrast, this difference is sufficient to allow a cotranslational (but apparently not posttranslational) deubiquitination of Ub-Met-βgal by Ubp3.

Equivalents

Those skilled in the art will recognize or be able to ascertain, using no more than routine experimentation, many equivalents to the specific embodiments of the invention described herein. Such equivalents are intended to be encompassed by the claims which follow the Sequence Listing.

We claim:

1. An isolated DNA encoding a ubiquitin-specific protease, or a biologically active portion thereof, said portion encoding said protease, which specifically cleaves a ubiquitin fusion protein having a molecular weight of about 120 kilodaltons, the specific cleavage taking place in vitro between the C-terminal residue of ubiquitin and the N-terminal residue of the protein or peptide, the fusion protein being encoded by the DNA represented in Sequence I.D. Number 1.

2. An isolated DNA of claim 1 which is characterized by the ability to hybridize specifically with the DNA sequence represented in Sequence I.D. Number 3 under stringent hybridization conditions.

3. An isolated DNA of claim 1 which is characterized by the ability to hybridize specifically with the DNA sequence represented in Sequence I.D. Number 5 under stringent hybridization conditions.

4. An isolated DNA encoding a ubiquitin-specific protease, or a biologically active portion thereof, said portion encoding said protease, which specifically cleaves a ubiquitin fusion protein having a molecular weight of about 120 kilodaltons, the specific cleavage taking place in a prokaryotic cell between the C-terminal residue of ubiquitin and the N-terminal residue of the protein or peptide, the fusion protein being encoded by DNA represented in Sequence I.D. Number 1.

5. An isolated DNA of claim 4 which is characterized by the ability to hybridize specifically with the DNA represented in Sequence I.D. Number 3 under stringent hybridization conditions.

6. An isolated DNA of claim 4 which is characterized by the ability to hybridize specifically with the DNA represented in Sequence I.D. Number 5 under stringent hybridization conditions.

7. An isolated DNA of claim 4 which is characterized by the ability to hybridize specifically with the DNA represented in Sequence I.D. Number 7 under stringent hybridization conditions.

8. An isolated DNA expression construct encoding a biologically active ubiquitin-specific protease comprising a DNA characterized by a sequence selected from the group consisting of Sequence I.D. Number 3, Sequence I.D. Number 5 and Sequence I.D. Number 7, or a portion of these sequences, said portion encoding said protease in expressible form.

9. A cell transformed with a heterologous DNA expression construct encoding a biologically active ubiquitin-specific protease comprising a DNA characterized by a sequence selected from the group consisting of Sequence I.D. Number 3, Sequence I.D. Number 5 and Sequence I.D. Number 7, or a portion of these sequences, said portion encoding said protease in expressible form.

10. A cell of claim 5 which is a prokaryotic cell.

11. A cell of claim 10 which is *E. coli.*

* * * * *

UNITED STATES PATENT AND TRADEMARK OFFICE
CERTIFICATE OF CORRECTION

PATENT NO. : 5,212,058

DATED : May 18, 1993

INVENTOR(S) : Rohan T. Baker, John W. Tobias and Alexander Varshavsky

It is certified that error appears in the above-identified patent and that said Letters Patent is hereby corrected as shown below:

Claim 10, Column 66, line 24, cancel "claim 5" and insert therefor --claim 9--.

Signed and Sealed this

Fourteenth Day of December, 1993

Attest:

BRUCE LEHMAN

Attesting Officer

Commissioner of Patents and Trademarks